US012797300B2

(12) United States Patent
Hayashi et al.

(10) Patent No.: US 12,797,300 B2
(45) Date of Patent: Nov. 17, 2026

(54) MEDICATION SUPPORT DEVICE

(71) Applicants: Hirotaka Hayashi, Kanagawa (JP); Terumitsu Azuma, Kanagawa (JP); Yoshihide Sugiyama, Kanagawa (JP); Hiroshi Fujie, Kanagawa (JP); Manabu Yamanaka, Kanagawa (JP); Takato Mochizuki, Kanagawa (JP); Youhei Niitsuma, Kanagawa (JP); Yu Yamaya, Kanagawa (JP); Sachika Tashiro, Kanagawa (JP)

(72) Inventors: Hirotaka Hayashi, Kanagawa (JP); Terumitsu Azuma, Kanagawa (JP); Yoshihide Sugiyama, Kanagawa (JP); Hiroshi Fujie, Kanagawa (JP); Manabu Yamanaka, Kanagawa (JP); Takato Mochizuki, Kanagawa (JP); Youhei Niitsuma, Kanagawa (JP); Yu Yamaya, Kanagawa (JP); Sachika Tashiro, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 199 days.

(21) Appl. No.: 18/903,122

(22) Filed: Oct. 1, 2024

(65) Prior Publication Data

US 2025/0114279 A1 Apr. 10, 2025

(30) Foreign Application Priority Data

Oct. 10, 2023 (JP) ................................ 2023-175440

(51) Int. Cl.
*A61J 7/00* (2006.01)
*G16H 20/13* (2018.01)

(52) U.S. Cl.
CPC .......... *A61J 7/0084* (2013.01); *A61J 7/0069* (2013.01); *G16H 20/13* (2018.01)

(58) Field of Classification Search
CPC ...... A61J 7/0427; A61J 7/0454; A61J 7/0463; A61J 7/0069; A61J 7/0076; A61J 7/0084;
(Continued)

(56) References Cited

U.S. PATENT DOCUMENTS 5,468,110 A * 11/1995 McDonald .......... G07F 17/0092 414/268
6,230,927 B1 * 5/2001 Schoonen ............ A61J 7/0084 700/215
(Continued)

FOREIGN PATENT DOCUMENTS

JP 2021-168791 A 10/2021
JP 2021-168792 A 10/2021
(Continued)

*Primary Examiner* — Jacob S. Scott
*Assistant Examiner* — Temesgen M. Maru
(74) *Attorney, Agent, or Firm* — Duft & Bornsen, PC

(57) ABSTRACT

A medication support device includes a container to store a medicine package in which a plurality of medicines are packed, a pickup device to pick up the medicine package from the container, a conveyor to convey the medicine package picked up by the pickup device, a medicine dispenser including a prescribed position to which the medicine package conveyed by the conveyor is dispensed, a medication-related information reader to read medication-related information including at least a name of a patient who takes medicines and a time of medication, and processing circuitry to control a medicine dispensing operation in which the medicine package picked up from the container is dispensed to the medicine dispenser, based on the medication-related information read by the medication-related information reader, and skip a process with an abnormality and make the medicine dispensing operation continue after the medicine dispensing operation starts.

20 Claims, 45 Drawing Sheets

(58) Field of Classification Search
CPC ................ A61J 2205/10; A61J 2205/30; A61J 2205/60; G07F 9/02; G07F 11/165; G07F 17/0092; G16H 20/10; G16H 20/13; G06Q 10/087; B65G 1/1371
See application file for complete search history.

(56) References Cited

U.S. PATENT DOCUMENTS

| | | | | |
|---|---|---|---|---|
| 7,123,989 | B2 * | 10/2006 | Pinney | G07F 9/026<br>700/216 |
| 7,783,378 | B2 * | 8/2010 | Pinney | G07F 11/62<br>700/242 |
| 9,745,131 | B2 * | 8/2017 | Hawkes | B65G 59/062 |
| 10,964,154 | B2 * | 3/2021 | Einav | A61J 7/0076 |
| 11,551,183 | B2 * | 1/2023 | Cacioppo | G05D 1/0287 |
| 2021/0361532 | A1 * | 11/2021 | Hayashi | A61J 7/0076 |
| 2022/0233406 | A1 | 7/2022 | Kojima et al. | |
| 2023/0096511 | A1 | 3/2023 | Morinaga et al. | |
| 2023/0255853 | A1 | 8/2023 | Fujie et al. | |
| 2023/0255854 | A1 | 8/2023 | Hayashi et al. | |
| 2023/0293391 | A1 | 9/2023 | Yamanaka et al. | |
| 2023/0372203 | A1 | 11/2023 | Niitsuma et al. | |
| 2023/0404855 | A1 | 12/2023 | Yamaya et al. | |

FOREIGN PATENT DOCUMENTS

| | | | | |
|---|---|---|---|---|
| JP | 2023-051361 | A | 4/2023 | |
| WO | WO-2008085673 | A1 * | 7/2008 | B65B 5/103 |

* cited by examiner

FIG. 22

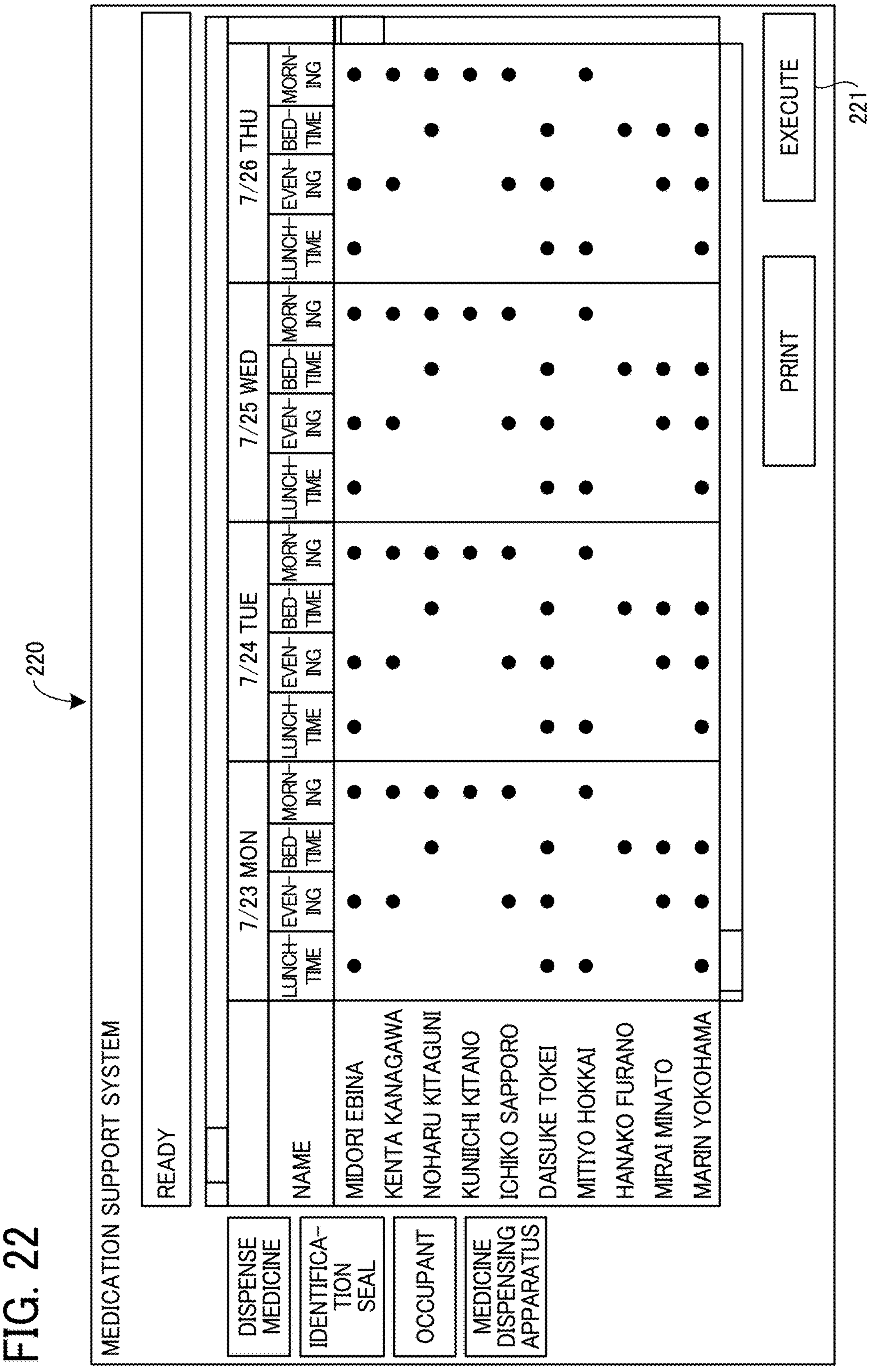

| | 7/23 MON | | | | 7/24 TUE | | | | 7/25 WED | | | | 7/26 THU | | | |
|---|---|---|---|---|---|---|---|---|---|---|---|---|---|---|---|---|
| NAME | LUNCH-TIME | EVEN-ING | BED-TIME | MORN-ING | LUNCH-TIME | EVEN-ING | BED-TIME | MORN-ING | LUNCH-TIME | EVEN-ING | BED-TIME | MORN-ING | LUNCH-TIME | EVEN-ING | BED-TIME | MORN-ING |
| MIDORI EBINA | ● | ● | | ● | ● | ● | | ● | ● | ● | | ● | ● | ● | | ● |
| KENTA KANAGAWA | | ● | | ● | | ● | | ● | | ● | | ● | | ● | | ● |
| NOHARU KITAGUNI | | | ● | ● | | | ● | ● | | | ● | ● | | | ● | ● |
| KUNIICHI KITANO | | | | ● | | | | ● | | | | ● | | | | ● |
| ICHIKO SAPPORO | | ● | | ● | | ● | | ● | | ● | | ● | | ● | | ● |
| DAISUKE TOKEI | ● | ● | ● | | ● | ● | ● | | ● | ● | ● | | ● | ● | ● | |
| MITIYO HOKKAI | ● | | | ● | ● | | | ● | ● | | | ● | ● | | | ● |
| HANAKO FURANO | | | ● | | | | ● | | | | ● | | | | ● | |
| MIRAI MINATO | | ● | ● | | | ● | ● | | | ● | ● | | | ● | ● | |
| MARIN YOKOHAMA | ● | ● | ● | | ● | ● | ● | | ● | ● | ● | | ● | ● | ● | |

MEDICATION SUPPORT DEVICE

CROSS-REFERENCE TO RELATED APPLICATION

This patent application is based on and claims priority pursuant to 35 U.S.C. § 119(a) to Japanese Patent Application No. 2023-175440, filed on Oct. 10, 2023, in the Japan Patent Office, the entire disclosure of which is hereby incorporated by reference herein.

BACKGROUND

Technical Field

The present disclosure relates to a medication support device.

Background Art

In relation to medication support devices, a medicine setting system is known that is used for the purposes of increasing the efficiency of the business operations of pharmacists or the like for setting a medicine package to a medication calendar so as to be ready for use. Such a medicine setting system includes a medicine dispensing device that makes a medicine package containing medicine and dispenses the medicine package, a medicine setting device that sets a medicine package in a medicine setting tool, and a package conveyance unit that conveys the medicine package from the medicine dispensing device to the medicine setting device. In the above system, a medicine package is prepared, and the prepared medicine package is conveyed and supplied to the medicine setting device. Then, the medicine package that has been supplied to the medicine setting device is set to the medicine setting tool.

Moreover, technologies have been proposed that determine whether a medicine package is appropriately dispensed to a medicine dispenser such as a medicine dispensing tray to which medicines to be taken by several persons in a day-care center or nursing home have been dispensed. In such technologies, inappropriately prepared medicine packages are identified when medicines are erroneously dispensed. Accordingly, the length of time required for a use can be shortened, and medication errors such as taking a wrong medicine or forgetting to take a medicine can be prevented. For such purposes, pack data is read by a camera that reads medication-related information before a medicine package is conveyed to a specific position of the medicine dispensing tray, and the read data is compared with the medication-related information to see whether there is a match.

SUMMARY

The present disclosure described herein provides a medication support device including a container to store a medicine package in which a plurality of medicines are packed, a pickup device to pick up the medicine package from the container, a conveyor to convey the medicine package picked up by the pickup device, a medicine dispenser including a prescribed position to which the medicine package conveyed by the conveyor is dispensed, a medication-related information reader to read medication-related information including at least a name of a patient who takes medicines and a time of medication, and processing circuitry to control a medicine dispensing operation in which the medicine package picked up from the container is dispensed to the medicine dispenser, based on the medication-related information read by the medication-related information reader, and skip a process with an abnormality and make the medicine dispensing operation continue after the medicine dispensing operation starts.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

FIG. 22 is another diagram illustrating an example display screen related to an error notification method.

FIG. 36 is a diagram illustrating a display screen provided with a resume key used to execute the next medicine dispensing operation after an error is dealt with.

Figure 1A:
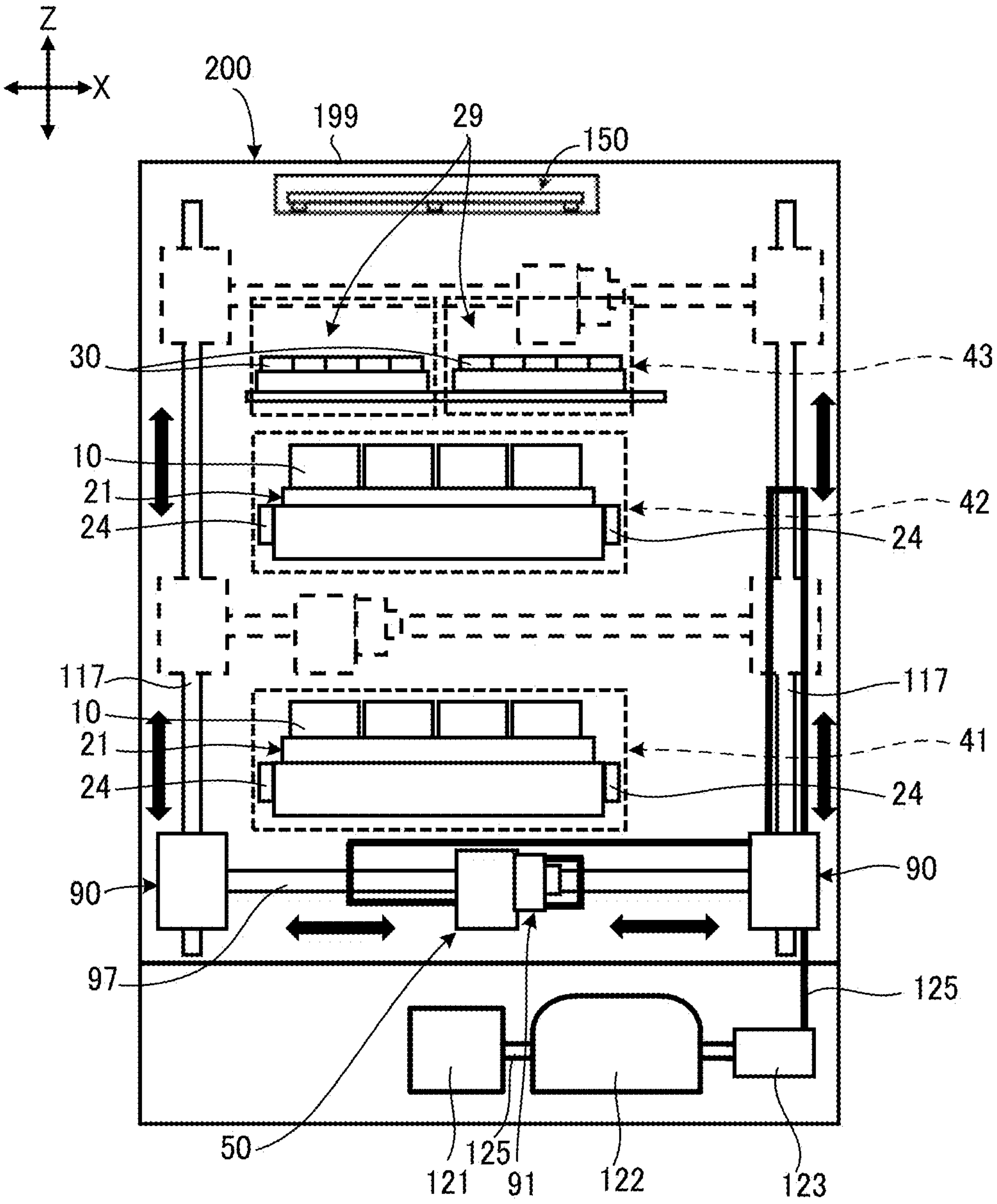
FIG. 1A is a schematic front view of a medicine dispensing apparatus in its entirety, according to a comparative example.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular in embodiments only and is not intended to limit the present disclosure. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing embodiments illustrated in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

Embodiments of the present disclosure and examples of the present disclosure are described below in detail with reference to the accompanying drawings. In the drawings and the description of the embodiments and examples of the present disclosure, like reference signs denote like elements such as members or components of similar shapes or similar functionality, and overlapping description may be omitted where appropriate unless there is concern about the possibility of confusion.

FIG. 1A is a schematic front view of a medicine dispensing apparatus 200 in its entirety, according to a comparative example.

Figure 1B:
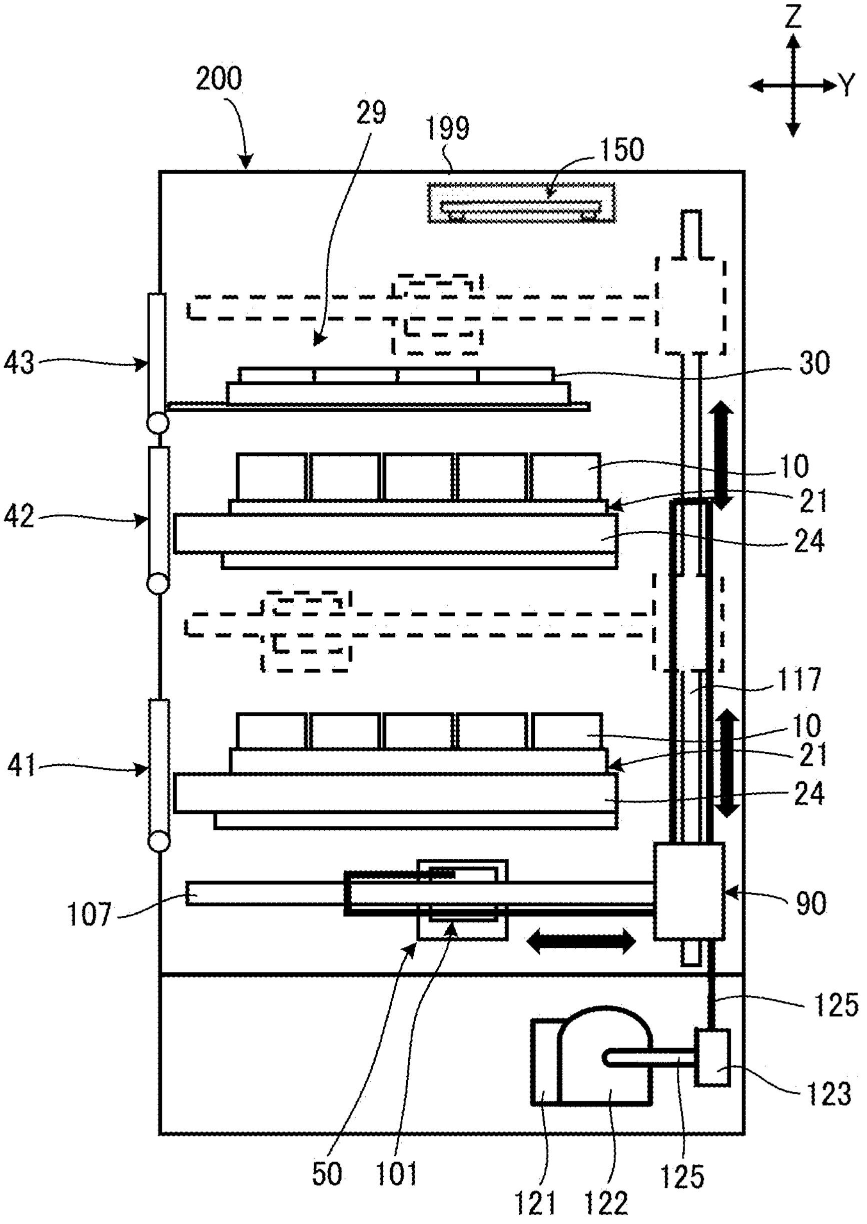
FIG. 1B is a side view of the medicine dispensing apparatus of FIG. 1A.

FIG. 1B is a schematic side view of the medicine dispensing apparatus 200 of FIG. 1A.

As illustrated in FIG. 1A and FIG. 1B, the medicine dispensing apparatus 200 is provided with a cartridge 10 that is also referred to as a container, a medicine dispensing tray 30, a pickup device 50, a conveyor 90, and a first gate 41 to a third gate 43.

In FIG. 1A, the horizontal direction or the right and left directions of the medicine dispensing apparatus 200 is defined as an X-axis direction, where the horizontal direction or the right and left directions of the medicine dispensing apparatus 200 is also referred to as the width direction of the medicine dispensing apparatus 200. Moreover, the front-rear direction or the depth direction of the medicine dispensing apparatus 200 as illustrated in FIG. 1B is defined as a Y-axis direction, and the up and down directions or the orthogonal direction of the medicine dispensing apparatus 200 is defined as a Z-axis direction, where the up and down directions or the orthogonal direction of the medicine dispensing apparatus 200 is also referred to as the vertical direction.

Each one of the cartridges 10 serves as a first container in which medicine packages 2 packing several kinds of medicines 3 as will be described later are stored upon being stacked on top of each other in layers. The medicine package 2 may be referred to simply as a pack or a medicine pack, and the first container may be referred to simply as a container in the following description. The expression "stored upon being stacked on top of each other in layers" in the present disclosure indicates keeping the packs horizontally in such a manner that the front face is viewable.

The multiple cartridges 10 are placed in a pair of drawers 21 arranged at the lowermost portion and middle portion of a housing 199 of the medicine dispensing apparatus 200. In the case of the medicine dispensing apparatus 200 as illustrated in FIG. 1A and FIG. 1B, twenty cartridges 10 (4×5=20) are placed and held in one of the drawers 21 (see FIG. 5). Each of the pair of drawers 21 serves as a second container in which at least one of the multiple cartridges 10 is placed and held.

Each of the multiple cartridges 10 is placed and housed in a partitioned lattice-like side wall and bottom wall in the drawer 21. On the bottom wall of the drawer 21 of corresponding ones of the multiple cartridges 10, a rectangular through an opening 21*a* through which a pack can be picked up from below one of the multiple cartridges 10, making use of the elasticity or free deformation of the pack as will be described later in detail in relation to the operation, is formed (see FIG. 5).

Each one of the multiple medicine dispensing trays 30 is an example of a medicine dispenser or medicine dispensing table in which the prescribed packs conveyed by the conveyor 90 are arranged. In the present embodiment described with reference to FIG. 1A and FIG. 1B, two medicine dispensing trays 30 each of which has twenty (=4×5) rooms 33 are arranged. The areas that include the medicine dispensing trays 30 where the packs are passed to the medicine dispensing tray 30 for automatic medicine dispensing are referred to as medicine dispensing areas 29 in the following description.

The pickup device 50 is an example of a pickup device that picks up a specific one of the medicine packs from the cartridge 10.

The conveyor 90 is an example of a conveyor that conveys the pack picked up from one of the cartridges 10 using the pickup device 50.

Each of the first gate 41 and the second gate 42 is an example of an entrance and exit gate for the container, which allows one of the multiple cartridges 10 to enter and exit the housing 199. The multiple cartridges 10 are inserted and set in the housing 199 through each one of the first gate 41 and the second gate 42. The open and close door of one of the first gate 41 and the second gate 42 are opened, and the drawer 21 in which the multiple cartridges 10 are aligned is drawn out to the front side. By so doing, the cartridges 10 are inserted or withdrawn.

The third gate 43 according to the present comparative example serves as an entrance and exit gate for the medicine dispenser, which allows one of the multiple medicine dispensing trays 30 to enter and exit the housing 199. The second gate 42 and the third gate 43 are arranged such that the packs can be taken out immediately after the packs are set or inserted into the medicine dispensing tray 30.

As illustrated in FIG. 1A, the medicine dispensing apparatus 200, two medicine dispensing trays 30 are arranged as described above, and as will be described later in detail, the medicine dispensing trays 30 are arranged for each time of medication such as a time in the morning, a time in the daytime, a time in the evening, and a time before going to bed.

The third gate 43 for the medicine dispensing tray 30 is also arranged for each one of the medicine dispensing trays 30. Due to such a configuration, another different one of the medicine dispensing trays 30 can be taken out even when the medicine dispersing operation is performed on a particular one of the multiple medicine dispensing trays 30.

The drawers 21 of the multiple cartridges 10 as illustrated in FIG. 1A and FIG. 1B are arranged in two stages on the upper and lower sides under the medicine dispensing trays 30. However, no limitation is intended thereby, and the drawers 21 may collectively be arranged on the upper side or the lower side. Depending on the number of persons in the day-care center or nursing home, the multiple cartridges 10 may be arranged in three stages.

Figures 2A, 2B, 2C, 2D:
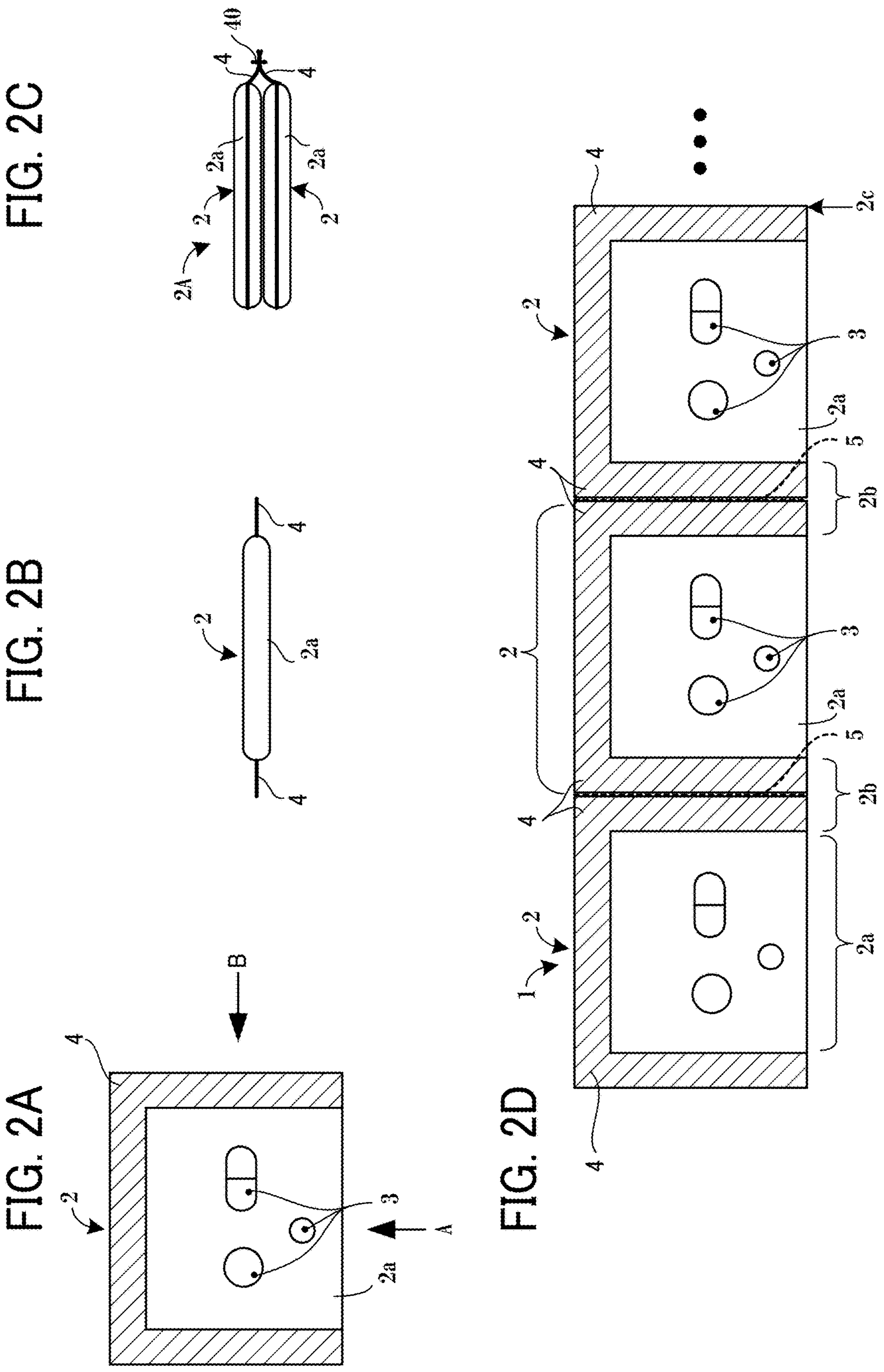
FIG. 2A is a typical plan view of a single medicine package.
FIG. 2B is a side view of the single medicine package of FIG. 2A viewed in a direction indicated by an arrow A.
FIG. 2C is a side view of bound medicine packages viewed in a direction indicated by an arrow B.
FIG. 2D is a diagram illustrating a typical form of continuous packs.

FIG. 2A is a typical plan view of a single medicine package 2.

FIG. 2B a side view of the single medicine package 2 of FIG. 2A viewed in a direction indicated by an arrow A.

FIG. 2C is a side view of bound medicine packages 2A viewed in a direction indicated by an arrow B, where such bound medicine packages 2A are obtained by combining the multiple medicine packages 2.

FIG. 2D is a diagram illustrating a typical form of continuous packs 1.

The medicine pack includes the single medicine package 2 and bound medicine packages 2A in which multiple medicine packages 2 are stacked on top of each other in layers and bound by a stapler or the like. In FIG. 2C, two medicine packages 2 are bound as the bound medicine packages 2A. Except for FIG. 2A to FIG. 2D, a single medicine package 2 is illustrated. However, as a matter of course, the bound medicine packages 2A is also included even when only a single medicine package 2 is illustrated.

As illustrated in FIG. 2A, one medicine package 2 is formed of, for example, a resin film, and medicines 3 such as capsules or tablets are packed in small quantities. The medicine package 2 includes a bag 2*a* that covers the medicines 3 and a pressure-bonded portion 4 in which three sides of the bag 2*a* are pressure-bonded or welded. The pressure-bonded portion 4 is hatched in FIG. 2A and FIG. 2D. Typically, the side of the medicine package 2 on the bag 2*a* side is folded into two, and the medicines 3 are packed therebetween. The pressure-bonded portion 4 forms a leakage-preventing portion that prevents the medicines 3 from slipping out from the bag 2*a*. Typically, the medicines 3 in one medicine package 2 is a one-time dosage for a patient who takes medicines.

The medicine package 2 is dispensed and prepared by a drug-dispensing machine installed in, for example, a pharmacy. The dispensing sheets that are used for dispensing the medicines are rolled long-length sheets, and are perforated between packs. The dispensing sheets are rolled in an overlapping manner, and the medicines 3 to be taken are packed in the space between the sheets. The medicines 3 for a required number of doses are divided into small quantities, and packed into the multiple medicine packages 2 that form a continuous sheet. The three sides other than the folded portion of each one of the multiple medicine packages 2 around the medicines 3 for a single dose are sealed in turn by the pressure-bonded portion 4. The multiple medicine packages 2 that form such a continuous sheet may be referred to as continuous packs 1 in the following description. In the continuous packs 1 that are described with reference to FIG. 2D, the multiple medicine packages 2 are coupled to each other and laid like a belt. In the present embodiment described with reference to FIG. 2D, the medicines 3 for three doses are illustrated. The continuous packs 1 are a typical form of drug or medicine that is given or sold at a pharmacy or the like to, for example, a user such as a person who actually takes the medicine 3 in the medicine package 2 and a personal care attendant or assistant who helps or assists the user to take medication, or a staff or the like including a pharmacist, a nurse practitioner, a care manager, or a medication assistant of, for example, various kinds of day-care center, nursing home, or medical institution. For the sake of explanatory convenience, each one of the packs is filled with the medicines 3 of the same form in the following description. In FIG. 2C, by way of example, each one of the packs is filled with the same capsule and the same tablets. However, no limitation is indicated thereby. As a matter of course, each one of the packs may be filled with different types of medicines depending on, for example, the usage or purposes of the medication.

In the present embodiment described with reference to FIG. 2A to FIG. 2D, the medicine package 2 has a rectangular shape in a plan view, and a packaging method in which three sides are crimped and sealed as in the present embodiment is called three-sided packaging in the related art. Most of the drug-dispensing machines available on the market make packs using the three-sided packaging method.

The pressure-bonded portion 4 has a band-like width of about 10 to 15 millimeters (mm), and has higher rigidity than the portion of the bag 2*a* that is a transparent or semitransparent film where the medicines 3 can be visually recognized therethrough. A boundary portion 2*b* that is implemented by perforation 5 is formed in the center of the pressure-bonded portion 4 between a pair of the multiple medicine packages 2 making up the continuous packs 1. The multiple medicine packages 2 are adjacent to each other in an upstream-to-downstream direction. For example, a user who is not handicapped in the hand can obtain one medicine package 2 by tearing off at the perforation 5 by hand or by cutting near the perforation 5 with scissors or a dedicated cutter.

As illustrated in FIG. 2C, the bound medicine packages 2A may be used. The bound medicine packages 2A is formed by fastening medicine packages 2 at the center of the three sides of the pressure-bonded portions 4 by stapling 40 or the like. In FIG. 2C, two medicine packages 2 are fastened together.

Figure 3:
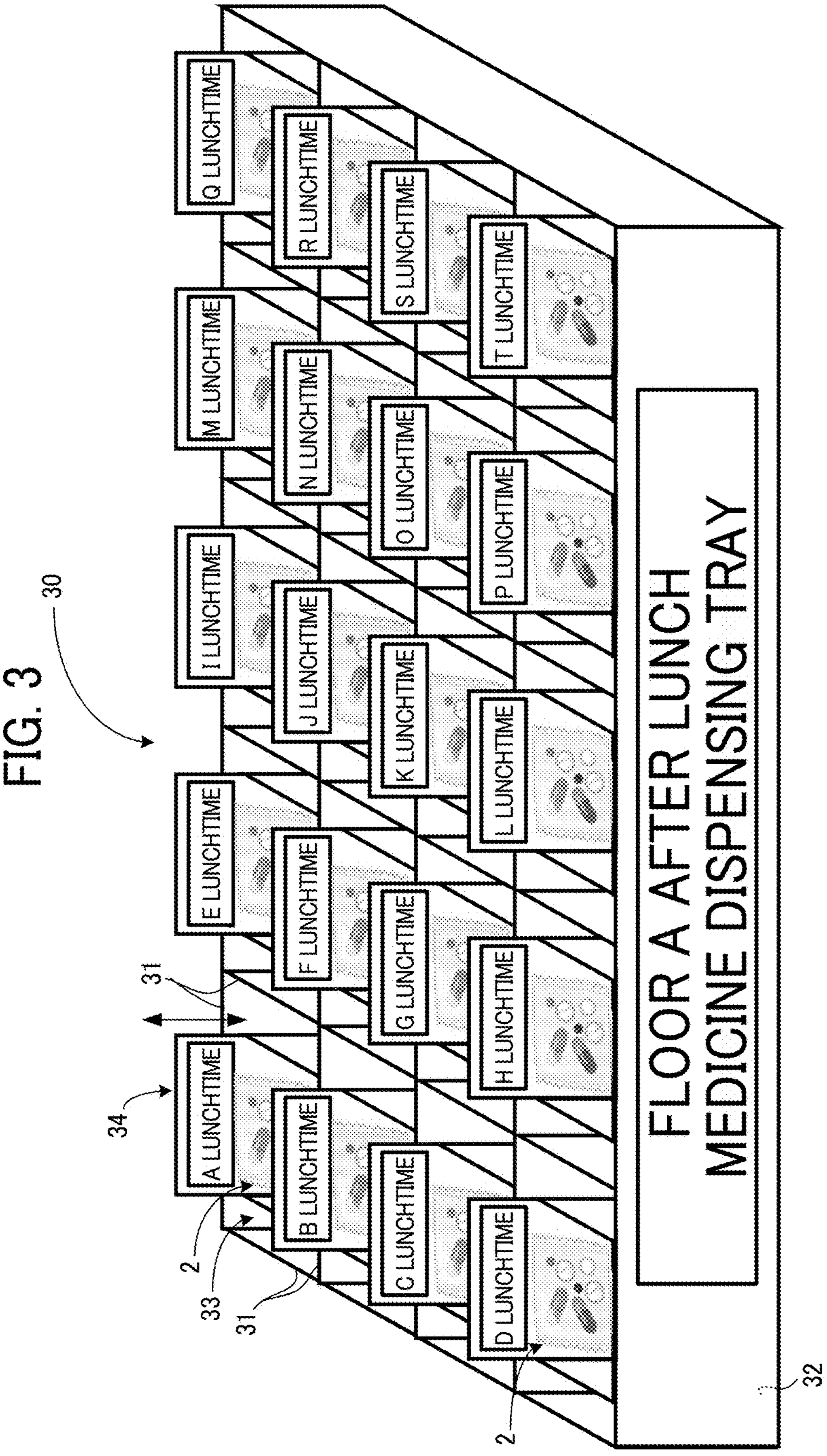
FIG. 3 is an external perspective view of a medicine dispensing tray.

FIG. 3 is an external perspective view of the medicine dispensing tray 30.

As illustrated in FIG. 3, each one of the multiple medicine dispensing trays 30 has partition walls 31 that serve as a plurality of dividers for arranging prescribed packs, and is partitioned by four upright partition walls 31. The twenty rooms 33 that are formed in each one of the multiple medicine dispensing trays 30 can be expressed as the components of a matrix including five columns in the X-axis direction or the line feed direction and four rows in the Y-axis direction or the character feed direction. As a result, each one of the twenty rooms 33 of the medicine dispensing trays 30 can be uniquely positioned based on the components and addresses of the matrix of five columns and four rows. Furthermore, each one of the multiple medicine dispensing trays 30 has a bottom wall 32 on which the multiple medicine packages 2 are placed. As described above, each one of the medicine dispensing trays 30 is arranged such that a specific one of the multiple packs arranged in a specific one of the rooms 33 will be placed in a specific one of the rooms 33 with reliability by the multiple partition walls 31, which are four partition walls in the present embodiment, and the bottom wall 32 in common, without being mixed up with packs in different one of the rooms 33 or dropping off from the bottom wall 32.

The medicine dispensing tray 30 illustrated in FIG. 3 includes the twenty rooms 33 that serve as a group of medicine dispensers as a whole and subdivision boxes 34 that serve as individual medicine dispensers detachable from the rooms 33. For example, the multiple subdivision boxes 34 hold the multiple medicine packages 2 filled with the medicines 3 to be taken by twenty residents A to T after lunch in a day-care center or nursing home. In other words, one of the multiple medicine dispensing trays 30 illustrated in FIG. 3 is used to arrange prescribed packs in a predetermined or specific one of the multiple rooms 33 partitioned by dividers through the multiple subdivision boxes 34.

In each one of the multiple rooms 33 of the multiple medicine dispensing trays 30, a setting position or inserting position is determined for each patient who takes medicines depending on the type of medicines in the pack to be taken. In other words, the multiple rooms 33 in one of the multiple medicine dispensing trays 30 may be allocated to patients who take medicines at the same time. In a case where a specific patient who is to take medicines does not take a medicine at a specific time of medication, arrangement can be made such that a pack is not given to such a specific patient at the specific time of medication.

However, no limitation is intended by the medicine dispensing trays 30 described above. Each one of the multiple rooms 33 of one of the medicine dispensing trays 30 may be allocated for each time of medication of each patient who takes medicines. More specifically, in such an alternative embodiment of the present disclosure, the multiple rooms 33 may be allocated to each of the patients who take medicines in view of the time of medication of each one of the multiple medicine packages 2 to be taken in the morning, in the daytime, in the evening, or before going to bed. The medicine dispensing trays 30 of such cases may be managed on a room-by-room basis or a floor-by-floor basis in day-care centers or nursing homes where patients who take medicines reside, and the multiple medicine packages 2 for that day or a couple of days may be dispersed in advance to the multiple medicine dispensing trays 30.

According to the above alternative embodiment, allocating the rooms 33 based on each time of medication such as a time in the morning, a time in the daytime, a time in the evening, and a time before going to bed can prevent the time of medication from being mistaken by patients who take medicines. The configuration or structure of the multiple medicine dispensing trays 30 is not limited to the embodiments of the present disclosure described above, and various kinds of combinations are theoretically possible between patients who take medicines and the timing at which the medicines are to be taken. However, such combinations may go beyond the scope of the present disclosure, the description of such combinations is omitted.

Figure 4A:
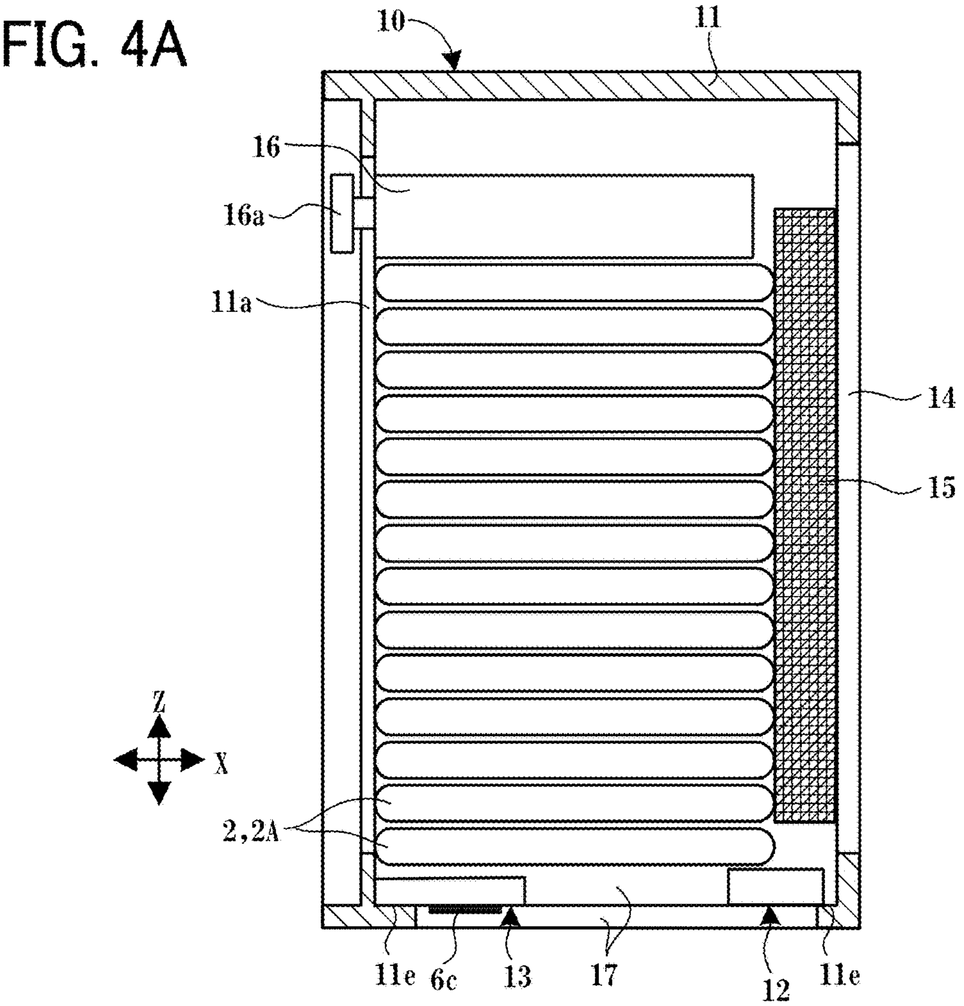
FIG. 4A is a vertical sectional view of a cartridge.

FIG. 4A is a vertical sectional view of the cartridge 10.

Figure 4B:
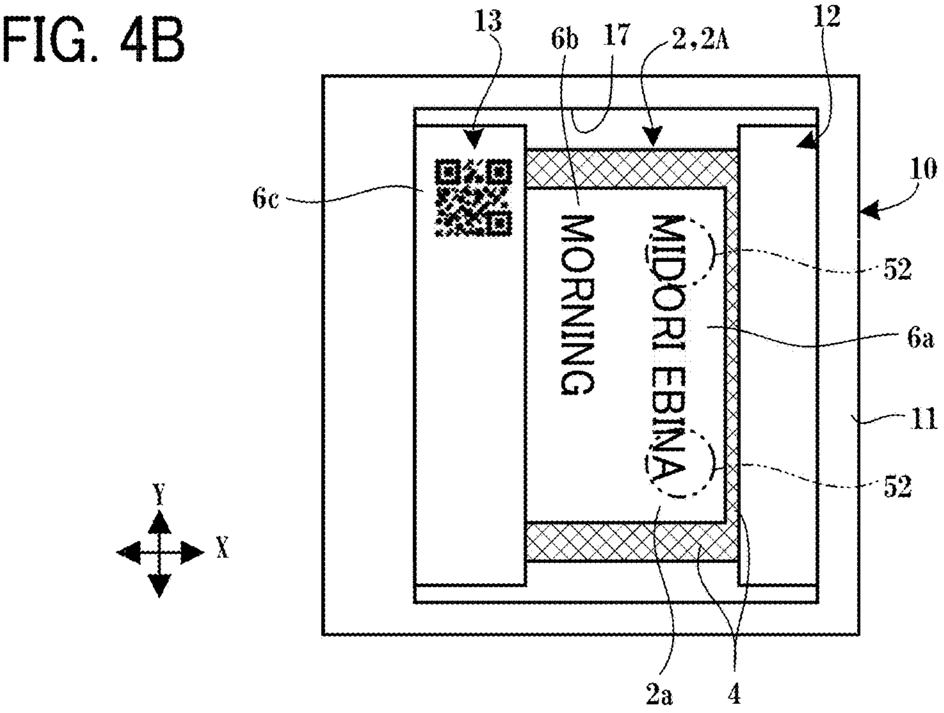
FIG. 4B is a bottom view of the cartridge of FIG. 4A.

FIG. 4B is a bottom view of the cartridge 10 of FIG. 4A.

For example, each one of the multiple cartridges 10 includes a casing 11, a lid 14, a pack pickup slot 17, a movable board 16, a pack posture keeper 15, and a right support portion 12 and a left support portion 13 each of which serves as a support portion.

The casing 11 stores, for example, multiple medicine packages 2 or the bound packages 2A. In the following description, a single medicine package 2 will represent such multiple medicine packages 2 or bound packages 2A. For example, the casing 11 is integrally or separately formed using resin.

The lid 14 enables the multiple medicine packages 2 to be loaded or unloaded.

The pack pickup slot 17 is formed in a lower portion or a bottom portion of the casing 11, and is used to pick up the medicine package 2 in one of the multiple cartridges 10. Moreover, the pack pickup slot 17 allows the medicine package 2, which is picked up from one of the multiple cartridges 10 by the pickup device 50 (see, for example, FIG. 1A, FIG. 1B, FIG. 7A, and FIG. 7B), to pass therethrough.

The movable board 16 prevents the medicine package 2 from falling out, and moves the lowermost one of the medicine packages 2 to a position close to the pack pickup slot 17 after the first one of the maximum number of medicine packages 2 that can be stored in the casing 11 is picked up.

The pack posture keeper 15 keeps the posture of the medicine package 2.

The right support portion 12 and the left support portion 13 also support or hold the medicine package 2 in the casing 11.

In the present comparative example, the to-be-picked-up portion of one of the multiple medicine packages 2 to be picked up from one of the multiple cartridges 10 by the pickup device 50 is at a lower portion or bottom portion of the corresponding one of the multiple cartridges 10. In other words, the to-be-picked-up portion includes the pack pickup slot 17, and the right support portion 12 and the left support portion 13 that serve as a pair of support portions or supporting member and support, at multiple points, one of the multiple medicine packages 2 to be picked up from one of the multiple cartridges 10.

When one of the multiple medicine packages 2 is picked up from one of the multiple cartridges 10 by the pickup device 50, the right support portion 12 and the left support portion 13 allow one of the multiple medicine packages 2 to pass through. On the other hand, when any one of the multiple medicine packages 2 is not to be picked up from one of the multiple cartridges 10, the right support portion 12 and the left support portion 13 restrict the passage of one of the multiple medicine packages 2 to store and hold the multiple medicine packages 2 in the casing 11.

As described above, the right support portion 12 and the left support portion 13 support or hold the medicine packages 2 in the cartridge 10, and each one of the right support portion 12 and the left support portion 13 is fixed and immovable such that one of the multiple medicine packages 2 can be picked up in a stable manner from one of the multiple cartridges 10 by the pickup device 50.

The right support portion 12 and the left support portion 13 are a pair of fixation members that are fixed or attached to the pair of bottom-wall inner surfaces 11*e* of the right bottom-wall edge and left bottom-wall edge of the pack pickup slot 17, respectively.

As illustrated in FIG. 4B, the pack pickup slot 17 has a function to allow the pair of suction pads 52 of the pickup device 50, each of which serves as an air suction unit or suction unit, to pass therethrough in order to pick up one of the multiple medicine packages 2, and has a function to let the medicine package 2 that is picked up and the pair of suction pads 52 to pass through.

In one of the multiple cartridges 10 illustrated in FIG. 4B, a pair of positions at which the pair of suction pads 52 adsorb or suck up one of the multiple medicine packages 2 stored in one of the multiple cartridges 10, are indicated by a pair of ring-shaped dot-dot-dash lines. Such a pair of positions may be referred to as a pair of suction-pad positions in the following description.

The right support portion 12 and the left support portion 13 support the multiple medicine packages 2 in one of the multiple cartridges 10 such that the multiple medicine packages 2 in one of the multiple cartridges 10 do not fall off from the pack pickup slot 17. As will be described later in detail in regard to the operation of the pickup device 50, when the medicine package 2 at the bottom of the cartridge 10 is sucked and picked up by the pair of suction pads 52, one of the multiple medicine packages 2 is sucked by the pair of suction pads 52 at two suction-pad positions in the Y-axis direction near both ends of the right support portion 12. When the lowermost one of the medicine packages 2 is picked up from one of the multiple cartridges 10 by the pair of suction pads 52, the pair of suction pads 52 pass near both ends of the right support portion 12 in the Y-axis direction to suck and hold one of the medicine packages 2.

As illustrated in FIG. 4B, two points at which the suction pad 52 contacts are arranged near both ends of the right support portion 12 in the Y-axis direction. Due to such a configuration, the possibility of an error in which the suction by the pair of suction pads 52 is disabled can be avoided and prevented, and the picking up operation can successfully be done. In other words, the medicine package 2 is sucked and adhered to the pair of suction pads 52 at both ends in the Y-axis direction, and the bag 2*a* of the medicine package 2, which is made of film, is stretched and can withstand the deformation. Accordingly, both reliable support or holding of the multiple medicine packages 2 in one of the multiple cartridges 10 and smooth removal of one of the multiple medicine packages 2 can be achieved.

As illustrated in FIG. 4A, the types of the multiple medicine packages 2 in one of the multiple cartridges 10 are sorted or divided based on the timings at which medicines are taken. For example, one cartridge contains medicines to be taken in fourteen days in the morning by Mr. or Ms. A. In view of the above circumstances, if Mr. or Ms. A takes the medicines not only in the morning but also in the daytime or in the evening, or before going to bed, four cartridges 10 are required in total.

However, no limitation is indicated thereby. For example, in an alternative embodiment of the present disclosure, a single cartridge 10 may be prepared for each person or patient who takes medicines. In such cases, for example, a pack to be used in the morning on day one, a pack to be used at lunchtime on day one, a pack to be used in the evening on day one, a pack to be used before going to bed on day one, a pack to be used in the morning on day two, a pack to be used at lunchtime on day two, and a pack to be used in the evening on day two may be stored in the order listed upward from the pack pickup slot 17 parallel to the direction in which packs are taken out from the multiple cartridges 10.

In the present comparative example, the right support portion 12 and the left support portion 13 are fixed to the bottom-wall inner surface 11*e* of the pack pickup slot 17 of the casing 11 such that one of the multiple medicine packages 2 can be picked up in a stable manner from one of the multiple cartridges 10 by the pickup device 50.

In other words, the right support portion 12 and the left support portion 13 are fixed when the right support portion 12 and the left support portion 13 hold both ends of the medicine pack such as the medicine package 2 or the bound medicine packages 2A around the pack pickup slot 17 arranged at the lower portion of one of the multiple cartridges 10.

The medicine package 2 that is stored in the cartridge 10 is supported by a right support portion 12 and a left support portion 13 so as not to drop. The right support portion 12 supports a right end where the medicine package 2 is sucked up, and the left support portion 13 supports a left end on the other side.

The right support portion 12 and the left support portion 13 are different in the length of the portion that support the multiple medicine packages 2, and the length of portion of the right support portion 12 that support the multiple medicine packages 2 is shorter than that of the left support portion 13. As will be described later in detail with reference to FIG. 8C, when the lowermost one of the multiple medicine packages 2 stored in the cartridge 10 is adsorbed or sucked by the pair of suction pads 52 and is pulled out from the cartridge 10, the medicine pack is bent due to its elasticity. Accordingly, the medicine pack can easily be pulled out.

In such a configuration, the pair of support portions including the right support portion 12 and the left support portion 13 are of fixed type. Accordingly, the front end of the next one of the multiple medicine packages 2 to be taken out can be reliably held and does not jump out or fall off together with one of the multiple medicine packages 2 that is being taken out. As the pair of support portions including the right support portion 12 and the left support portion 13 do not swing or rotate, the medicine package 2 are held with high stability with no deformation or the like due to unintentional nipping or pressing in the returning operation.

As illustrated in FIG. 4B, medication-related information such as the name of a patient who takes medicines and timing of medication is added onto the surface of the bag 2*a* of the medicine package 2 stored in the cartridge 10. As illustrated in FIG. 4B, more specifically, as the medication-related information, medication-related information 6*a* in which the name of a patient who takes medicines such as the medicine 3 in the medicine package 2 is expressed in texts, and medication-related information 6*b* in which the times of medication at which the medicine 3 is taken is expressed in texts are added onto the surface of the bag 2*a* of the medicine package 2 by printing or the like. When the medicine 3 in the medicine package 2 stored in the cartridge 10 is to be taken by the same person, as illustrated in FIG. 4B, for example, medication-related information 6*c* in which the name of a patient who takes medicines and the times of medication are expressed by a quick response code (QR CODE) may be added to the bottom face of the left support portion 13 or a bottom-wall inner surface 11*e* of the pack pickup slot 17.

The medication-related information 6*a* and the medication-related information 6*b*, which is textual information, are added to the medicine package 2 illustrated in FIG. 4B. However, no limitation is intended thereby, and the medication-related information 6*a* and 6*b*, which is textual information, and the medication-related information 6*c*, which is a quick response code (QR CODE), may be added to the medicine package 2. In other words, the medication-related information includes at least one of the name of a patient who takes medicines, the times of medication at which the medicines in a pack are to be taken, and the number of tablets and types of the medicines prescribed in the pack.

Figure 5:
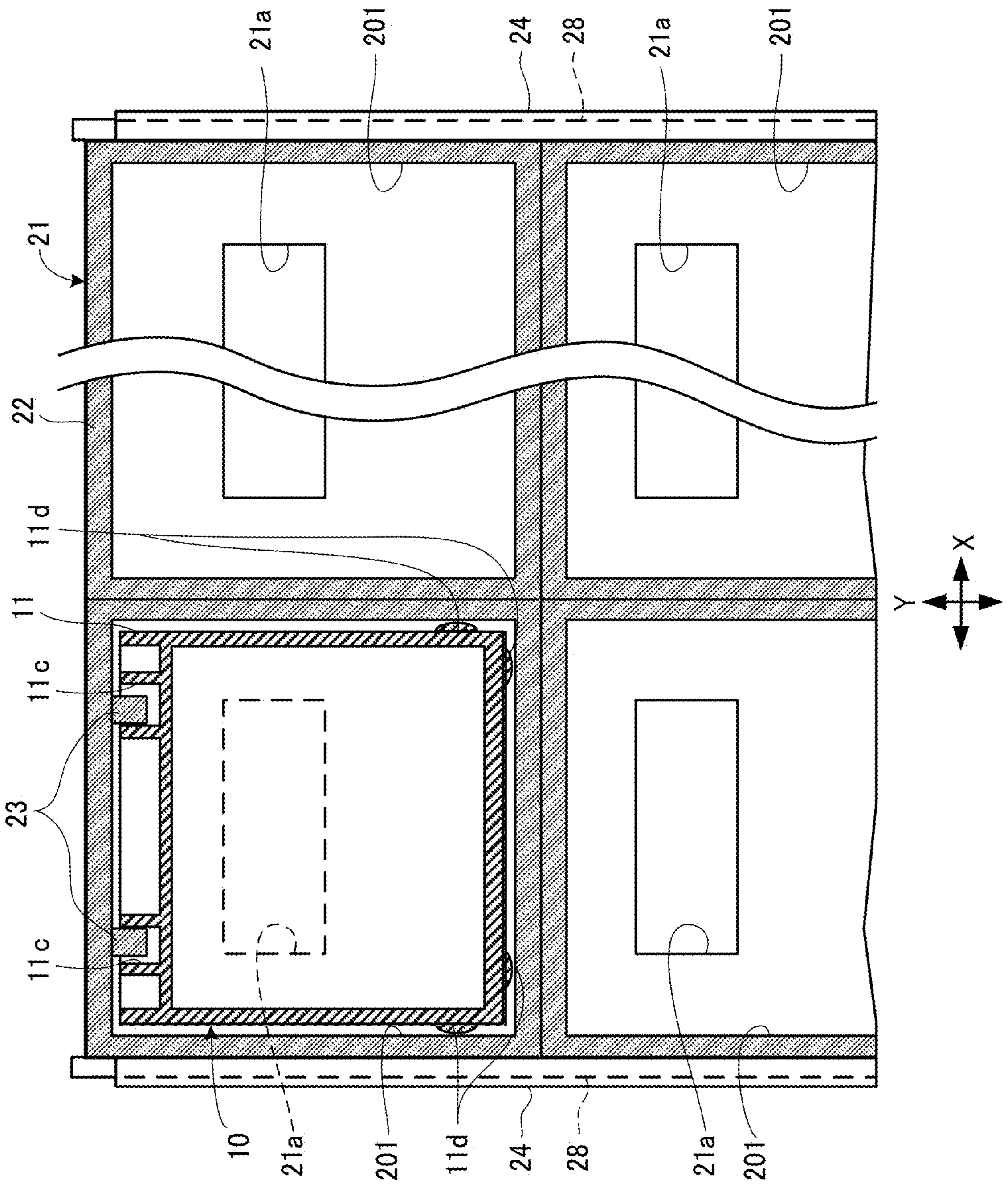
FIG. 5 is a schematic plan sectional view of the attaching and detaching mechanisms for a cartridge.

FIG. 5 is a schematic plan sectional view of the attaching and detaching mechanisms for the container, which are arranged on the drawer 21.

Figure 6:
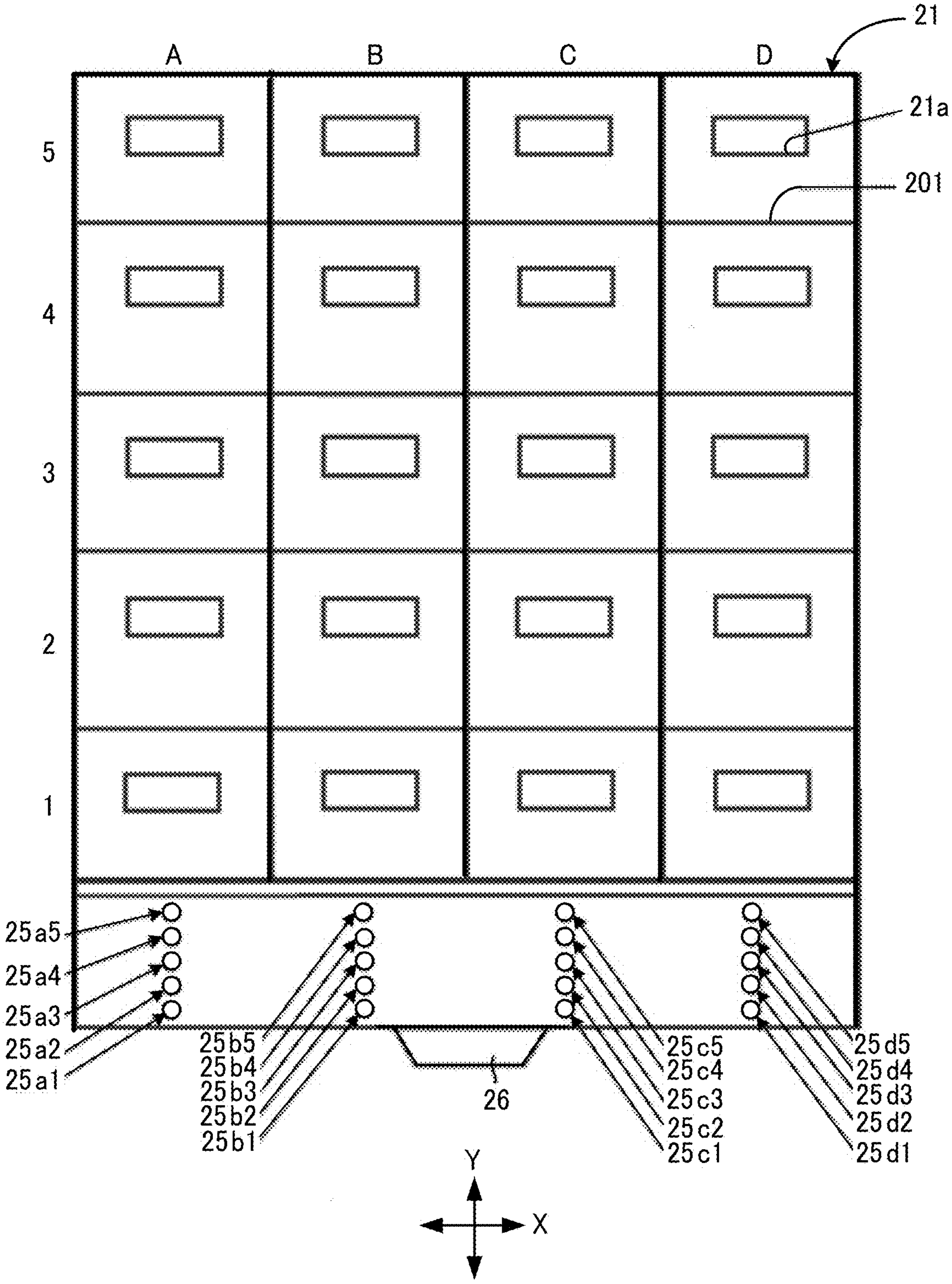
FIG. 6 is a plan view of a cartridge, illustrating the mechanisms for recognizing the cartridge.

FIG. 6 is a schematic plan view of containers and illustrates the mechanisms for recognizing each one of the containers, which are arranged in the drawer 21.

As illustrated in FIG. 5, multiple cartridges 10 can be attached to or detached from the drawer 21. The casing 22 of the drawer 21 is provided with a pair of slide rails 24 on the right and left outer side walls, respectively, and the pair of slide rails 24 are slidable with a pair of rails 28 provided for the housing 199 (see FIG. 1A and FIG. 1B). Due to such a configuration, the drawer 21 can be attached or detached by being pulled out from the housing 199 (see FIG. 1A and FIG. 1B) through the engagement between the pair of slide rails 24 and the rails 28 of the housing 199.

As illustrated in FIG. 5, the cartridge 10 is attached to and detached from the drawer 21 through the engagement and disengagement between a pair of concave portions 11*c* on the external wall of the casing 11 of the cartridge 10 and a pair of convex portions 23 that are formed on the inner wall of the casing 22 of the drawer 21 and protrude inwardly and the engagement and disengagement between the inner wall of the casing 22 and four hemispherical protrusions 11*d* on the external wall of the casing 11. With the above-described attaching and detaching mechanism of the drawer 21, the multiple cartridges 10 can be attached or detached easily and with good operability.

In the above embodiments of the present disclosure, attachment and detachment are enabled by the coupling or engagement of concave and convex portions. However, no limitation is intended thereby, and an elastic member may be arranged in the gap between the inner wall of the casing 22 and the external wall of the casing 11 to enable attachment and detachment. Alternatively, a configuration or structure using magnetic force or a snap-fit assembly method may enable attachment and detachment.

As illustrated in FIG. 6, the drawer 21 has multiple containers 201 in which twenty cartridges 10 are stored. Each of the containers 201 has four columns of A to D in the horizontal direction, and has five rows of 1 to 5 in the vertical direction. The drawer 21 has a grip 26 that is held by hand to insert or withdraw the drawer 21, and information display devices such as light-emitting diodes (LEDs) 25*a*1 to 25*d*5 are arranged near the grip. Due to such a configuration, the arrangement of the multiple cartridges 10 can easily be figured out. More specifically, due to such a configuration, at what position the cartridge 10 in focus is placed in the drawer 21 can easily be figured out at a glance. In FIG. 6, the light-emitting diode (LED) 25*a*1 is used to detect the presence or absence of one of the multiple cartridges 10 attached to or detached from a container A1 of the drawer 21. The container A1 indicates an area or partition that is uniquely determined in the vertical columns and horizontal rows. In a similar manner to the above, the LED 25*a*2 corresponds to the site of a container A2 of the drawer 21, and the LED 25*a*3 corresponds to the site of a container A3 of the drawer 21. Moreover, the LED 25*a*4 corresponds to the site of a container A4 of the drawer 21, and the LED 25*a*5 corresponds to the site of a container A5 of the drawer 21. In a similar manner to the above, as illustrated in FIG. 6, each one of three columns of B to D and five rows of 1 to 5 of the containers is provided with an LED that indicates whether one of the multiple cartridges 10, which is attached to and detached from one of the multiple containers, is present.

When multiple information display devices such as the multiple LEDs 25*a*1 to 25*d*5 are used, for example, a staff who is an operator to attach one of the multiple cartridges 10 to a container 201 may mistake the lighting portion of the LEDs 25_a_1 to 25_d_5. In such cases, the cartridge 10 may erroneously attached to a wrong storage unit other than desired one of the multiple containers 201. In order to handle such a situation, for example, whether the cartridge 10 is present may electrically or automatically be recognized by arranging a plurality of detection units such as sensors or switches at the multiple containers 201 in place of multiple information display devices such as the multiple LEDs 25_a_1 to 25_d_5.

The container may be provided with for example, a number, a bar code, a quick response code (QR CODE), or a non-contact integrated circuit (IC) tag such that each one of the containers will be identifiable. It is desired that the system be programmed to remember what container stores whose medicines. Subsequently, the drawer 21 to which the multiple containers are attached is set in the housing 199 of the medicine dispensing apparatus 200, and each one of the multiple containers is identified by the medicine dispensing apparatus 200. Due to such a configuration, a desired pack can be picked up in the medicine dispensing apparatus 200 without causing any errors.

Figure 7A:
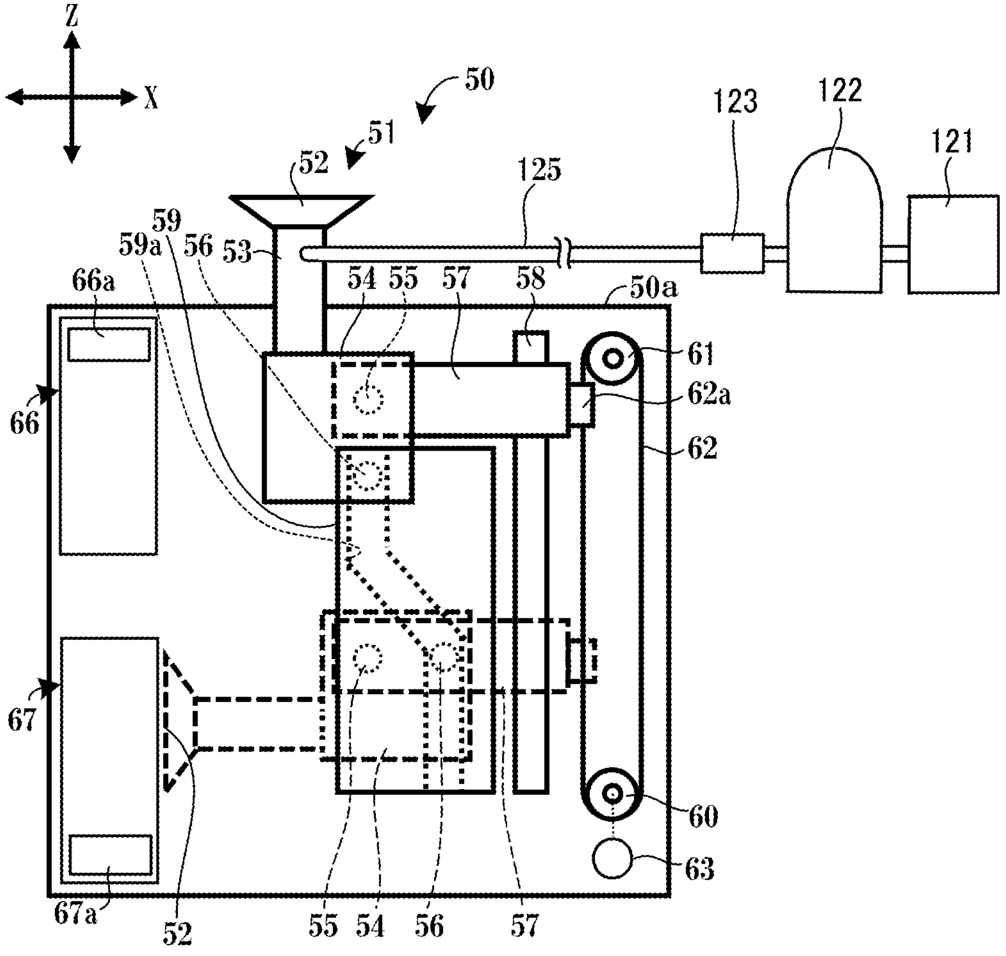
FIG. 7A is a front view of a pickup device, illustrating a configuration or structure of the pickup device.

FIG. 7A is a front view of the pickup device 50, illustrating a configuration or structure of the pickup device 50.

Figure 7B:
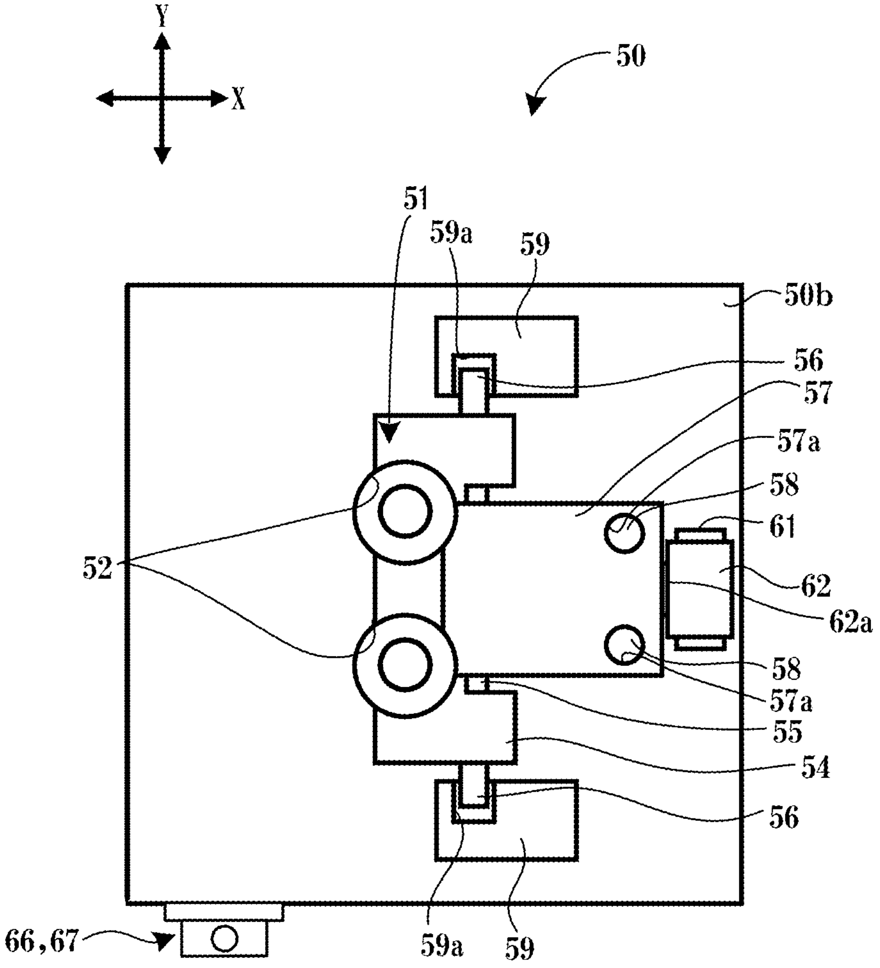
FIG. 7B is a plan view of the pickup device illustrated in FIG. 7A.

FIG. 7B is a plan view of the pickup device 50 illustrated in FIG. 7A.

FIG. 8A to FIG. 9B are front views of the pickup device 50, illustrating the progression of the operation of the pickup device 50.

As illustrated in FIG. 7A and FIG. 7B, the pickup device 50 includes a suction device 51 that is an example of a suction unit to pick up and hold one of the multiple medicine packages 2 from one of the multiple cartridges 10. As illustrated in FIG. 7A and FIG. 7B, the suction device 51 sucks up one of the multiple medicine packages 2 as the vacuum ejector valve 123, which may be referred to as a negative-pressure generator, transforms the positive pressure from the compressor 121 into negative pressure. The compressor 121 is installed outside the conveyor 90, and is coupled to the suction device 51 through the regulator 122 and the vacuum ejector valve 123 by a member for communication such as an air duct 125.

The air duct 125 is arranged together with, for example, a CABLEVEYOR and a wire harness so as not to be stretched even when the pickup device 50 moves inside the medicine dispensing apparatus 200. In other words, as illustrated in FIG. 1A and FIG. 1B, the air duct 125' has a one-turn path for each one of the X-axis, the Y-axis, and the Z-axis. Firstly, the air duct 125 is extended from the vacuum ejector valve 123 in the Z-axis direction, and makes one turn. Secondly, the air duct 125 is extended from the vacuum ejector valve 123 in the X-axis direction and makes one turn. Finally, the air duct 125 is extended in the Y-axis direction and makes one turn, and is coupled to the suction device 51.

The suction device 51 includes a pair of suction pads 52 that suck one of the multiple medicine packages 2, and a suction duct 53 coupled to the pair of suction pads 52. The vacuum ejector valve 123 communicates with the suction duct 53. Each of the pair of suction pads 52 is an example of an air suction unit or a suction member that sucks up and picks up one of the multiple medicine packages 2 in one of the multiple cartridges 10. As described above, the upper ends of the pair of suction pads 52 as illustrated in FIG. 7A is arranged to absorb one of the multiple medicine packages 2. The bottom ends of the pair of suction pads 52 as illustrated in FIG. 7A is attached and fixed to the upper end of the suction duct 53 as illustrated in FIG. 7A. The bottom end of the suction duct 53 as illustrated in FIG. 7A is attached and fixed to the suction-pad supporting member 54. The pair of suction pads 52 and suction ducts 53 are arranged in the Y-axis direction.

The pickup device 50 is provided with a posture changing unit used to change the posture of one of the multiple medicine packages 2 picked up from one of the multiple cartridges 10 to a substantially vertical posture. The posture changing unit in the pickup device 50 includes a suction-pad supporting member 54 coupled to a suction device base 57 through a rotary shaft 55, a guide 59 formed with a guide groove 59_a_ having a specific shape, a guide axis 56 that is consistently fitted into the guide groove 59_a_ of the guide 59 to guide the suction-pad supporting member 54, and a suction-device lifting and lowering unit.

The suction-pad supporting member 54 is coupled to the suction device base 57 through the rotary shaft 55. The suction-pad supporting member 54 may be [may] rotatably or pivotably arranged around the rotary shaft 55 fixed to the suction-pad supporting member 54 within a range of a predetermined angle. Alternatively, the suction-pad supporting member 54 may be rotatably or pivotably arranged around the rotary shaft 55 fixed to the suction device base 57. In other words, in FIG. 7A and FIG. 7B, the distance between the center of the rotary shaft 55 and the center of a guide rod 58 in the X-axis direction, as will be described later in detail, is kept constant when the suction device base 57 moves along the guide rod 58 in up and down directions Z.

The suction-device lifting and lowering unit includes a pair of guide rods 58 that are arranged in the Y-axis direction to guide the suction device base 57 in the Z-axis direction, an endless belt 62 looped around a driving pulley 60 and a driven pulley 61, and a drive motor 63 coupled to the driving pulley 60 through a driving power conveyor such a gear or a belt. The drive motor 63 is an example of a driver circuit or driving source of the suction-device lifting and lowering unit.

The suction device base 57 is coupled and fixed to the endless belt 62 at a belt grip 62_a_ fixed to the right end of the suction device base 57.

The pair of guide rods 58 are arranged at two different positions in the Y-axis direction, and extend in the Z-axis direction. The bottom ends of those guide rods 58 are fixed to the base frame 50_b_ of the picking-up frame 50_a_ provided for the pickup device 50.

A pair of guiding holes 57_a_ into which the pair of guide rods 58 are inserted are formed around a right end of the suction device base 57.

The pulley axis of each one of the driving pulley 60 and the driven pulley 61 is rotatably supported by an immovable member of a picking-up frame 50_a_ shaped like a box. The drive motor 63 is fixed to an immovable member of the picking-up frame 50_a_ of the pickup device 50. The drive motor 63 is also a driver circuit to be controlled (see FIG. 11 as will be described later in detail) of the suction unit lifting and lowering unit.

When the suction device base 57 is lifted or lowered by the operation of the drive motor 63, the suction device base 57 is moved along the pair of guide rods 58 in the Z-axis direction. Accordingly, the posture of the suction device base 57 on the XY plane can be kept constant in a substantially horizontal state.

The suction unit lifting and lowering unit is not limited to the above-described up-and-down reciprocating mechanism driven by a belt. Alternatively, for example, the suction unit lifting and lowering unit may have a reciprocating linear motion mechanism using a rack and pinion.

A pair of guides 59 are arranged on both sides of the suction device 51 in the Y-axis direction across the suction-pad supporting member 54, and the bottom end of the guide 59 is fixed to the base frame 50*b*.

The guide axis 56 is arranged at both ends of the suction-pad supporting member 54 in the Y-axis direction so as to protrude, and is consistently fitted into the guide groove 59*a* of the guide 59 to guide the suction-pad supporting member 54, and a suction pad lifting and lowering unit. As illustrated in FIG. 7A, the guide axis 56 is arranged under the rotary shaft 55 of the suction-pad supporting member 54 in the Z-axis direction, at a certain distance from the rotary shaft 55.

When the suction device base 57 is moved in the Z-axis direction by the operation of the drive motor 63, the guide axis 56 of the suction-pad supporting member 54 is moved in the Z-axis direction parallel to the guide groove 59*a* having a specific shape while maintaining the posture of the suction device base 57 on the XY plane constant in a substantially horizontal state. Due to such a configuration, the posture of the pair of suction pads 52 can be rotated by approximately 90 degrees. In FIG. 7A, the suction device 51 that is rotated by approximately 90 degrees is indicated by thick broken lines.

In the present embodiment, the expression "substantially horizontal state" indicates that the posture of a particular element is within a specific range of tolerance for angle with respect to the horizontal in addition to a state in which the position of a particular element is horizontal.

The guide groove 59*a* having a specific shape includes the first guide groove that extends in the Z-axis direction with relatively great length so as to hold the posture of the pair of suction pads 52 upward as indicated by solid lines in FIG. 7A through the suction-pad supporting member 54 in a substantially horizontal state as guided by the guide axis 56. Moreover, the guide groove 59*a* includes the second guide groove that gently draws an obtuse and shallow arc to the right side as it goes downward to rotate the posture of the suction-pad supporting member 54 and the pair of suction pads 52 by approximately 90 degrees, and the first guide groove and the second guide groove communicate with each other and are coupled to each other.

Due to the relation between the guide groove 59*a* and the cross-axis distance between the rotary shaft 55 and the guide axis 56 as described above, the pair of suction pads 52 can take various kinds of posture by moving about the rotary shaft 55 that serves as a fulcrum. For example, the posture of the suction pad 52 can be rotated by approximately 90 degrees.

As illustrated in FIG. 7A and FIG. 7B, the pickup device 50 is provided with an upper QR code reader 66 and a lower QR code reader 67 that scans and reads the QR CODE of the label 7 that is pasted onto the subdivision box 34 and has QR code indicating the medication-related information 6*c* on, for example, the medicine package 2 stored in the cartridge 10 as well as the medication-related information 6*c*, as will be described later in detail with reference to, for example, FIG. 12. The upper QR code reader 66 and the lower QR code reader 67 make up a medication-related information reader unit 65 that serves as a pack data reader. The lower QR code reader 67 has the lower reader unit 67*a*, which also serves as the medication-related information reader unit 65, at a lower position, and is attached to a side of the pickup device 50 under the upper QR code reader 66. Cases are described below in which the QR CODE that is on the subdivision box 34 and indicates the medication-related information 6*c* is read by the lower reader unit 67*a* of the lower QR code reader 67 immediately before the medicine package 2 is picked up from one of the multiple cartridges 10 and is dispensed to desired one of the multiple subdivision boxes 34 of the medicine dispensing tray 30.

The operation of the pickup device 50 is described below with reference to FIG. 8A to FIG. 9B. For the sake of explanatory convenience, it is assumed in the present embodiment that, due to the operation of the conveyor 90 illustrated in FIG. 1A and FIG. 1B, the pickup device 50 is arranged below the cartridge 10 provided for one of the drawers 21 arranged at the central portion of the housing 199 illustrated in FIG. 1A and FIG. 1B. In the present embodiment, it is assumed that the cartridges illustrated in FIG. 4A and FIG. 4B and the multiple cartridge trays illustrated in FIG. 1A, FIG. 1B, and FIG. 6 are used as the multiple cartridges 10 and the drawers 21, respectively.

After the pair of suction pads 52 of the pickup device 50 sucks and pulls out the lowermost pack in the cartridge 10, as the conveyor 90 operates, the pickup device 50 moves above the medicine dispensing tray 30, which is placed uppermost in FIG. 1A and FIG. 1B. Then, the pickup device 50 drops and insert the pack into a specific partition of the medicine dispensing tray 30.

Figure 8C:
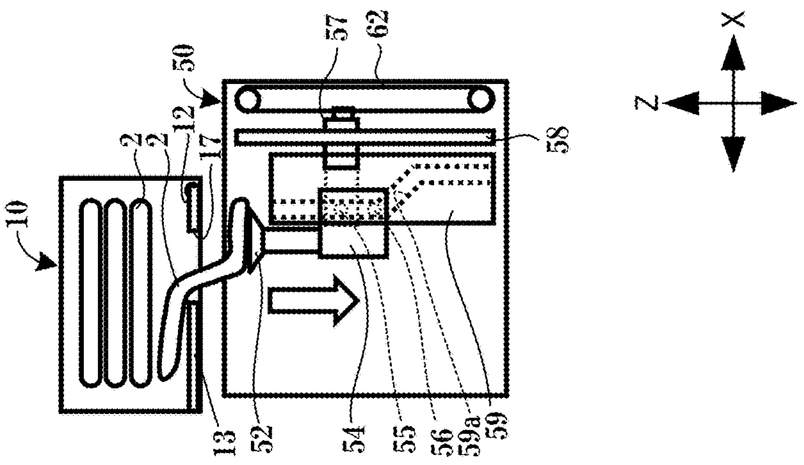
FIG. 8A to FIG. 8F are front views of a pickup device, illustrating the progression of the operation of the pickup device.
Figure 8B:
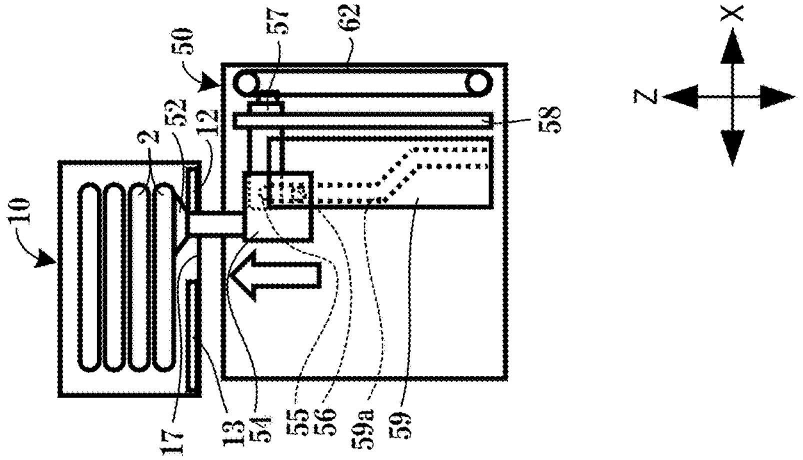
Figure 8A:
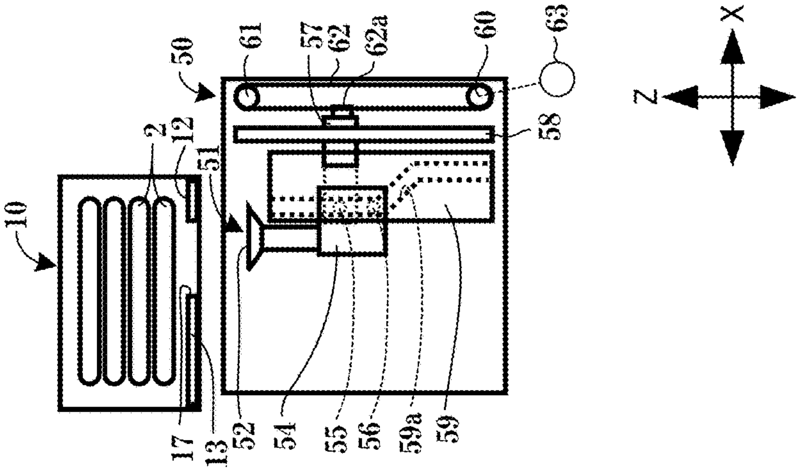

As illustrated in FIG. 8A, the pickup device 50 is moved under one of the cartridges 10 by the operation made by the conveyor 90 illustrated in FIG. 1A and FIG. 1B, and stops moving. Under such conditions, the drive motor 63 of the suction unit lifting and lowering unit is stopped, and the pair of suction pads 52 are positioned under the position of the top face of the pickup device, which indicates the position of the top face of the picking-up frame 50*a* of the pickup device 50. Subsequently, as illustrated in FIG. 8B, the drive motor 63 is driven to rotate, and firstly, the suction device base 57 and the pair of suction pads 52 move upward in a straight line through the coupling between the suction device base 57 that linearly moves and the suction-pad supporting member 54 that linearly and rotationally moves. Accordingly, the pair of suction pads 52 enter from the pack pickup slot 17 between the right support portion 12 and the left support portion 13. Then, as soon as the pair of suction pads 52 contact one of the multiple medicine packages 2 at the bottom of one of the multiple cartridges 10, and the pair of suction pads 52 suck that medicine package 2. In so doing, the vacuum ejector valve 123 (see, for example, FIG. 7A and FIG. 7B) is driven to operate in advance to enable sucking operation.

Subsequently, as illustrated in FIG. 8C, as the drive motor 63 is reversely operated, the pair of suction pads 52 move downward while sucking one of the medicine packages 2 by the pair of suction pads 52, and the front end of one of the medicine packages 2 is pulled out from the cartridge 10. The front end of the medicine package indicates a side of the medicine package to be absorbed or sucked up by the pair of suction pads 52. The operation of pulling out the front end of one of the multiple medicine packages 2 from the pack pickup slot 17 of one of the multiple cartridges 10 under such conditions can be done without causing any sort of problem as the pulled-out medicine package 2 can deform freely or elastically.

Figure 8D:
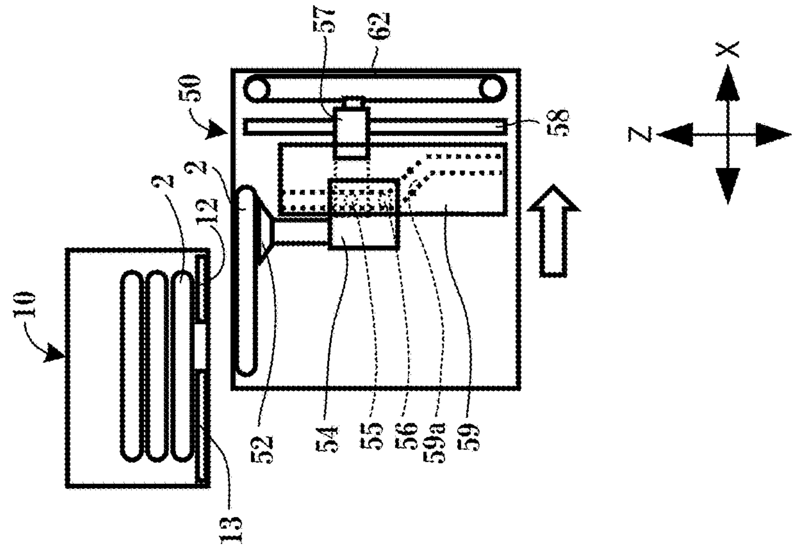
Figure 8E:
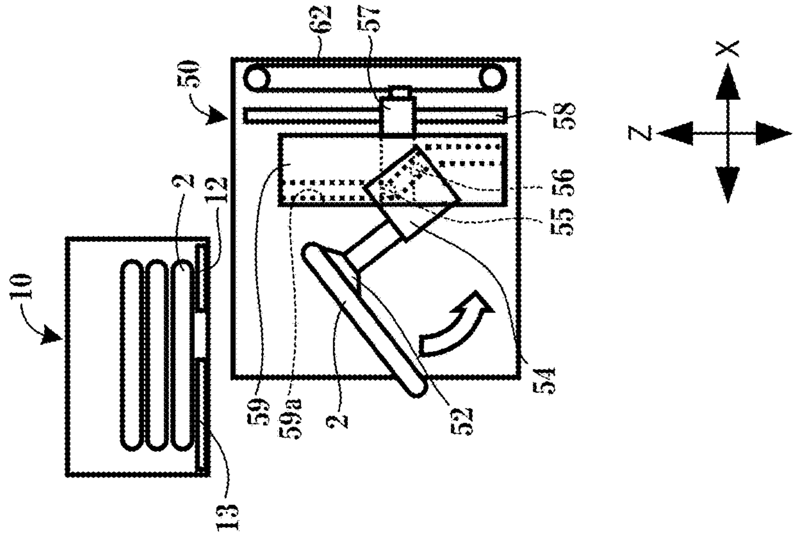
Figure 8F:
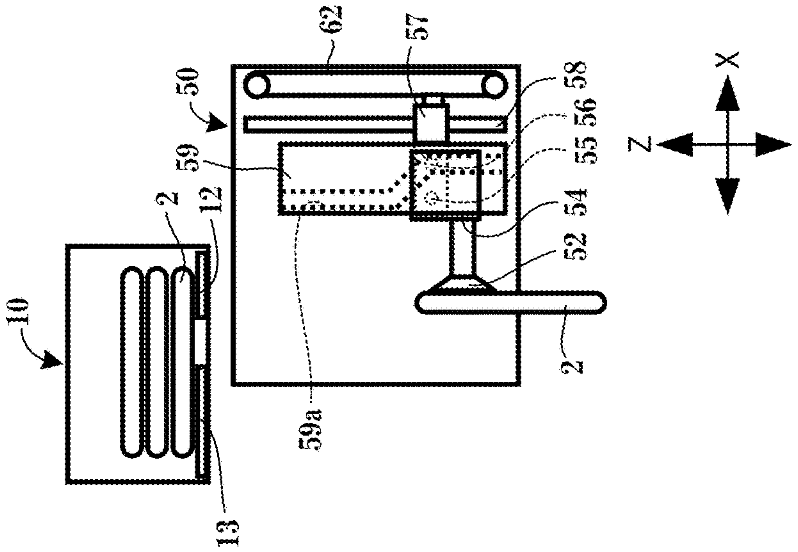

Subsequently, as illustrated in FIG. 8D, by the operation of the conveyor 90 (see FIG. 1A and FIG. 1B), the pickup device 50 is moved in the X-axis direction, which is the lateral direction, and the rear end of one of the multiple medicine packages 2 is drawn out or picked up from one of the multiple cartridges 10. Immediately after that, as illustrated in FIG. 8E and FIG. 8F, by the operation of the drive motor 63, one of the multiple medicine packages 2, which is approximately in a horizontal state and is sucked and held by the pair of suction pads 52, is rotated by substantially 90 degrees to change the posture to an approximately vertical or upright posture. In such rotational operation, the rotary shaft 55 that is arranged on the suction-pad supporting member 54 moves along the guide groove 59*a* of the guide 59. Accordingly, the posture of one of the multiple medicine packages 2 can be changed from an approximately horizontal posture to an approximately vertical posture. The above series of operation in the above configuration may be achieved by a series of operations performed by a single drive motor 63.

Figure 9B:
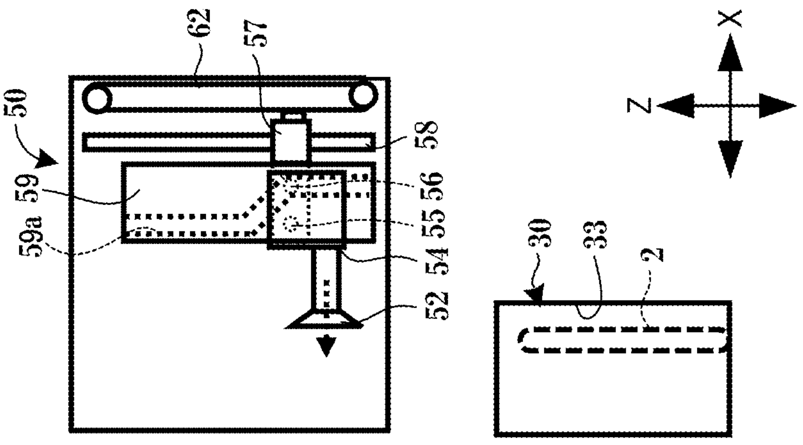
FIG. 9A and FIG. 9B are front views of a pickup device, illustrating the progression of the operation of the pickup device, following FIG. 8A to FIG. 8F.
Figure 9A:
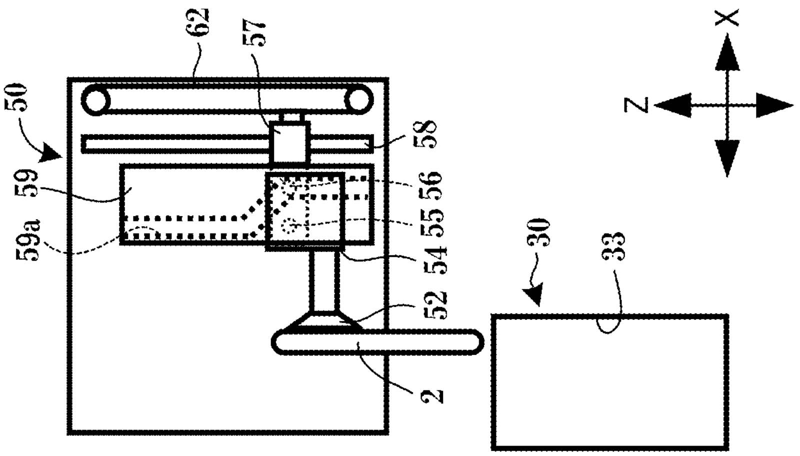

Subsequently, as illustrated in FIG. 9A, the pickup device 50 that includes the pair of suction pads 52 and vertically holds one of the multiple medicine packages 2 is carried to a position substantially directly above the medicine dispensing trays 30 by the conveyor 90, and the operation of the vacuum ejector valve 123 (see FIG. 7A and FIG. 7B) is terminated. As a result, the suction holding of one of the multiple medicine packages 2 by the pair of suction pads 52 is released, and one of the medicine packages 2 is inserted into desired one of the multiple rooms 33 of the medicine dispensing trays 30 or desired one of the multiple subdivision boxes 34 attached to and detached from such desired one of the multiple rooms 33 (See FIG. 9B).

As described above, when desired one of the multiple medicine packages 2 is picked up from one of the multiple cartridges 10, the pickup device 50 is positioned or arranged under one of the multiple cartridges 10, and such desired one of the multiple medicine packages 2 is taken out in the downward direction of one of the multiple cartridges 10. When one of the multiple medicine packages 2 is taken out from the lower side of one of the multiple cartridges 10 as described above, the next one of the multiple medicine packages 2 automatically moves downward or toward the pack pickup slot 17 due to the self weight of the movable board 16 and the multiple medicine packages 2 left in the cartridge 10. Due to such a configuration, the pickup device 50 can perform the same operation with a relatively simple configuration regardless of the number of the multiple medicine packages 2 left in the cartridge 10.

The configuration and operation of the conveyor 90 will be described with reference to FIGS. 10A-10B.

Figure 10B:
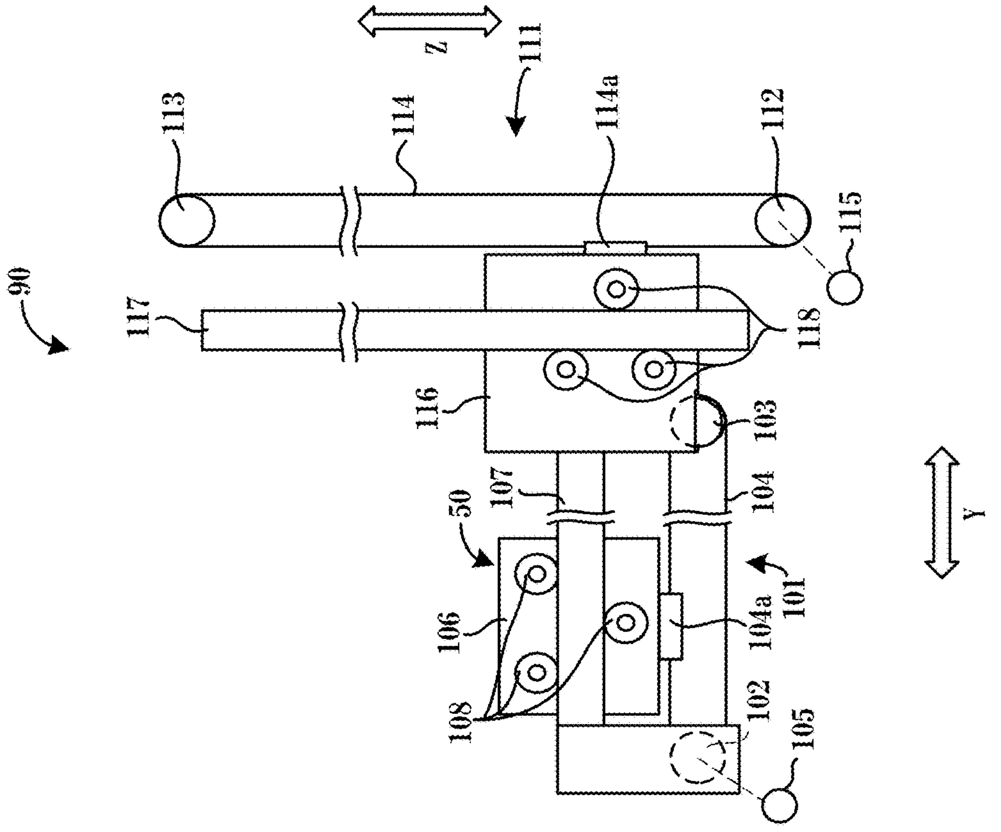
FIG. 10B is a side view of the conveyor of FIG. 10A.
Figure 10A:
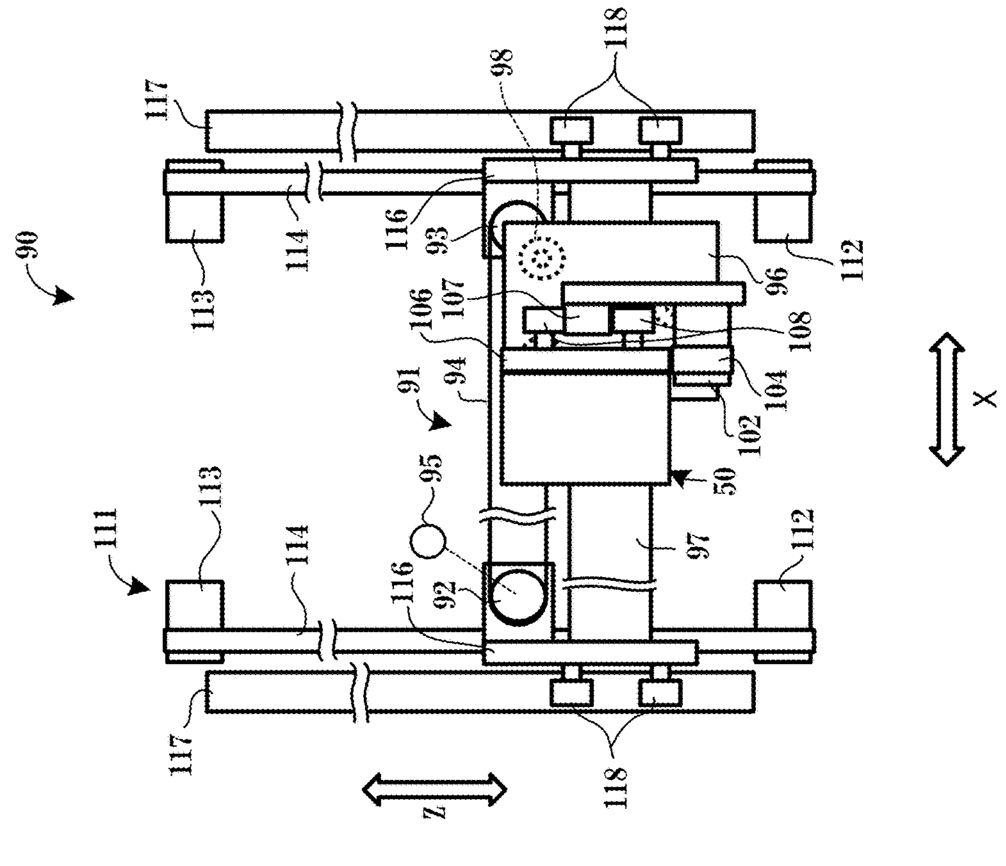
FIG. 10A is a front view of a conveyor, illustrating a schematic configuration of the conveyor.

FIG. 10A is a front view of the conveyor 90, illustrating a schematic configuration of the conveyor 90.

FIG. 10B is a side view of the conveyor 90 of FIG. 10A.

As in the configuration or structure of the medicine dispensing apparatus 200 illustrated in FIG. 1A and FIG. 1B, the multiple cartridges 10 are aligned in rows on planes below the medicine dispensing trays 30 in the Z-axis direction, and the medicine dispensing trays 30 are arranged above the cartridges 10. In view of these circumstances, the pickup device 50 is moved in three directions of the X-axis direction, the Y-axis direction, and the Z-axis direction. In this way, the conveyor 90 moves the pickup device 50 in the X-axis direction, the Y-axis direction, and the Z-axis direction in order to convey one of the multiple medicine packages 2 picked up from one of the multiple cartridges 10 by the pickup device 50 and pass it to one of the multiple medicine dispensing trays 30.

The pickup device 50 is moved in the X-axis direction by an X-axis direction conveyor 91, and the pickup device 50 is moved in the Y-axis direction by a Y-axis direction conveyor 101. The pickup device 50 is moved in the Z-axis direction by a Z-axis direction conveyor 111. These three conveyors have a similar configuration or structure.

The X-axis direction conveyor 91 includes a X-adaptor 96 attached to the pickup device 50, an X-guide unit 97 that guides the pickup device 50 in the X-axis direction through the X-adaptor 96, an endless belt 94 looped around a driving pulley 92 and a driven pulley 93, and a drive motor 95 that is coupled to the driving pulley 92 through a driving force conveyor such as a gear or a belt and is used for the conveyance in the X-axis direction.

As illustrated in FIG. 10A and FIG. 10B, three rollers 98 are attached to the X-adaptor 96 so as to clamp the X-guide unit 97. Due to such a configuration, the X-adaptor 96 can roll over the X-guide unit 97. Note also that two of the three rollers 98 are hidden by the pickup device 50 and invisible in FIG. 10A and FIG. 10B. The X-adaptor 96 is fixedly coupled to the endless belt 94 through a belt grip.

When the drive motor 95 is driven to rotate due to the above configuration or structure of the X-axis direction conveyor 91, the driving force is conveyed to the endless belt 94 through the driving force conveyor and the driving pulley 92, and the endless belt 94 runs in rotation. Accordingly, the pickup device 50 moves in the X-axis direction along the X-guide unit 97 together with the X-adaptor 96.

The Y-axis direction conveyor 101 includes a Y-adaptor 106 attached to the pickup device 50, a Y-guide unit 107 that guides the pickup device 50 in the Y-axis direction through the Y-adaptor 106, an endless belt 104 looped around a driving pulley 102 and a driven pulley 103, and a drive motor 105 coupled to the driving pulley 102 through a driving force conveyor such as a gear or a belt for the conveyance in the Y-axis direction.

Three rollers 108 are attached to the Y-adaptor 106 so as to clamp the Y-guide unit 107. Due to such a configuration, the Y-adaptor 106 can roll over the Y-guide unit 107. The Y-adaptor 106 is coupled and fixed to the endless belt 104 through the belt grip 104*a*.

When the drive motor 105 is driven to rotate due to the above configuration or structure of the Y-axis direction conveyor 101, the driving force is conveyed to the endless belt 104 through the driving force conveyor and the driving pulley 102, and the endless belt 104 runs in rotation. Accordingly, the pickup device 50 moves in the Y-axis direction along the Y-guide unit 107 together with the Y-adaptor 106.

The Z-axis direction conveyor 111 includes a pair of Z-adaptors 116 attached to both ends of the X-guide unit 97 in the X-axis direction, a pair of Z-guide units 117 that guides the pickup device 50 in the Z-axis direction through the X-guide unit 97 and the pair of Z-adaptors 116, an endless belt 114 looped around a driving pulley 112 and a driven pulley 113, and a drive motor 115 coupled to the driving pulley 112 through a driving force conveyor such as a gear or a belt for the conveyance in the Z-axis direction.

In the Z-axis direction conveyor 111, the driving pulley 112, the driven pulley 113, and the endless belt 114 are arranged on both sides in the X-axis direction. The drive motor 115 is provided for only one of the pair of driving pulleys 112.

Three rollers 118 are attached to each one of the pair of Z-adaptors 116 so as to clamp corresponding one of the pair of Z-guide units 117. Due to such a configuration, the pair of Z-adaptors 116 can roll over the pair of Z-guide units 117, respectively. The pair of Z-adaptors 116 are coupled and fixed to the pair of endless belts 114 through a pair of belt grips 114*a*, respectively.

When the drive motor 115 is driven to rotate due to the above configuration or structure of the Z-axis direction conveyor 111, the driving force is conveyed to the endless belt 114 through the driving force conveyor and the driving pulley 112, and the endless belt 114 runs in rotation. Accordingly, the pickup device 50 moves in the Z-axis direction along Z-guide unit 117 together with the X-guide unit 97 and the Z-adaptor 116.

In FIGS. 10A-10B, the pickup device 50 moves in the triaxial directions including the X-axis direction, the Y-axis direction, and the Z-axis direction. However, no limitation is indicated thereby. For example, when the cartridge 10 is arranged above the pickup device 50 and the medicine dispensing tray 30 is arranged below the pickup device 50, the pickup device 50 only needs to move in the X-axis direction and the Y-axis direction. In such cases, the number of axes of motion can be reduced by one.

Figure 11:
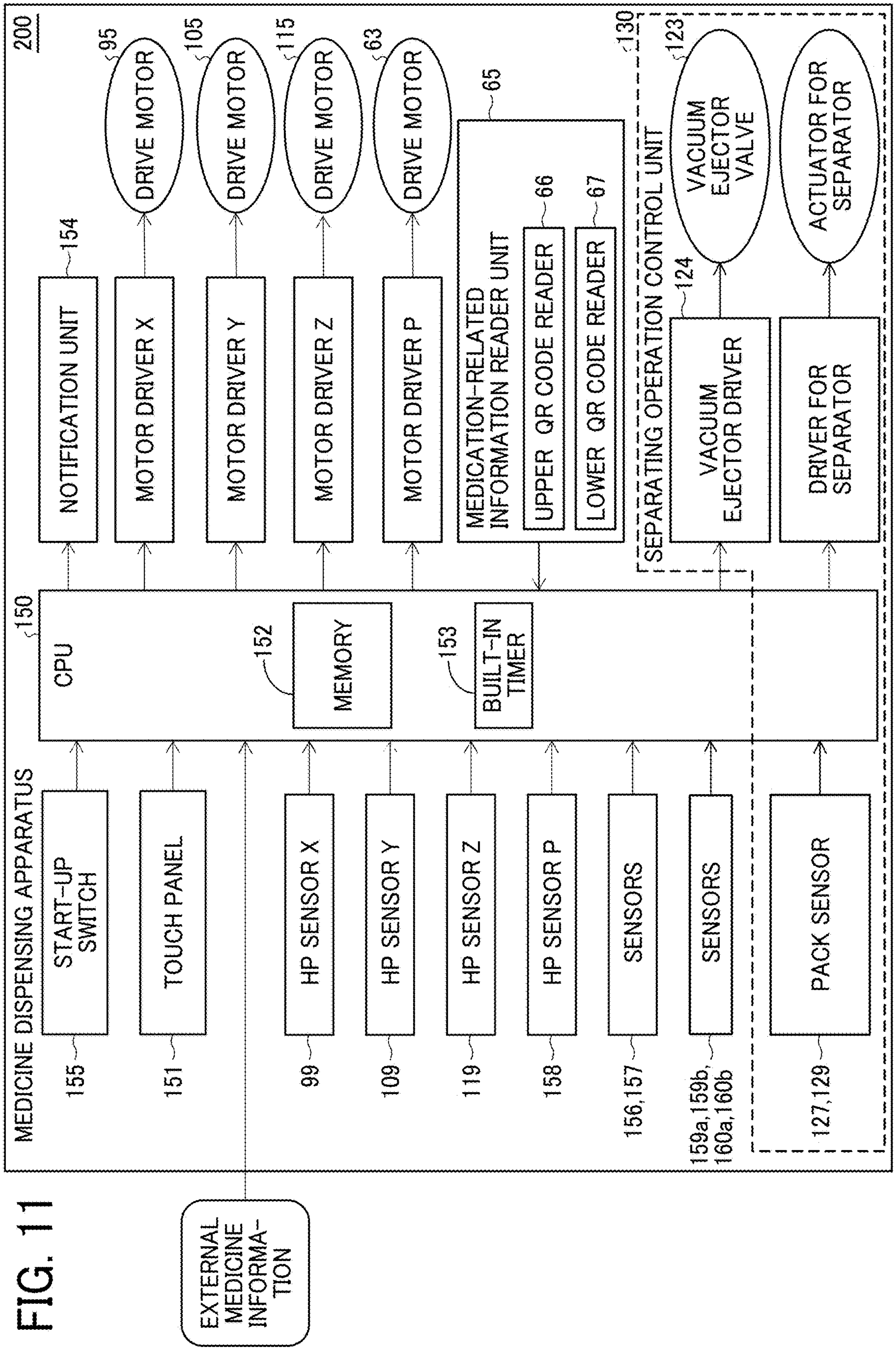
FIG. 11 is a control block diagram illustrating a schematic control structure for the medicine dispensing apparatus of FIG. 1A and FIG. 1B.

FIG. 11 is a control block diagram illustrating a schematic control structure for the medicine dispensing apparatus 200.

As illustrated in FIG. 11, the medicine dispensing apparatus 200 includes a central processing unit (CPU) that is an example of a controller 150 that controls the operation of, for example, the components or elements of the medicine dispensing apparatus 200. For example, the CPU may be provided with a built-in memory 152 or a built-in timer 153. The CPU according to the present embodiment may provide notification to, for example, a user including staff or the like at a timing consistent with the program or may instruct the medicine dispensing apparatus 200 to perform particular operation, based on various kinds of input such as the inputs from a sensor as will be described later in detail. In other words, the CPU according to the present embodiment executes various kinds of control operation as will be described later in detail in the following description or the flowchart of the controlling processes. To the built-in memory 152, prescription data or medicine information are externally input as external medicine information.

The CPU may have, for example, a computing or control function, and a timer or clocking function. The built-in memory 152 includes, for example, a read-only memory (ROM), a random access memory (RAM), and an external memory. The ROM according to the present embodiment stores, for example, a program readable by the above CPU and various kinds of data in advance. Such a program stored in the ROM may be a program used in the flowchart of the controlling processes as will be described later in detail. The above various kinds of data may be, for example, the data about the relation between the medicine packages 2 and the rooms 33 of one of the multiple medicine dispensing trays 30 allocated to each of the patients who take medicines, the data about the relation between the multiple medicine packages 2 and the multiple rooms 33 of one of the multiple medicine dispensing trays 30 assigned to each one of the times of medication, or the data about the relation between the multiple medicine packages 2 and the multiple rooms 33 of one of the multiple medicine dispensing trays 30 sorted according to the order in which medicines are to be taken (see FIG. 4A and FIG. 4B).

The CPU has an input and output (I/O) port, and a touch panel 151 that is an example of a user interface (UI) provided with an input unit and a display unit is electrically connected to that input and output port of the CPU. Through the touch panel 151, various kinds of inputs can be made, and for example, the current time, the progress of the storing process of packs, or the stop time are displayed on the touch panel 151. How such inputs are made or the structure or configuration of such a display unit are not limited thereto, and may be, for example, an input unit and a display unit may be arranged separately. Alternatively, a combination of an input device and a display interface such as a combination of a keyboard and a light-emitting diode (LED) display may be adopted.

To the input port of the CPU, a start-up switch 155 that drives the medicine dispensing apparatus 200 to operate is electrically connected. Once the start-up switch 155 is touched or pressed down, medicine dispensing operation to the medicine dispensing trays 30 starts step by step. The medicine dispensing operation to the medicine dispensing trays 30 may start at a time determined in advance by the built-in timer 153.

The CPU according to the present embodiment has an input port, and a medicine dispensing tray sensor 156 that detects the type of medicine dispensing tray 30 stored in the medicine dispensing apparatus 200 or determines whether or not there is any medicine dispensing tray 30, and a container sensor 157 that determines whether or not there is any one of the multiple cartridges 10 are electrically connected to the input port of the CPU.

The medicine dispensing tray sensor 156 and the container sensor 157 are illustrated in FIG. 11.

To the input port of the above CPU, a home position (HP) sensor 99 that is used for a home position (HP) sensor X to detect the home position (HP) of the X-axis direction conveyor 91 in the pickup device 50, an HP sensor 109 that is used for an HP sensor Y to detect the home position (HP) of the Y-axis direction conveyor 101 in the pickup device 50, and an HP sensor 119 that is used for an HP sensor Z to detect the home position (HP) of the Z-axis direction conveyor 111 in the pickup device 50 are electrically connected.

Moreover, to the input port of the CPU, a home position (HP) sensor 158 for a HP sensor P that detects the home positions (HP) of the pair of suction pads 52 of the suction device 51 in the pickup device 50 is electrically connected.

To the output port of the above CPU, the drive motor 95 for the X-axis direction conveyor 91, the drive motor 105 for the Y-axis direction conveyor 101, the drive motor 115 for the Z-axis direction conveyor 111, and the drive motor 63 used to change the posture or attitude of the pair of suction pads 52 are electrically connected to the input port of the CPU through various kinds of motor drivers X, Y, Z, and P, respectively.

To the output port of the CPU, a notification unit 154 may be electrically connected. The notification unit 154 reports what sort of state or conditions the components or elements of the medicine dispensing apparatus 200 are in by means of, for example, the light emitted from a light-emitting diode (LED) and the sound or vibration including voice. Moreover, the notification unit 154 may be provided with, for example, a loudspeaker or a light that indicates that the medicines are to be taken so that the staff or the like away from the medicine dispensing apparatus 200 can be notified of such a time of medication.

The external medicine information is also input to the CPU through an input and output (I/O) interface, and is stored in the built-in memory 152. For example, the external medicine information is used for the allocation of medicines to patients who take medicines. For example, the LEDs 25*a*1 to 25*d*5 of the drawer 21 may be electrically connected to each other.

Once the input data from the touch panel 151 and various kinds of signals from various types of sensors or the HP sensors 99, 109, 119, and 158 are input to the CPU, a command signal is newly output from the CPU. In other words, the CPU according to the present embodiment outputs a command signal used to control the audio device or the optical device of the display device of the touch panel 151 including the above notification unit, the LEDs 25*a*1 to 25*d*5, the drive motor 63, the drive motor 95, the drive motor 105, the drive motor 115, or the multiple drives that correspond to the multiple LEDs.

As various types of sensors, a pair of drawer gate opening and closing sensors 159*a* and 159*b* that detect the opening and closing of the first gate 41 and the second gate 42 and a pair of medicine dispensing tray gate opening and closing sensors 160*a* and 160*b* that detect the opening and closing of the third gate 43 and the fourth gate 44 are electrically connected to the input port of the CPU. The medicine dispensing tray sensor 156, the container sensor 157, the pair of drawer gate opening and closing sensors 159*a* and 159*b*, and the pair of medicine dispensing tray gate opening and closing sensors 160*a* and 160*b* are illustrated only in FIG. 11.

Figure 15B:
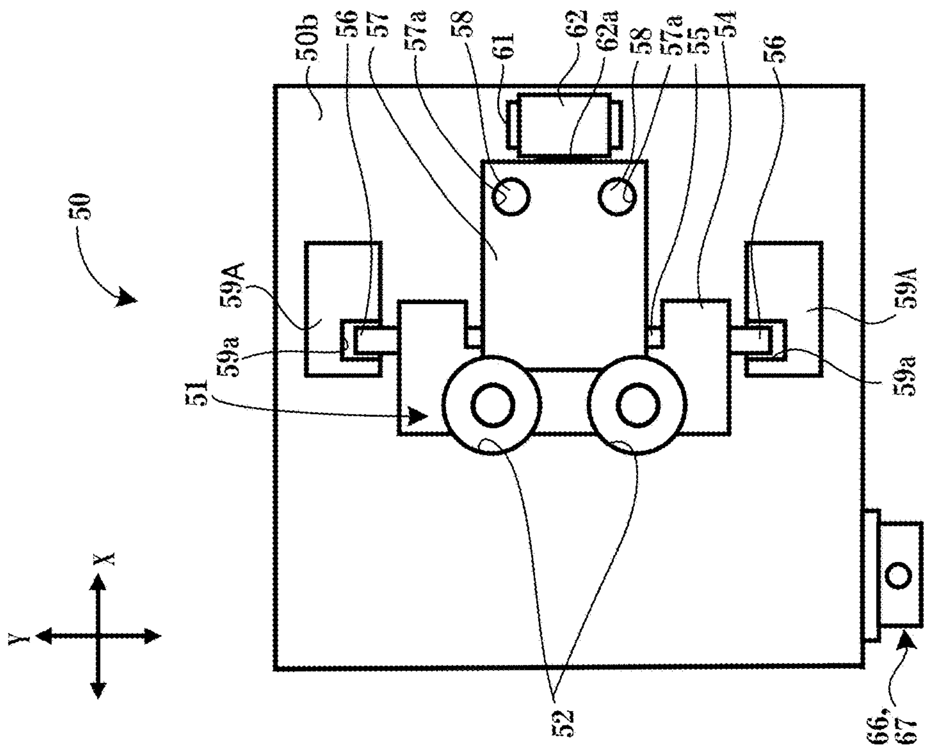
FIG. 15B is a plan view of the pickup device illustrated in FIG. 15A.
Figure 15A:
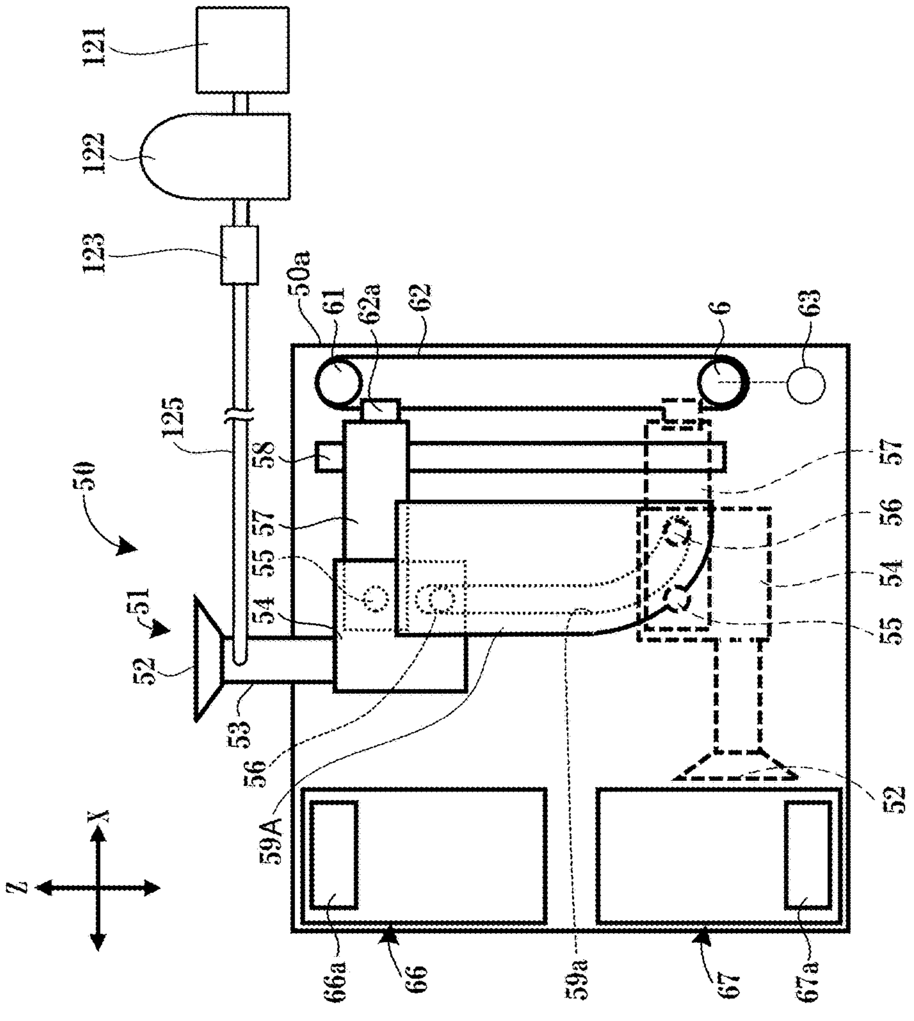
FIG. 15A is a front view of a pickup device, illustrating a configuration or structure of the pickup device substantially equivalent to that of FIG. 7A and FIG. 7B.

The upper QR code reader 66 that serves as the medication-related information reader unit 65 or an upper reader unit 66*a* and the lower QR code reader 67 that serves as the medication-related information reader unit 65 or a lower reader unit 67*a*, each of which is provided for the pickup device 50 as will be described later in detail with reference to FIG. 15A and FIG. 15B, are electrically connected to the input port of the CPU.

The CPU according to the present embodiment executes various kinds of control operation as will be described later in detail in the following description or the flowchart of the controlling processes. The CPU serves as a controller that controls the medicine dispensing operation by the pickup device 50 and the conveyor 90 to make one of the medicine packages 2 picked up from one of the cartridges 10 arranged at a desired position of (one of the rooms 33 or the subdivision boxes 34 of) the medicine dispensing tray 30, based on the medication-related information 6*c* that is displayed on the cartridge 10 or the medicine package 2 placed therein and is read using the upper QR code reader 66 or the medication-related information 6*c* that is displayed on the room 33 or the subdivision box 34 of the medicine dispensing tray 30 and is read by the lower QR code reader 67.

As will be described later in detail, after the medicine dispensing operation starts, the CPU skips a process with abnormalities, and makes the medicine dispensing operation continue. As will be described later in detail, a separating operation control unit 130 surrounded by a broken line in FIG. 11 is a control structure of the medicine dispensing apparatus 200.

Figure 12:
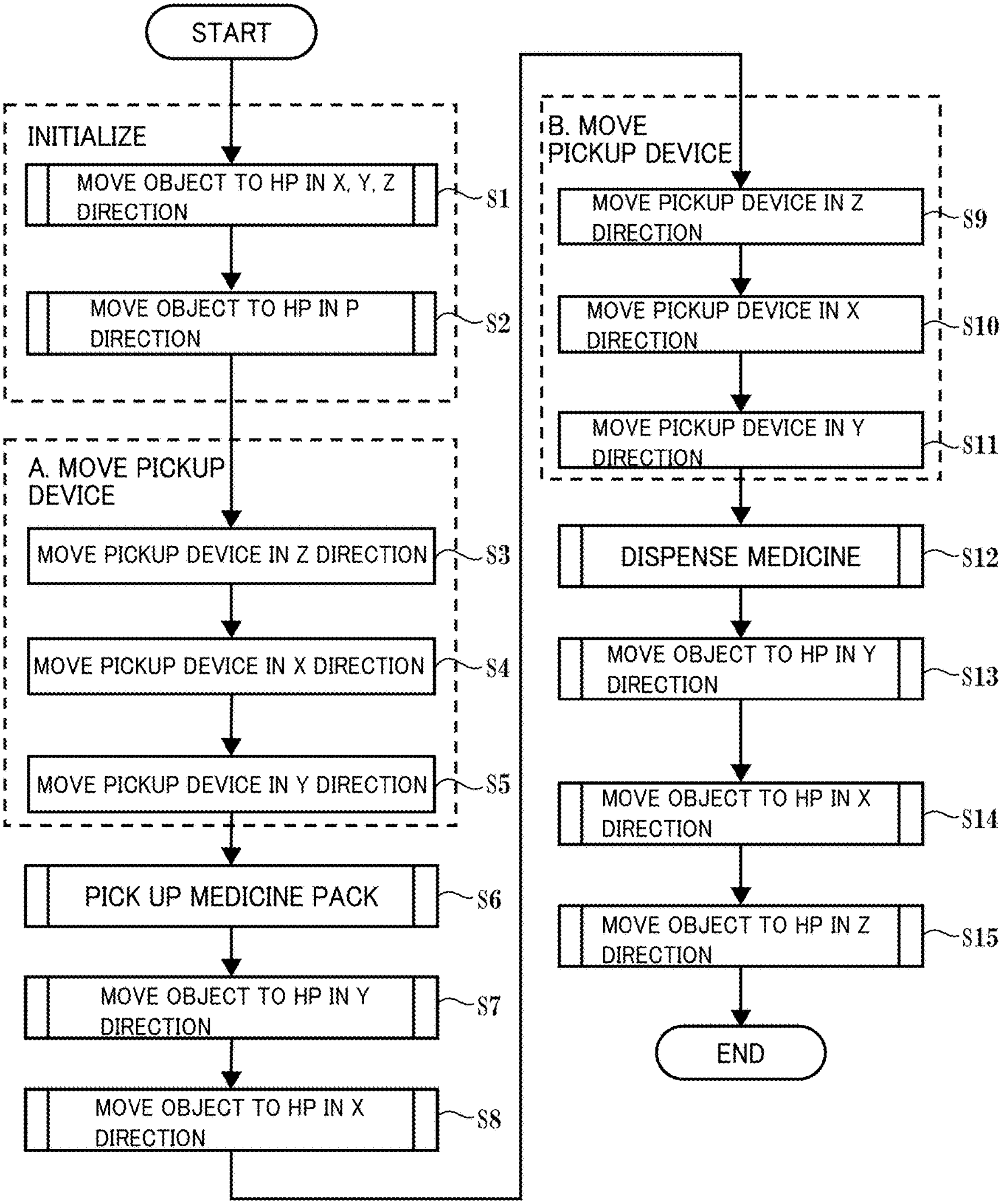
FIG. 12 is a flowchart of the sequence of basic operations of a medicine dispensing apparatus.

FIG. 12 is a flowchart of the sequence of basic operation of the medicine dispensing apparatus 200.

Figure 13:
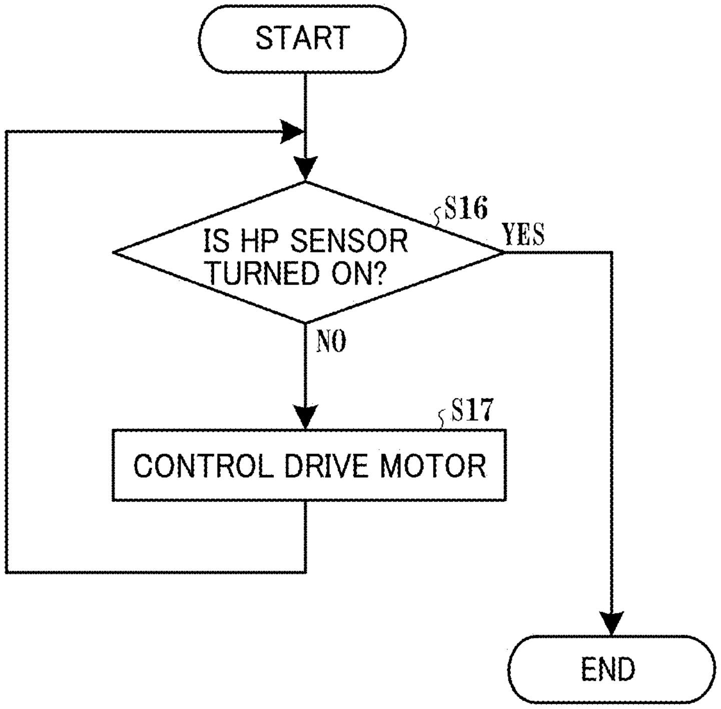
FIG. 13 is a flowchart of the processes of moving a home position, which is a subroutine program of FIG. 12.

FIG. 13 is a flowchart of the processes of moving the home position (HP), which is a subroutine program of FIG. 12.

Figure 14:
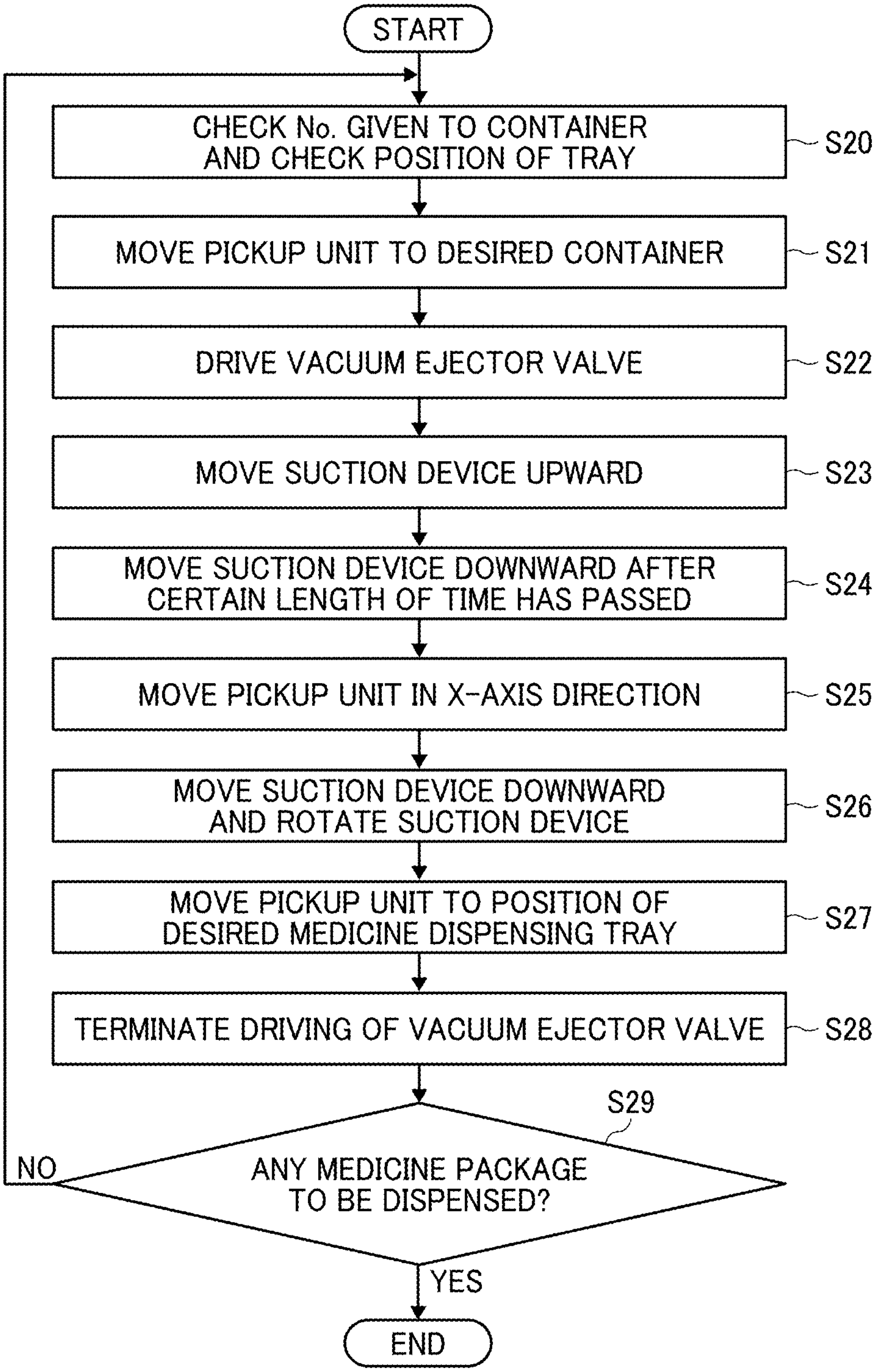
FIG. 14 is a flowchart of the operation of a pickup device.

FIG. 14 is a flowchart of the operation of the pickup device 50.

The operations in FIG. 12, FIG. 13, and FIG. 14 are executed under the control commands from the CPU of the controller 150.

When the start-up switch 155 illustrated in FIG. 11 is turned on, the process starts, and in steps S1 and S2, firstly, initialization is performed as illustrated in FIG. 12 (see the initialization part indicated by a frame of broken line in FIG. 12).

In the initialization, the HP sensor and the corresponding drive motor are controlled by the subroutines as depicted in FIG. 13, and an object to be controlled is moved to a predetermined home position (HP) where the HP sensor is turned on (see steps S16 to S17 in FIG. 13). A series of processes are automatically performed by a built-in timer 153 as depicted in FIG. 11 as follows at prescribed timings that correspond to the medication support operations in the morning, at lunchtime, in the evening, or before going to bed, based on the medicine information that is externally obtained in advance or the input from the touch panel 151 illustrated in FIG. 11.

At predetermined times, in steps S3 to S5, the CPU drives the drive motor 115, the drive motor 95, and the drive motor 105 that correspond to Z, X, and Y, respectively, in the order listed to move the pickup device 50 to desired one of the cartridges 10 (see "A. MOVE PICKUP DEVICE" indicated by a frame of broken line in FIG. 12). Subsequently, as a series of picking-up operations, a drive motor 63 that is used for a drive motor P is driven so that the pair of suction pads 52 are moved close to the medicine package 2 (see FIG. 8B), and the vacuum ejector valve 123 (see FIG. 7A, FIG. 7B, and FIG. 11) is controlled to make the pair of suction pads 52 suck the medicine package 2. Subsequently, the drive motor 63 and a drive motor 95 that is used for a drive motor X are operated in cooperation with each other to pick up one of the medicine packages 2 from a position below one of the multiple cartridges 10 (see FIG. 8C and FIG. 8D). Then, in steps S6 to S8, the posture of the pair of suction pads 52 are rotated, and the medicine package 2 is vertically held (see FIG. 8E and FIG. 8F).

Subsequently, in steps S9 to S11, the CPU drives the drive motor 115, the drive motor 95, and the drive motor 105 that correspond to Z, X, and Y, respectively, in the order listed to move the pickup device 50 so as to move of the medicine package 2 to a position above desired one of the rooms 33 of one of the medicine dispensing trays 30 (see "B. MOVE PICKUP DEVICE" indicated by a frame of broken line in FIG. 12). Then, medicines are dispensed. In the medicine dispensing operation, after the operation of the pickup device 50 is terminated, the vacuum ejector valve 123 is controlled to cause vacuum breakdown. As a result, suctioning is released to separate one of the medicine packages 2 and dispense the separated medicine package to the medicine dispensing tray 30 (see FIG. 9A and FIG. 9B). These operations are performed several times. When the delivery of the medicine packs for a predetermined number of persons is completed, the loudspeaker or the light of the notification unit 154 is instructed to notify a medication assistant that the preparation is complete (see steps S12 to S15).

FIG. 14 is a flowchart of the operation of the pickup device 50 described above with reference to FIG. 8A to FIG. 9B.

Firstly, in step S20 of FIG. 14, the number (No.) given to the cartridge 10 that is an object in which the medicine package 2 to be dispensed is stored is checked, and the position of the medicine dispensing tray 30 that is an object to which the medicine package 2 is to be passed is checked. Then, in step S21, the pickup device 50 is moved to desired one of the cartridges 10 by the conveyor 90. In so doing, in step S22, the drive motor 63 is driven to rotate while the vacuum ejector valve 123 is being driven to generate negative pressure at a prescribed timing. By so doing, in step S23, the suction device 51 is moved upward to desired one of the cartridges 10 (see FIG. 8A and FIG. 8B). When the lowermost one of the medicine packages 2 is sucked from one of the multiple cartridges 10 and held by the pair of suction pads 52, in step S24, the drive motor 63 is driven in inverse direction so as to move the suction device 51 downward after certain length of time has passed (see FIG. 8C). Subsequently, in step S25, the pickup device 50 is moved to the right in the X-axis direction of FIG. 8A to FIG. 8F (see FIG. 8D), and desired one of the multiple medicine packages 2 is completely taken out from one of the multiple cartridges 10. Then, in step S26, the drive motor 63 is further driven to rotate in the reverse direction so as to move the suction device 51 downward. As a result, the suction device 51 is rotated by approximately 90 degrees, and the posture of the medicine package 2 is changed from an approximately horizontal posture to an approximately vertical posture (see FIG. 8E and FIG. 8F).

Subsequently, the pickup device 50 is moved by the conveyor 90 to a position directly above a desired one of the rooms 33 or the subdivision boxes 34 of the medicine dispensing tray 30. When the pickup device 50 has moved to the position of desired one of the multiple medicine dispensing trays 30, the operation of the vacuum ejector valve 123 is switched to terminate generating negative pressure and start generating positive pressure. By so doing, the medicine package 2 is released and separated from the pair of suction pads 52, and the medicine package 2 is inserted into a desired one of the rooms 33 or the subdivision boxes 34. Then, the operation of the vacuum ejector valve 123 is terminated. Those operations are performed in step S27 and step S28 (see FIG. 9A and FIG. 9B). Then, in step S29, whether there is any medicine package 2 to be dispensed is checked. When there is no medicine package 2 to be dispersed, a series of operations is terminated. On the other hand, when it is determined that there is at least one medicine package 2 to be dispensed, the process is returned to the step S20, and the same series of processes in the above steps are repeated.

As described above, in the present embodiment, when desired one of the multiple medicine packages 2 is picked up from one of the multiple cartridges 10, the pickup device 50 is positioned under one of the multiple cartridges 10, and such desired one of the multiple medicine packages 2 is taken out in the downward direction of one of the multiple cartridges 10.

When one of the multiple medicine packages 2 is taken out from the lower side of one of the multiple cartridges 10 as described above, the next one of the multiple medicine packages 2 automatically moves downward or toward the pack pickup slot 17 due to the self weight of the movable board 16 and the multiple medicine packages 2 left in the cartridge 10. Due to such a configuration, the pickup device 50 can perform the same operation with a relatively simple configuration regardless of the number of the multiple medicine packages 2 left in the cartridge 10.

The pickup device 50 that is substantially equivalent to that of FIG. 7A and FIG. 7B is described below with reference to FIG. 15A and FIG. 15B so as to describe the QR CODE reading operation.

FIG. 15A is a front view of the pickup device 50, illustrating a configuration or structure of the pickup device 50 substantially equivalent to that of FIG. 7A and FIG. 7B.

FIG. 15B is a plan view of the pickup device 50 illustrated in FIG. 15A.

Compared with the pickup device 50 illustrated in FIG. 7A and FIG. 7B, the pickup device 50 as illustrated in FIG. 15A and FIG. 15B has no substantial difference in configuration or structure. Although the pickup device 50 as illustrated in FIG. 15A and FIG. 15B has a slight difference in shape compared with the pickup device 50 illustrated in FIG. 7A and FIG. 7B, their basic configuration or structure is substantially the same. The pickup device 50 of FIG. 15A and FIG. 15B is different from the pickup device 50 of FIG. 7A and FIG. 7B in that the pickup device 50 of FIG. 15A and FIG. 15B has a guide 59A on which the guide groove 59*a* shaped like horizontally flipped letter J is formed while the pickup device 50 of FIG. 7A and FIG. 7B has the guide 59 on which the guide groove 59*a* is formed with two bent portions. Accordingly, if the medication-related information reader unit 65 illustrated in FIG. 15A and FIG. 15B is added to the pickup device 50 of FIG. 7A and FIG. 7B, the pickup device 50 illustrated in FIG. 7A and FIG. 7B has substantially the same configuration or structure as that of the pickup device 50 as illustrated in FIG. 15A and FIG. 15B.

As illustrated in FIG. 7A, FIG. 7B, FIG. 15A, and FIG. 15B, the pickup device 50 is provided with an upper QR code reader 66 that is an example of a medication-related information reader unit or a medication-related information reader that reads the QR CODE that indicates the medication-related information 6*c* (see FIG. 4A and FIG. 4B) displayed on, for example, the medicine package 2 stored in the cartridge 10. The upper QR code reader 66 has an upper reader unit 66*a* that reads the medication-related information 6*c* at an upper portion thereof, and also serves as a medication-related information reader unit 65. The upper QR code reader 66 is attached to a side of the pickup device 50. As illustrated in FIG. 4A and FIG. 4B, the upper QR code reader 66 is also used to read the QR CODE that indicates the medication-related information 6*c* displayed on the label pasted to the left support portion 13 of the pack pickup slot 17 in one of the multiple cartridges 10. Cases are described below in which the QR CODE that indicates the medication-related information 6*c* is read by the upper reader unit 66*a* of the upper QR code reader 66 immediately before the medicine package 2 is picked up from one of the multiple cartridges 10 by the pickup device 50.

As illustrated in FIG. 7A, FIG. 7B, FIG. 15A, and FIG. 15B, the pickup device 50 is provided with the medication-related information reader unit 65 or the lower QR code reader 67 that serves as a medication-related information reading unit and reads the QR CODE of the label 7 with a QR code that is pasted onto the subdivision box 34 described above with reference to FIG. 4A and FIG. 4B to indicate the medication-related information 6*c*. The lower QR code reader 67 has the lower reader unit 67*a*, which also serves as the medication-related information reader unit 65, at a lower position, and is attached to a side of the pickup device 50 under the upper QR code reader 66. Cases are described below in which the QR CODE that is on the subdivision box 34 or the room 33 and indicates the medication-related information 6*c* is read by the lower reader unit 67*a* of the lower QR code reader 67 immediately before the medicine package 2 is picked up from one of the multiple cartridges 10 and is dispensed to desired one of the multiple subdivision boxes 34 or the rooms 33 of the medicine dispensing tray 30.

Figure 16:
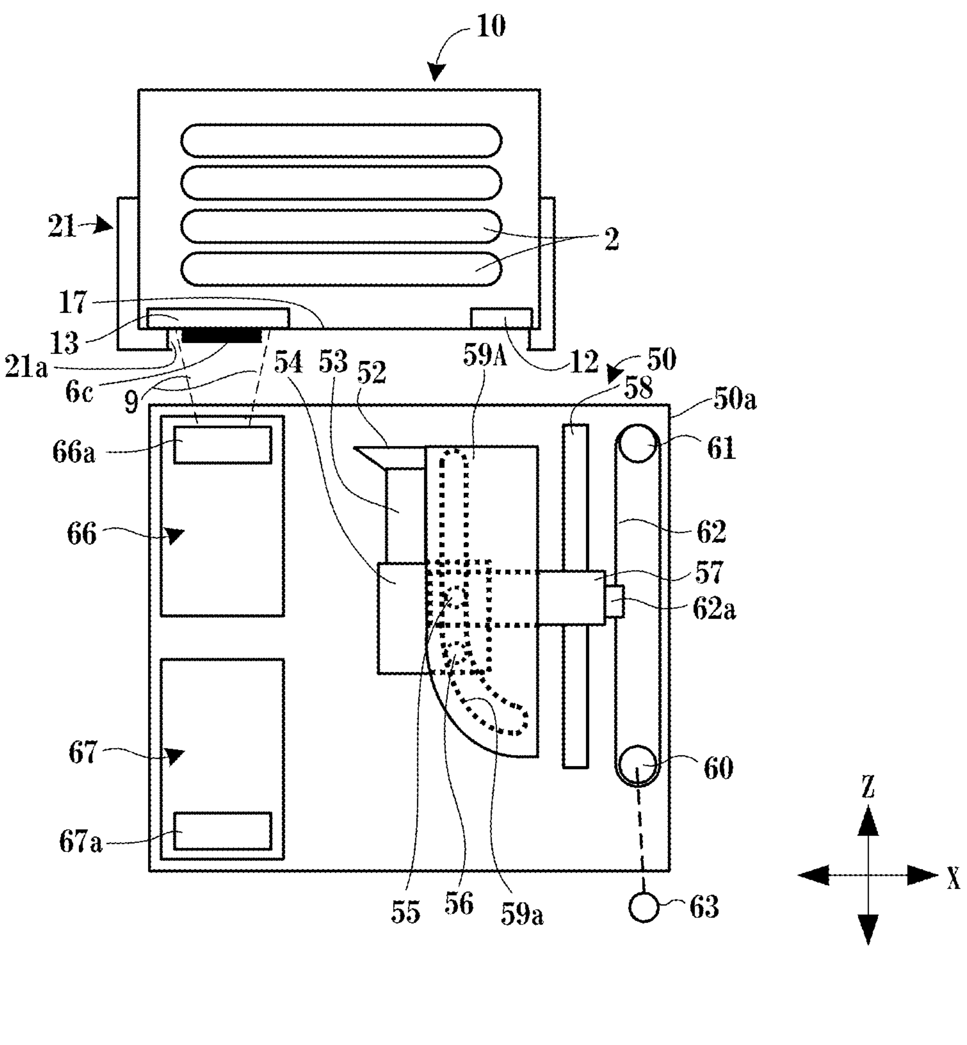
FIG. 16 is a diagram illustrating how the pickup device of FIG. 15A.

FIG. 16 is a diagram illustrating how the pickup device 50 reads the medication-related information 6*c* on the medicine package 2 stored in the cartridge 10.

As illustrated in FIG. 16, in a similar manner to the pickup device 50 illustrated in FIG. 8A, the pickup device 50 moves to a position under the drawer 21 that holds the cartridges 10 containing the medicine packages 2 to be picked up. In other words, the upper reader unit 66*a* of the upper QR code reader 66 in the pickup device 50 is moved to a position approximately directly below the drawer 21 and the cartridge 10 so as to form a scanning range 9 in which the QR CODE that indicates the medication-related information 6*c* on the medicine package 2 stored at the bottom of one of the multiple cartridges 10 can be scanned and read through the opening 21*a* of the drawer 21. The pickup device 50 that is positioned as above reads the QR CODE that indicates the medication-related information 6*c* displayed on the medicine package 2 or the bottom wall of the left support portion 13 of one of the multiple cartridges 10, using the upper reader unit 66*a* of the upper QR code reader 66.

Figure 17A:
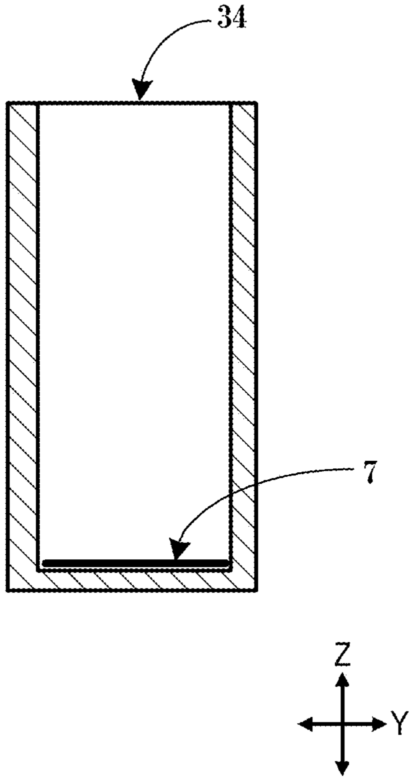
FIG. 17A is a diagram illustrating the attachment of a label with a quick response code (QR CODE) to be placed in a subdivision box used for a medicine dispensing tray.

FIG. 17A is a diagram illustrating the attachment of the label 7 with a QR code to be placed in the subdivision box 34 used for the medicine dispensing tray 30.

Figure 17B:
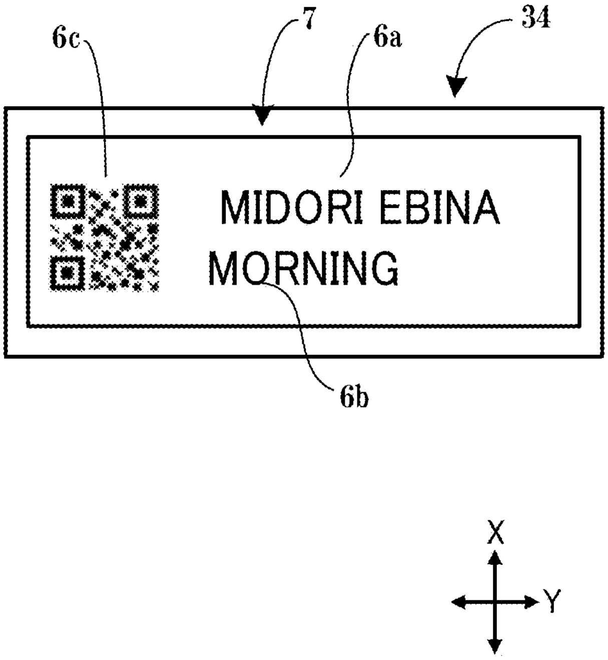
FIG. 17B is a diagram illustrating how a label with a QR CODE is displayed.

FIG. 17B is a diagram illustrating how the label 7 with a QR code is displayed.

In order to specify the place to which one of the multiple medicine packages 2 picked up from one of the multiple cartridges 10 is to be dispensed, a label 7 with a QR CODE on which the medication-related information 6*a* that indicates the name of a patient who takes medicines, the medication-related information 6*b* that indicates the times of medication, and the medication-related information 6*c* are printed is pasted on the inner bottom face of one of the multiple subdivision boxes 34 of the medicine dispensing tray 30. The QR CODE on the label 7 with a QR code indicates the medication-related information 6*a* and the medication-related information 6*b*.

Figure 18:
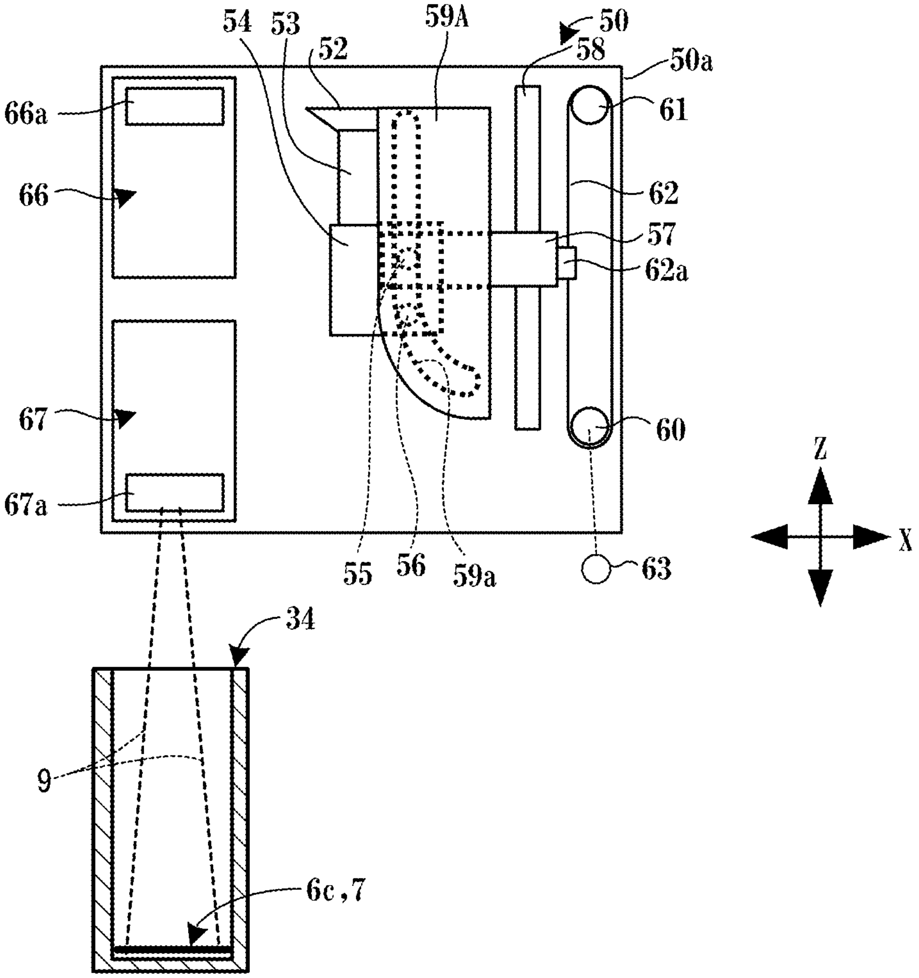
FIG. 18 is a diagram illustrating the reading operation of a label with a QR CODE placed in a subdivision box.

FIG. 18 is a diagram illustrating the reading operation of the label 7 with a QR CODE placed in one of the multiple subdivision boxes 34.

When the pickup device 50 that includes the pair of suction pads 52 and holds one of the multiple medicine packages 2 in a substantially vertical posture is carried by the conveyor 90 to a predetermined position and the pickup device 50 is at a position similar to that of the pickup device 50 illustrated in, for example, FIG. 9A, the lower reader unit 67*a* of the lower QR code reader 67 in the pickup device 50 comes to the predetermined position at which the QR CODE that indicates the medication-related information 6*c* and is displayed at the bottom of predetermined one of the subdivision boxes 34 or rooms 33 of one of the multiple medicine dispensing trays 30 moves to the scanning range 9. Under such conditions, the lower reader unit 67*a* reads the QR CODE that indicates the medication-related information 6*c*.

Figure 19:
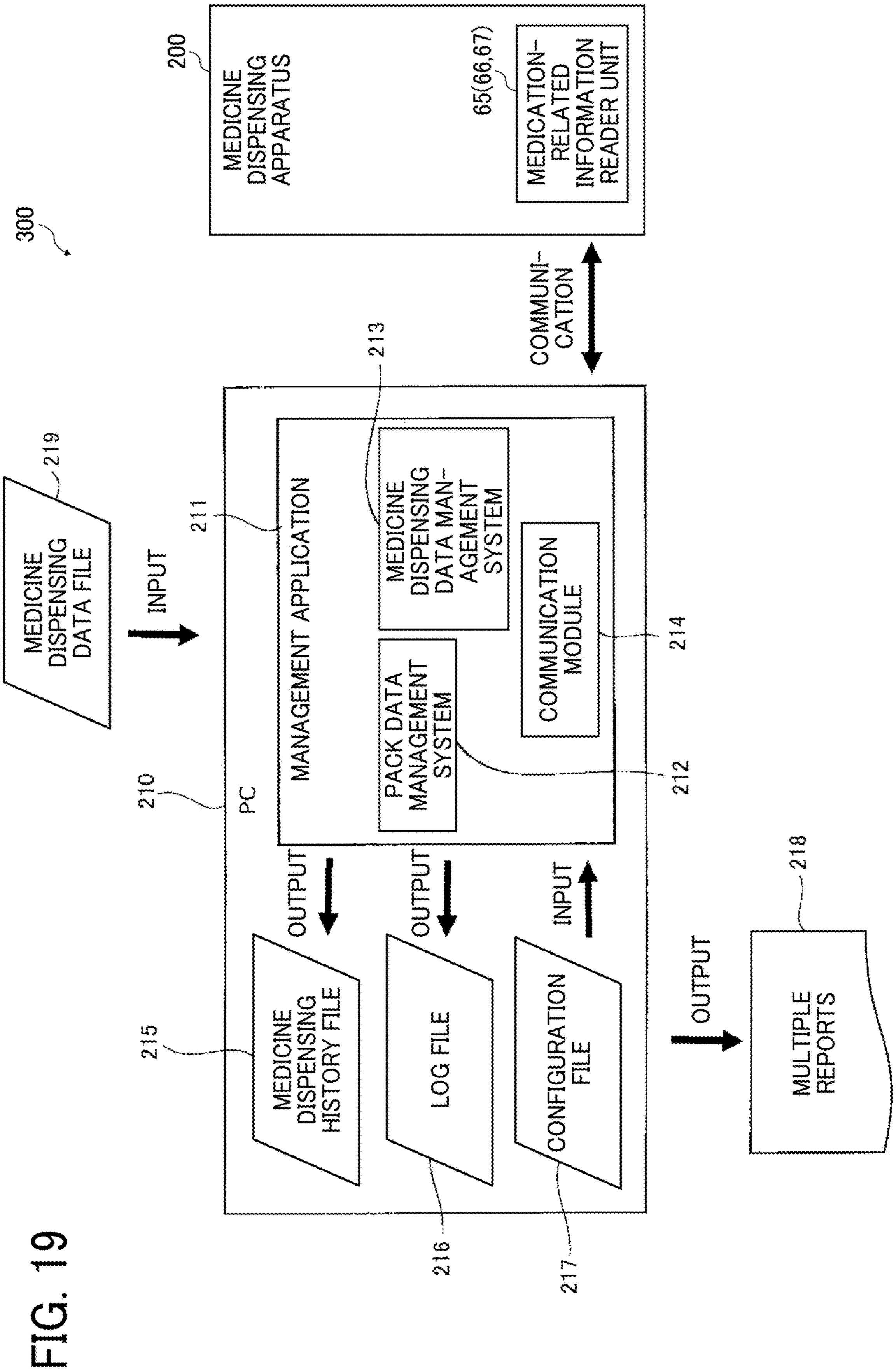
FIG. 19 is a diagram illustrating the control blocks of a medication support device.

FIG. 19 is a diagram illustrating the control blocks of a medication support device 300.

As illustrated in FIG. 19, the medication support device 300 is provided with the above-described medicine dispensing apparatus 200 and a personal computer (PC) 210 coupled to the medicine dispensing apparatus 200. Such coupling enables communication such as data transmission and data reception. The PC 210 includes five elements known in the art. In other words, the PC 210 is provided with, for example, a control device, a processor, a memory, an input device, and an output device. The above control device of the PC 210 is provided with a central processing unit (CPU), and executes a program or gives instructions to other devices. The above processor of the PC 210 executes a program or performs computation. The above memory of the PC 210 is provided with, for example, a main memory and an auxiliary memory, and stores data such as programs or texts. The above input device according to the present embodiment includes, for example, a mouse, a keyboard, a microphone, and sends data or instructions to the computer. The above output device includes, for example, a display, a printer, a loudspeaker, and outputs data or instructions to a computer.

The PC 210 fulfills the function of the medicine dispensing apparatus 200, and serves as a sort of host computer that manages and supports the medicine dispensing apparatus 200 in order to handle the above technical problems and other various kinds of possible problems to be solved in the embodiments of the present disclosure. The PC 210 is connected to a terminal in a pharmacy or the like at which the medicine is supplied, through the network.

The pack data management system 212 provided for the management application 211 reads and manages the medication-related information of the medicine pack. The medicine dispensing data management system 213 provided for the management application 211 reads and manages the medicine dispensing data including at least the name of a patient who takes medicines and the times of medication.

For example, the pack data management system 212 and the medicine dispensing data management system 213 may be implemented as the management application 211 in the PC 210. As illustrated in FIG. 19, a system may include the medicine dispensing apparatus 200 and the PC 210 and performs management by communicating with the medicine dispensing apparatus 200. The management application 211 reads the medicine dispensing data file 219 that is externally produced at a pharmacy or the like where medicines are supplied based on the prescription given by a doctor and includes, for example, times at which medicines are dispensed and medicine information for each patient who takes medicines. The management application 211 reads the data output from the configuration file 217 in which, for example, the setting information set to the PC 210 on a temporary basis is recorded.

For example, a file to be output as log file 216 according to what has been changed or a medicine dispensing history file 215 in which medicine dispensing history is tracked is the data to be output from the management application 211 as necessary. Further, the multiple reports 218 are output as necessary from the PC 210 through the management application 211. The functions such as of the management application 211 of the PC 210 may be arranged in the medicine dispensing apparatus 200.

In other words, in the medicine dispensing data management system 213, the results of medicine dispensing or the change history are stored as record. By so doing, the actual medicine dispensing results are stored as traceability information. This enables a review when a problem occurs.

The pack data management system 212 performs management based on the medication-related information of the medicine pack including at least the name of a patient who takes medicines and the times of medication. However, no limitation is indicated thereby, and a supplementary explanation of the operation of, for example, the medicine dispensing apparatus 200 described as above is given below. As illustrated in FIG. 15A and FIG. 15B, the pickup device 50 is provided with the upper QR code reader 66 and the lower QR code reader 67 in the medicine dispensing apparatus 200. The pickup device 50 moves close to one of the multiple cartridges 10 that stores a medicine pack such as the medicine package 2 and the bound medicine packages 2A, and the QR CODE that indicates the medication-related information 6*c* can be read by the upper reader unit 66*a* of the upper QR code reader 66.

When the medication-related information 6*c* is indicated on the surface of the medicine package 2, the QR CODE is visible through the pack pickup slot 17, and the QR code is read by the upper reader unit 66*a* of the upper QR code reader 66. When the medication-related information 6*c* is displayed on the left support portion 13 on the bottom wall of one of the multiple cartridges 10 as illustrated in FIG. 16, the medication-related information 6*c* is displayed around the pack pickup slot 17. Accordingly, the QR CODE that indicates the medication-related information 6*c* can be read by the upper reader unit 66*a* of the upper QR code reader 66 in a similar manner to the above.

As illustrated in FIG. 18 (see also FIG. 9B for reference purposes), also when the pickup device 50 moves to a position above desired one of the multiple subdivision boxes 34 of the medicine dispensing tray 30 while holding one of the multiple medicine packages 2 picked up from one of the multiple cartridges 10, the QR CODE that indicates the medication-related information 6*c* can be read by the lower reader unit 67*a* of the lower QR code reader 67 in a similar manner to the above. Accordingly, the data read by the upper QR code reader 66 or the lower QR code reader 67 is sent to the pack data management system 212 provided for the PC 210, through the communication module 214.

As illustrated in FIG. 15A and FIG. 15B, the pickup device 50 is provided with the upper QR code reader 66 and the lower QR code reader 67, the name of a patient who takes medicines and the current position of the cartridge 10 in which the medicine pack to be taken by the patient who takes medicines can be detected by the movement of the pickup device 50 in the medicine dispensing apparatus 200 (see, for example, FIG. 1A and FIG. 1B). In other words, when the QR CODE on one of the multiple cartridges 10 is read by the upper QR code reader 66 to obtain the position coordinates of the cartridge 10 in the medicine dispensing apparatus 200 corresponding to the current position of the cartridge 10, the position coordinates of the pickup device 50 corresponding to the current position of the cartridge 10 can be linked to the QR CODE that indicates the medication-related information 6*c*. In the position coordinates of the cartridge, for example, X, Y, and Z indicate the rows, columns, and stages, respectively.

Figure 20:
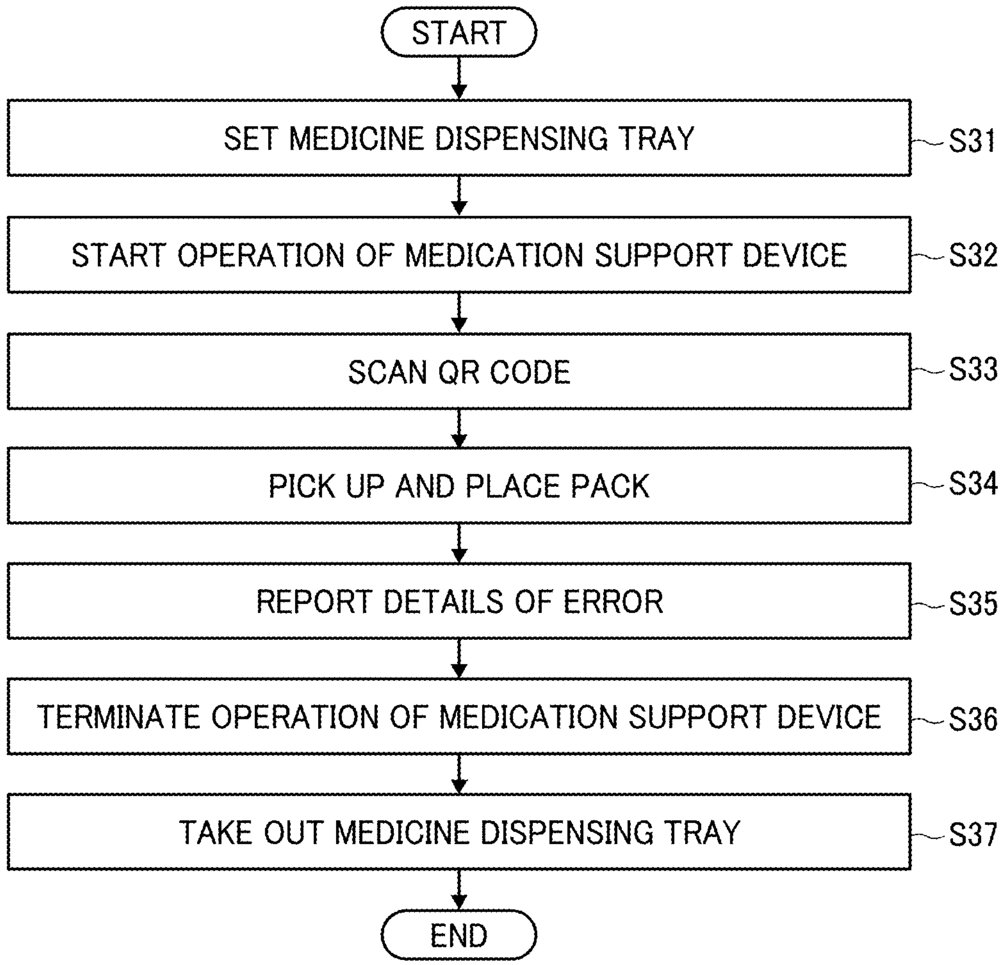
FIG. 20 is a flowchart of an entire operation in which a process with abnormalities is skipped and a medicine dispensing operation continues.

FIG. 20 is a flowchart of the entire operation in which a process with abnormalities is skipped and the medicine dispensing operation continues in the medication support device 300.

As illustrated in FIG. 20, the medicine dispensing tray 30 illustrated in FIG. 3 is placed at a prescribed position of one of the medicine dispensing areas 29 of the medicine dispensing apparatus 200 illustrated in FIG. 1A and FIG. 1B, by a user including, for example, a nurse practitioner and care worker who is a staff in a day-care center or nursing home. Subsequently, in step S31 and step S32, the operation of the medication support device 300 as illustrated in FIG. 19 is started by touching or pressing down the start-up switch 155 of FIG. 11 or by touching or pressing down another start-up switch arranged on the PC 210 side of the medication support device 300 as illustrated in FIG. 19 or the medication support device 300 is automatically started at a predetermined time using at timer or clocking function, and the touch panel 151 of FIG. 11 is operated. By so doing, various kinds of settings are changed.

Subsequently, the pickup device 50 is moved to a position under desired one of the cartridges 10 by the conveyor 90, and in step S33, the QR CODE is read by the upper reader unit 66*a* of the upper QR code reader 66 as illustrated in FIG. 16. The QR-code reading operation using the upper reader unit 66*a* of the upper QR code reader 66 under such circumstances is not limited to the QR-code reading operation illustrated in FIG. 16. For example, the medication-related information 6*c* may be printed on the medicine package 2 stored in the cartridge 10, or the medication-related information 6*c* on the QR code of the label pasted on the casing of the drawer 21 may be scanned and read.

Subsequently, the picking operation is performed as illustrated in FIG. 8A to FIG. 8F and the pickup device 50 sucks up and picks up one of the medicine packages 2 placed at a lower position of one of the cartridges 10, and the medicine package 2 that is picked up by the pickup device 50 is conveyed by the conveyor 90 to desired one of the rooms 33 or the subdivision boxes 34 of the medicine dispensing tray 30 in one of the medicine dispensing areas 29 of FIG. 1A and FIG. 1B. In so doing, the QR-code reading operation using the lower reader unit 67*a* of the lower QR code reader 67 is firstly performed before the medicine package 2 is inserted into desired one of the rooms 33 or the subdivision boxes 34 of the medicine dispensing tray 30. Subsequently, as illustrated in FIG. 17, the QR-code reading operation is performed on the QR CODE of the label 7 with a QR code, which is pasted onto one of the rooms 33 or the subdivision boxes 34 of the medicine dispensing tray 30 to indicate the medication-related information 6*c*.

Subsequently, in step S34, a placing operation is performed as illustrated in FIG. 9B, and the medicine package 2 is inserted into desired one of the rooms 33 or the subdivision boxes 34 of the medicine dispensing tray 30.

When abnormalities in operation are detected in steps S31 to S34, in step S35, the details of the error are reported by, for example, at least one of the loudspeaker and the light of the notification unit 154 illustrated in FIG. 11. After the details of the error are reported, in step S36, the medication support device 300 stops operating. After the medication support device 300 stops operating, in step S37, the medicine package 2 that is inserted into desired one of the rooms 33 or the subdivision boxes 34 of the medicine dispensing tray 30 is taken out.

When abnormalities in operation are detected midway in steps S31 to S34, the details of the error to be reported are stored in the built-in memory 152 of FIG. 11 as necessary, and a user is notified of the details of the error through the display unit and the notification unit 154 of the touch panel 151 of FIG. 11 after the medication support device 300 stops operating. When the QR CODE cannot be read due to dirt or the like and a timeout occurs, it is determined by the CPU illustrated in FIG. 11 that an error or abnormality in the QR-code reading operation is present.

An error notification method is described below with reference to FIG. 21 to FIG. 27. FIG. 21 to FIG. 27 are diagrams each of which illustrates an example display screen 220 of a management application 211 related to an error notification method.

The configuration or structure of the management application 211 is described above with reference to FIG. 19. An example is described below in which abnormalities including, for example, an error occurred during the medicine dispensing operation are displayed on the management application 211 after the medicine dispensing operation is completed.

Figure 21:
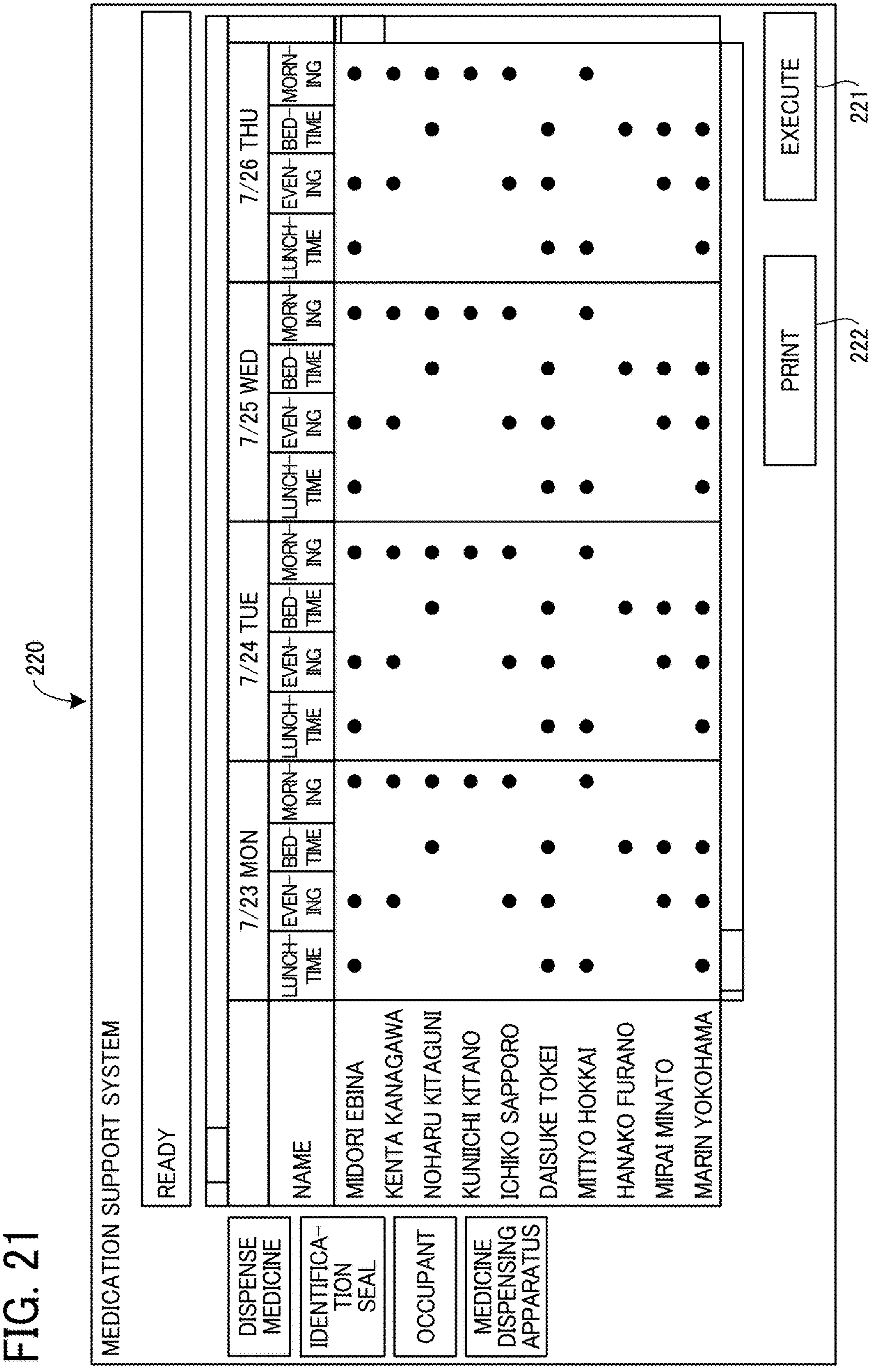
FIG. 21 is a diagram illustrating an example display screen related to an error notification method.

FIG. 21 is a diagram illustrating the display screen 220 of the management application 211, displaying an initial screen before the medicine dispensing operation.

FIG. 22 is a diagram illustrating the display screen 220 of the management application 211, displaying a screen when the medicine dispensing operation is to be executed.

As illustrated in FIG. 22, the date for medication or the times of medication (lunchtime, evening, bedtime, morning) for each occupant or patient who takes medicines can be selected, and the medicine dispensing operation can be started by touching or pressing down an execute key 221 at the bottom right of the screen. By touching or pressing down a print key 222 at the bottom-right corner of the screen, the operation in progress can be displayed and printed.

Figure 23:
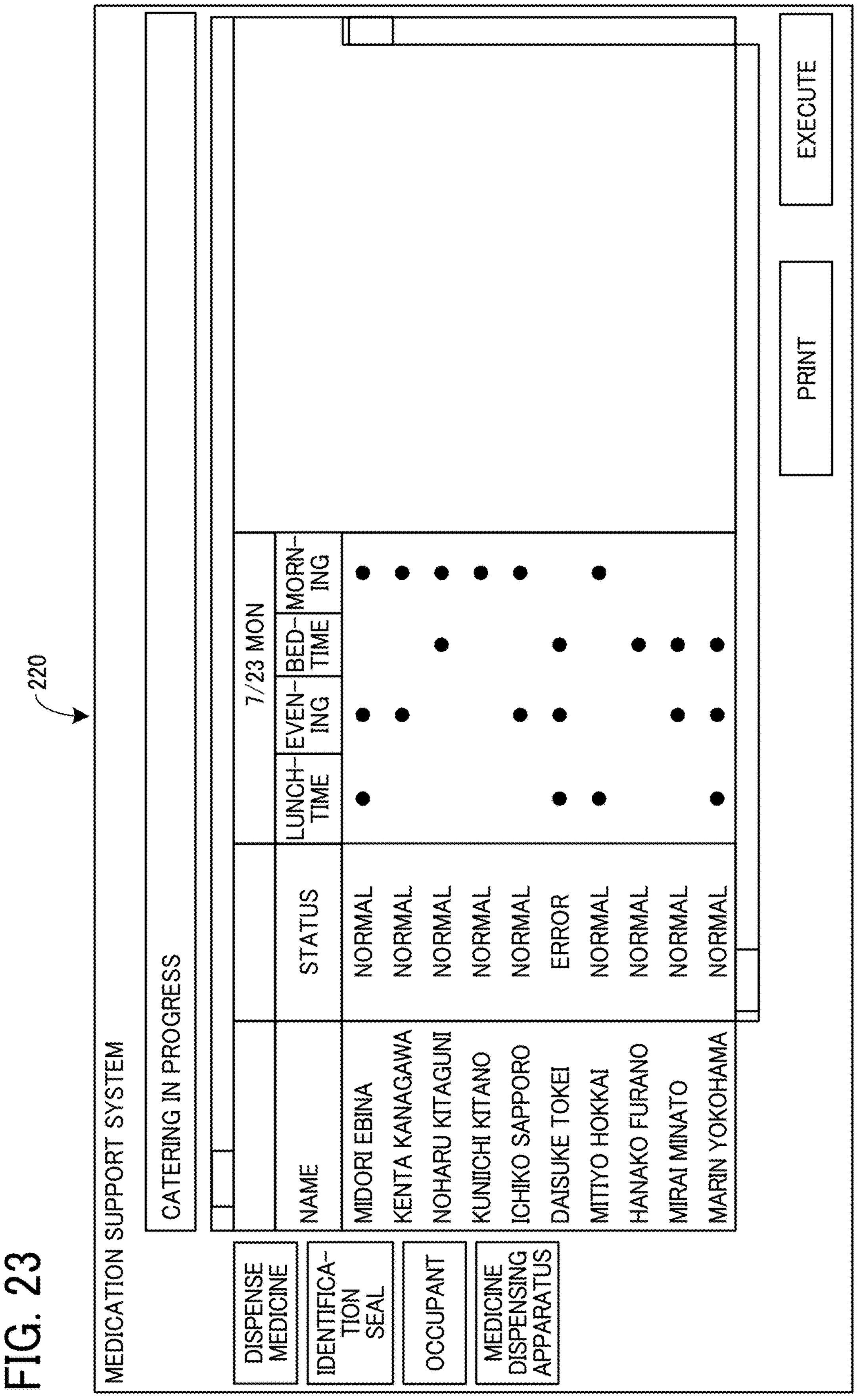
FIG. 23 is still another diagram illustrating an example display screen related to an error notification method.

FIG. 23 is a diagram illustrating the display screen 220 during a medicine dispensing operation.

For example, when the medicine dispensing operations are to be started at lunchtime on July 23 (MON), the medicine dispensing operations are performed in the order listed from Midori Ebina. When it comes to the medicine dispensing operations in the evening and the picking-up operation of the medicine package 2 from the cartridge 10 for Daisuke Tokei is not successful, such an error is displayed in the column of "status" on the screen.

Figure 24:
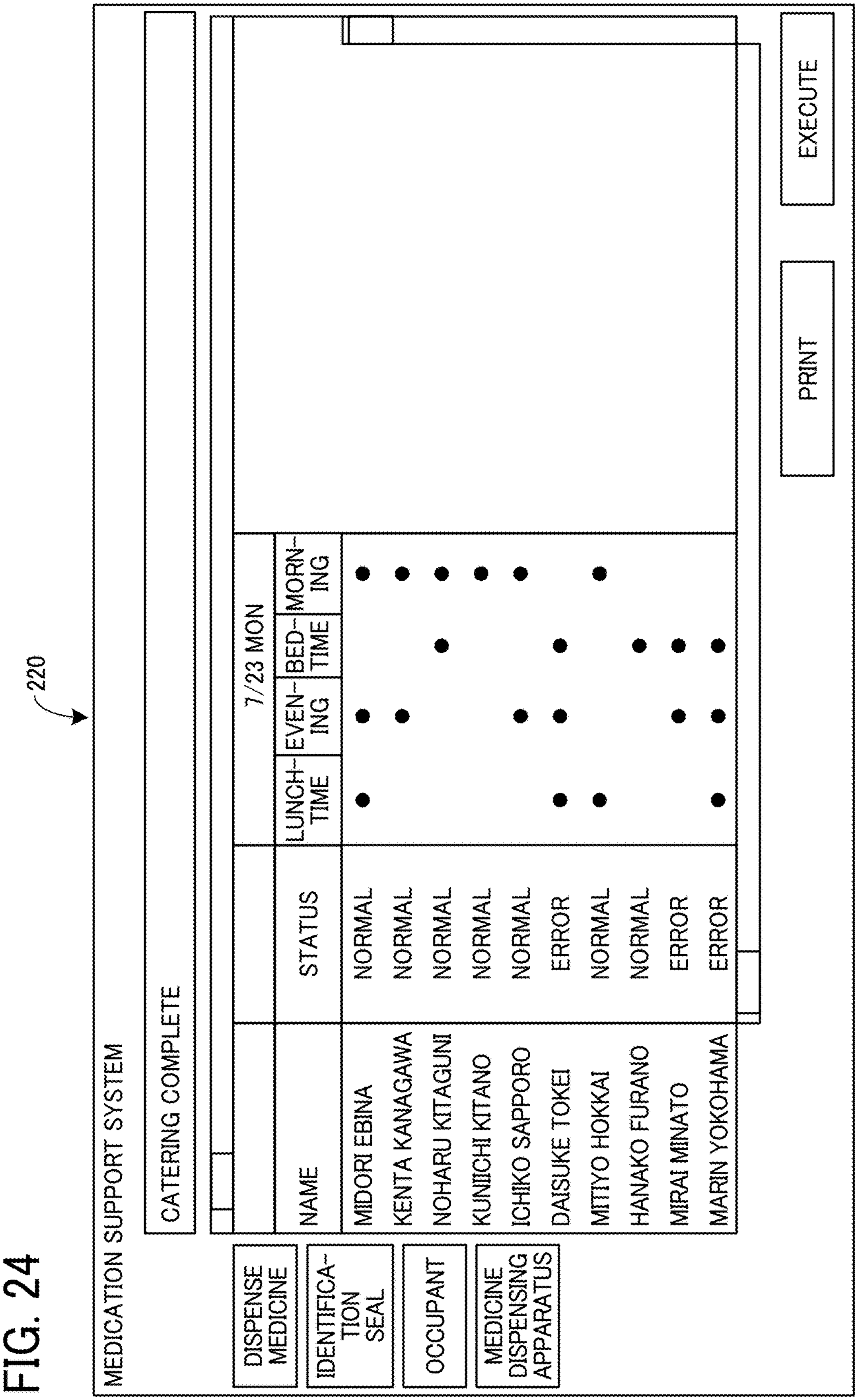
FIG. 24 is still another diagram illustrating an example display screen related to an error notification method.

In FIG. 24, Mirai Minato is indicated as error because the medicine package 2 dropped midway, and Marin Yokohama is indicated as error because the QR-code reading operation was not successful. As the QR-code reading operation is performed before the picking operation and placing operation and the presence or absence of an error is apparent in advance, an error may be displayed on the display screen 220 of the management application 211 from the beginning.

Figure 25:
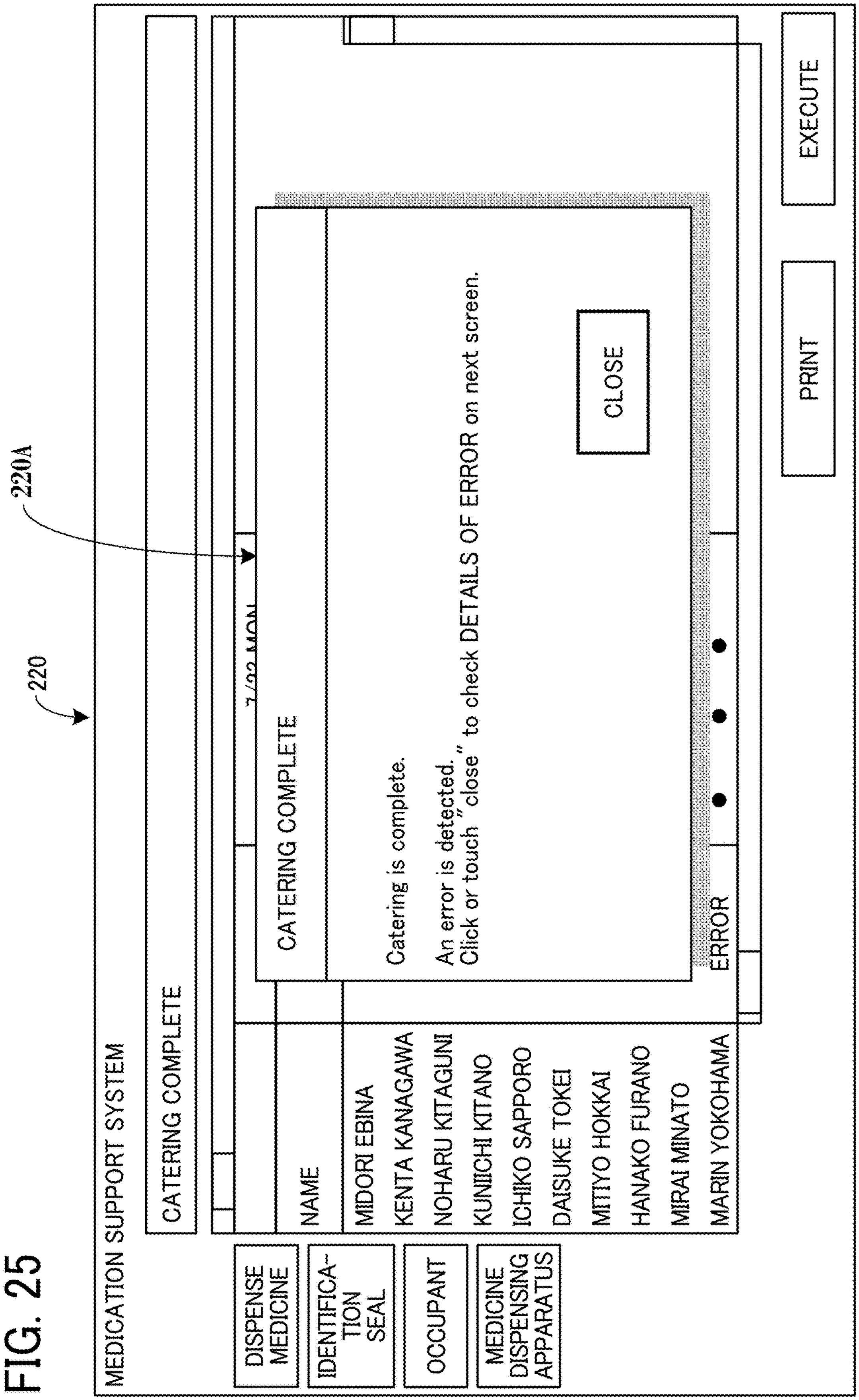
FIG. 25 is still another diagram illustrating an example display screen related to an error notification method.
Figure 26:
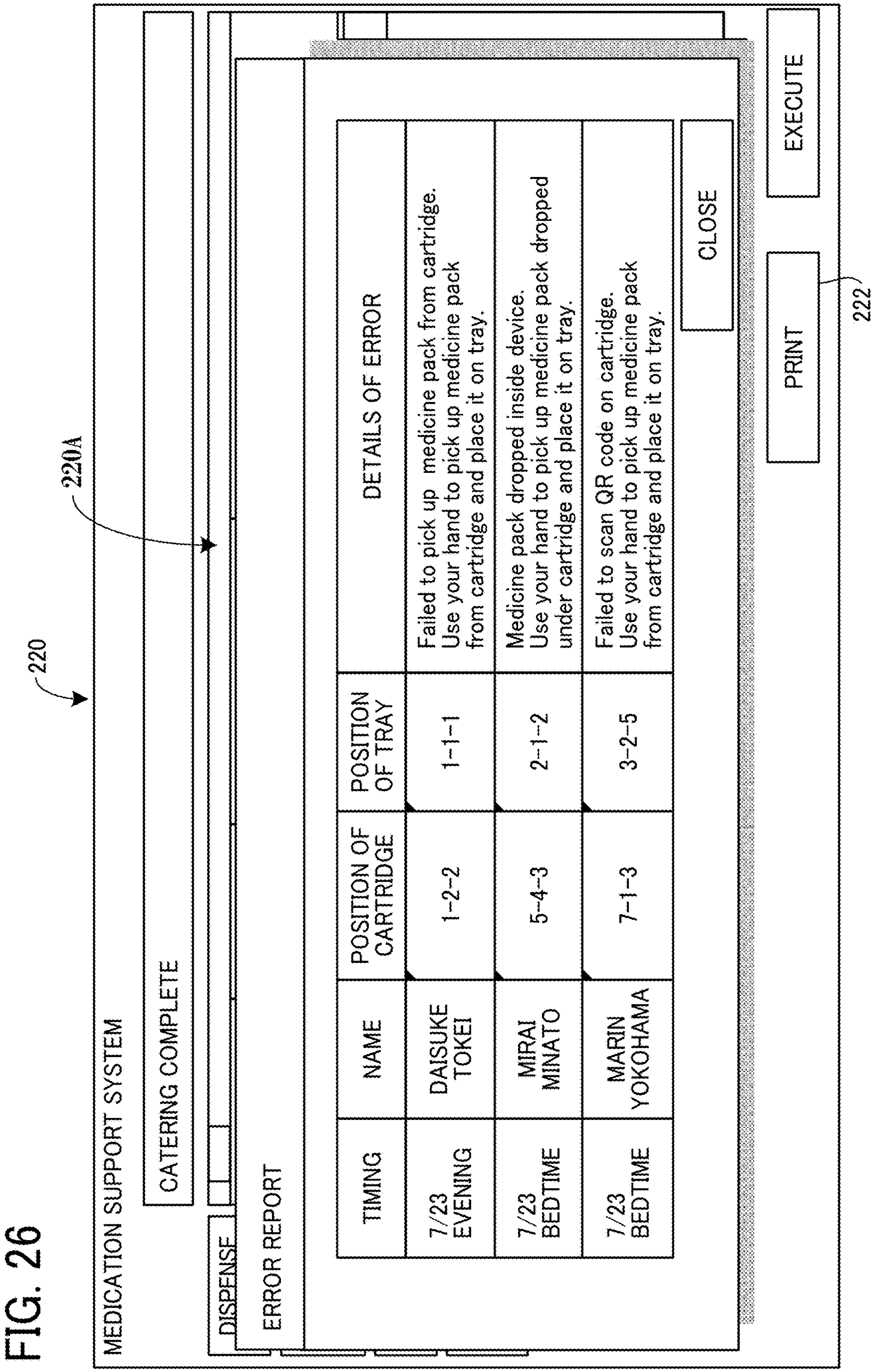
FIG. 26 is still another diagram illustrating an example display screen related to an error notification method.

On the management application 211, a window 220A is displayed on the display screen 220 as illustrated in FIG. 25 after all the medicine dispensing operation is completed. Due to such a configuration, the user is notified that there is an error. When the display of the display screen 220 is further advanced, what actually happened in the error can be checked as illustrated in FIG. 26. The items to be displayed include, for example, the time of error occurrence, the name of each occupant, the position of the cartridge 10 or the subdivision box 34 of each occupant, and the details of the error.

When the picking-up operation for the medicine package 2 containing the medicine is not successful or the QR-code reading operation is not successful, the position inside the medicine dispensing apparatus 200 at which the cartridge 10 is stored can be identified based on the position of the cartridge 10 that stores the medicine package 2. The medicine package 2 containing the medicine 3 may be taken out from the identified position, and may manually be dispensed to the subdivision box 34.

When the medicine package 2 is dropped inside the medicine dispensing apparatus 200, how the pack was being conveyed is displayed on the display screen 220 for check. Due to such a configuration, the dropped medicine package 2 can be sought and found out. By displaying errors on the display screen 220 all at once at last for notification as described above, errors can collectively be dealt with, and a user can work on other tasks during the medicine dispensing operation with the medicine dispensing apparatus.

Figure 27:
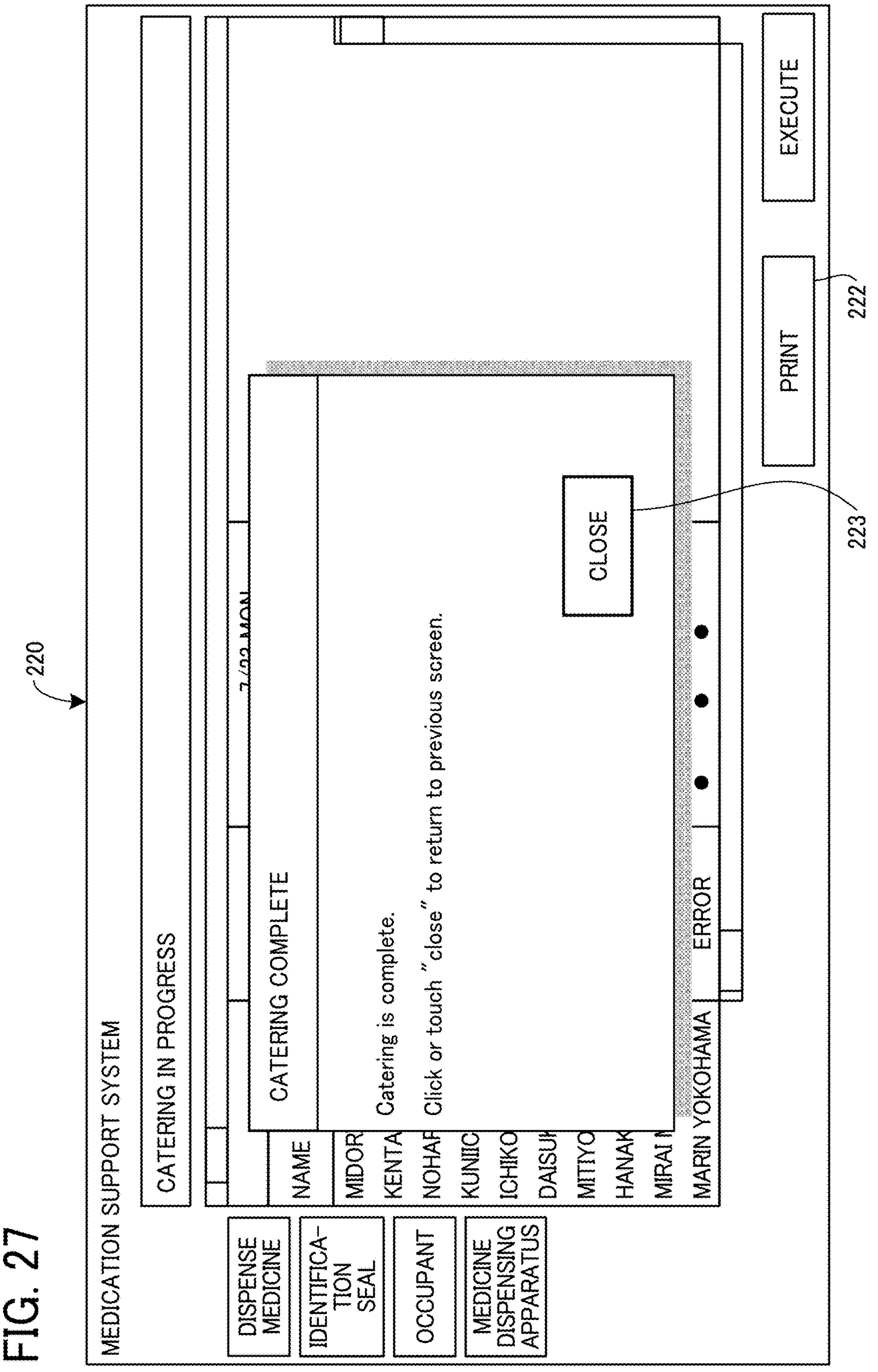
FIG. 27 is still another diagram illustrating an example display screen related to an error notification method.

FIG. 27 is a diagram illustrating the display screen 220 when the operation is successfully completed with no error.

Figure 28:
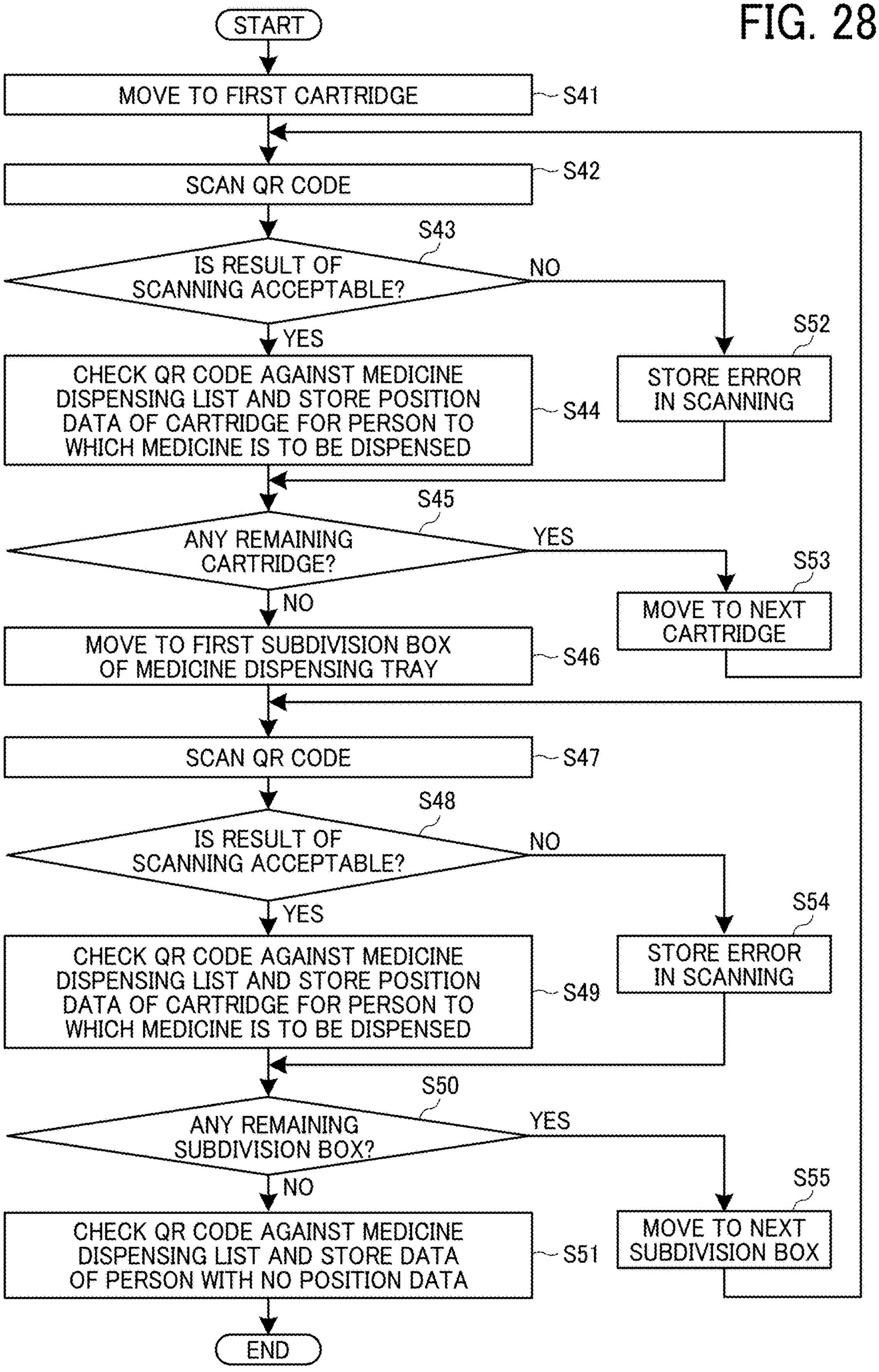
FIG. 28 is a flowchart of an operation in which a QR code is read.

FIG. 28 is a flowchart of an operation in which a QR code is read.

The medication-related information 6*c* on the cartridge 10 or the medicine dispensing tray 30 is read and obtained using the medication-related information reader unit 65 of the pickup device 50. As in the following description, the label 7 with a QR code pasted onto the subdivision box 34 of the medicine dispensing tray is read. The medication-related information 6*c* of the QR CODE on the cartridge 10 or the medication-related information 6*c* of the label 7 with a QR code on the subdivision box 34 is represented by alphanumeric codes linked to a person to which medicine is to be dispensed. Due to such a configuration, the medication-related information 6*c* may include text data of times of medication or the names of occupants.

As the conveyor 90 operates, in step S41 and step S42, the medication-related information reader unit 65 of the pickup device 50 moves to each one of the cartridges 10 such as each one of the first to n-th cartridges, and scans and reads a QR code. At the position where the label 7 with a QR code is read, the QR code indicating the medication-related information 6*c* is scanned and read using the upper QR code reader 66 of the medication-related information reader unit 65. When the result of this reading operation is appropriate and acceptable in step S43, in step S44, the read QR CODE is compared to the position data of the cartridge 10 for a person to which medicine is to be dispensed who is listed in the medicine dispensing list, and the position data of the cartridge 10 is stored.

Subsequently, in step S45, whether there is some remaining cartridge 10 is checked. When there is no remaining cartridge, in step S46, the conveyor 90 operates and the pickup device 50 moves to a position substantially directly above the first subdivision box 34 of medicine dispensing tray 30.

Subsequently, in step S47, the medication-related information reader unit 65 of the pickup device 50 moves to a position above desired one of the multiple subdivision boxes 34 of the medicine dispensing tray 30, which corresponds to the first one of the cartridges 10, and scans and reads the QR code indicating the medication-related information 6*c*, using the lower QR code reader 67 of the medication-related information reader unit 65. When the result of this reading operation is appropriate and acceptable in step S48, in step S49, the read QR CODE and the position data of the subdivision box 34 for a person to which medicine is to be dispensed who is listed in the medicine dispensing list are stored. Subsequently, in step S50, whether there is some remaining subdivision box 34 is checked. When there is no remaining subdivision box (NO in step S50), in step S51, the result of reading the read QR CODE is compared to a person to which medicine is to be dispensed who is listed in the medicine dispensing list and the data of a person with no position data is stored.

On the other hand, when the result of the reading operation for the cartridge 10 is inappropriate and not acceptable (NO in step S43), in step S52, an error in scanning is stored, and the process proceeds to step S45. More specifically, in step S52, a person to which medicine is to be dispensed who has no position data for the cartridge 10 is not treated as a person to which medicine is to be dispensed, and an error in scanning a QR code is reported in the notification of an error after the medicine dispensing operation. More specifically, an error includes at least one of a failure to attach the cartridge 10 to the drawer 21, dirt on the QR CODE, and misalignment of the QR CODE.

When there is some remaining cartridge 10 (YES in step S45), in step S53, the pickup device 50 moves to the next cartridge 10 as the conveyor 90 operates, and the operations in S42 and the following steps are repeated.

On the other hand, in step S48, when the result of the reading operation for the subdivision box 34 is inappropriate and not acceptable, the process proceeds to step S54 to store a reading error, and the process shifts to the processes in the step S50.

More specifically, in step S54, a person to which medicine is to be dispensed who has no position data for the subdivision box 34 is not treated as a person to which medicine is to be dispensed, and an error in scanning a QR code is reported in the notification of an error after the medicine dispensing operation. More specifically, an error includes at least one of a failure to attach the subdivision box 34 to the room 33 of the medicine dispensing tray 30, dirt on the QR CODE, and misalignment of the QR CODE.

When there is some remaining subdivision box 34 (YES in step S50), in step S55, the pickup device 50 moves to the next subdivision box 34 as the conveyor 90 operates, and the operations in S47 and the following steps are repeated.

Figure 29:
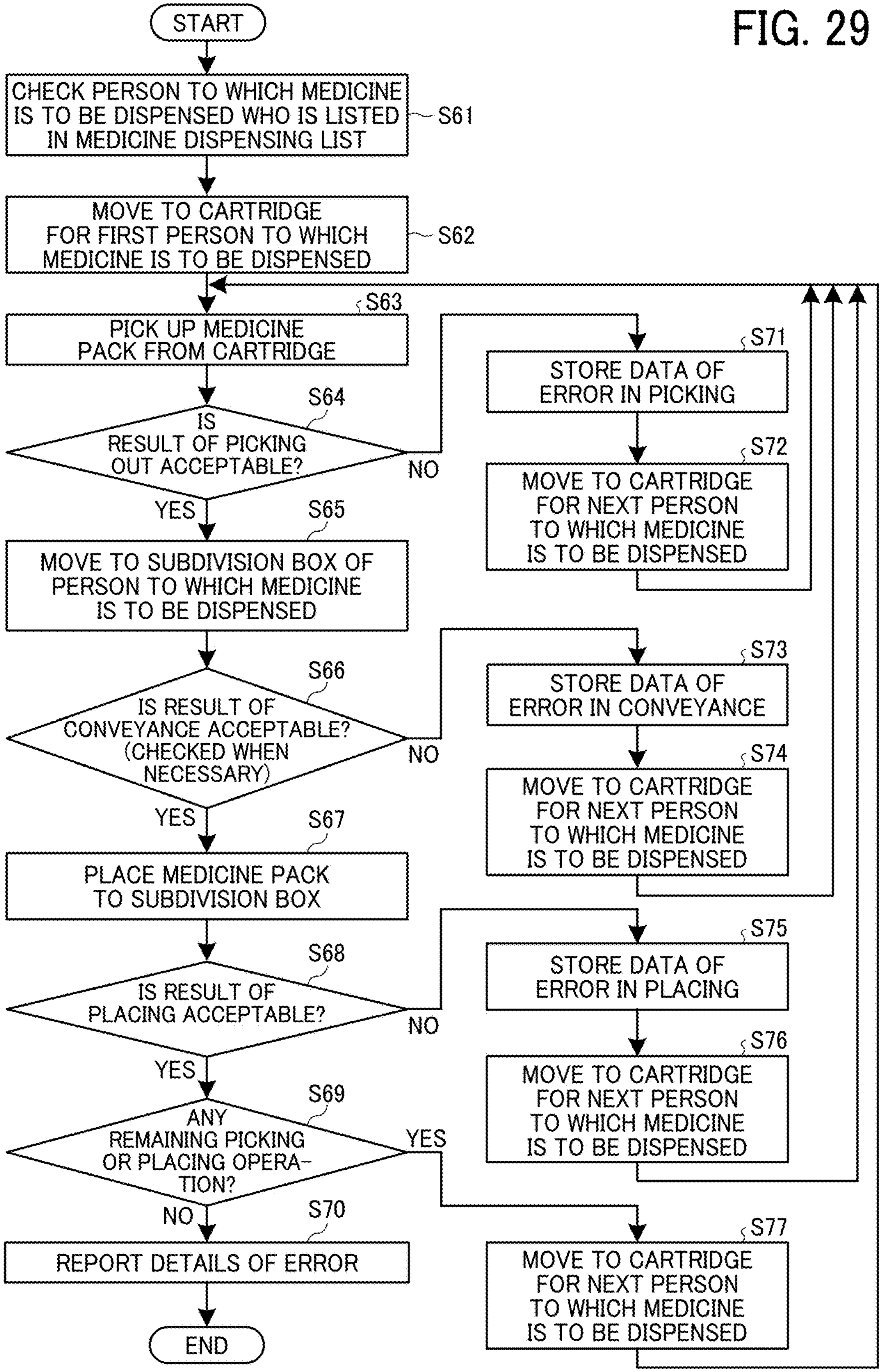
FIG. 29 is a flowchart of a picking operation and placing operation.

FIG. 29 is a flowchart of a picking operation and placing operation.

As illustrated in FIG. 29, the medicine package 2 containing the medicine 3 for a person to which medicine is to be dispensed is picked up from the cartridge 10 based on the position data of the cartridge 10 or the subdivision box 34 obtained by the QR-code reading operation depicted in FIG. 28, and is dispensed to one of the subdivision boxes 34. When an error occurs during the medicine dispensing operation, the medicine dispensing operation is once terminated. Subsequently, the error is recorded, and the medicine dispensing operation for the next person to which medicine is to be dispensed is performed. Then, the process proceeds to the last person to which medicine is to be dispensed, and the notification of the error is displayed.

As an air suctioning mechanism is employed, a pressure sensor 126 is arranged in an air path as will be described later in detail with reference to, for example, FIG. 32. When the pressure sensor 126 fails to detect a certain level of negative pressure, it is determined that there is an error in the picking out operation as depicted in FIG. 29.

When the pressure sensor 126 detects that the negative pressure is equal to or higher than a certain level, it is determined that there is an error in conveyance and the medicine package 2 is dropped.

A pack sensor 127 with feelers is arranged near the pair of suction pads 52 as will be described later in detail with reference to, for example, FIG. 30A and FIG. 30B, and when the pack sensor 127 is still turned on even after the instructions for vacuum breakdown are given, it is determined that there is an error in placing and there is a remaining medicine package 2 on the pair of suction pads 52.

In the picking operation and placing operation described above with reference to FIG. 29, firstly, the medicine package 2 containing the medicine for a person to which medicine is to be dispensed is picked up from the cartridge 10 based on the position data of the cartridge 10 or the subdivision box 34 of the medicine dispensing tray 30, which is obtained by an operation in which a QR code is read as illustrated in FIG. 28. Subsequently, through the conveyance of the pickup device 50 by the conveyor 90, the medicine package 2 is moved to a position substantially directly above the subdivision box 34 for the person to which medicine is to be dispensed, and the medicine package 2 is dispensed and inserted into the subdivision box 34. When an error occurs during the medicine dispensing operation, the medicine dispensing operation is once terminated. Subsequently, the error is recorded, and the medicine dispensing operation for the next person to which medicine is to be dispensed is performed. Then, the process proceeds to the last person to which medicine is to be dispensed, and the notification of the error is displayed.

As illustrated in FIG. 29, the processes in the picking operation start from step S61. In step S61, the persons to which medicine is to be dispensed who are listed in the medicine dispensing list are checked, and then in step S62, the pickup device 50 is moved by the conveyor 90 to a position under the cartridge 10 that stores the medicine package 2 for the first person to which medicine is to be dispensed. Subsequently, in step S63, the picking operation is performed to pick up one of the medicine packages 2 from the cartridge 10, and in step S64, whether the result of the picking out operation is acceptable is checked.

When the result of the picking out operation is acceptable (YES in step S64), in step S65, the pickup device 50 is moved by the conveyor 90 to a position substantially directly above the subdivision box 34 for the person to which medicine is to be dispensed, together with the suction device 51 that sucks and holds the medicine package 2 of the first person to which medicine is to be dispensed. At that moment in time, in step S66, whether the result of the conveyance of the medicine package 2 that has been conveyed to a position substantially directly above the subdivision box 34 for the person to which medicine is to be dispensed is acceptable or not acceptable is determined as appropriate.

When the result of the conveyance of the medicine package 2 is acceptable in step S66, in step S67, a placing operation is performed. In such a placing operation, vacuum breakdown is performed for the pair of suction pads 52 of the suction device 51 that suck and hold the medicine package 2, and the medicine package 2 is inserted into the subdivision box 34. When the placing operation is successfully performed and the result of the placing operation is acceptable (YES in step S68), in step S69, whether there is some remaining picking or placing operation for a person to which medicine is to be dispensed is checked. When there is no remaining picking or placing operation for a person to which medicine is to be dispensed (NO in step S69), the process proceeds to step S70, and the details of the error are reported all at once.

When the result of the picking out operation is not acceptable in step S64, in step S71, the data of the error of the picking operation is stored in, for example, the built-in memory 152 of the controller 150 of FIG. 11. Then, in step S72, the pickup device 50 is moved by the conveyor 90 to the cartridge 10 for the next person to which medicine is to be dispensed, and the process returns to the step S63, and the picking operation from the cartridge 10 and the following operations are repeated.

When the result of the conveyance of the medicine package 2 that has been conveyed to the subdivision box 34 for the person to which medicine is to be dispensed is not acceptable in step S66, in step S73, the data of the error of the conveying operation is stored in, for example, the built-in memory 152 of the controller 150 of FIG. 11. Then, in step S74, the pickup device 50 is moved by the conveyor 90 to the cartridge 10 for the next person to which medicine is to be dispensed, and the process returns to the step S63, and the picking operation from the cartridge 10 and the following operations are repeated.

When the placing operation is not successfully performed and the result of the placing operation is not acceptable in step S68, in step S75, the data of the error of the placing operation is stored in, for example, the built-in memory 152 of the controller 150 of FIG. 11. Then, in step S76, the pickup device 50 is moved by the conveyor 90 to the cartridge 10 for the next person to which medicine is to be dispensed, and the process returns to the step S63, and the picking operation from the cartridge 10 and the following operations are repeated.

When there is some remaining picking or placing operation for a person to which medicine is to be dispensed (YES in step S69), the process proceeds to step S77, and the pickup device 50 is moved by the conveyor 90 to the cartridge 10 for the next person to which medicine is to be dispensed. Then, the process returns to the step S63, and the picking operation from the cartridge 10 and the following operations are repeated.

Figures 30A, 30B:
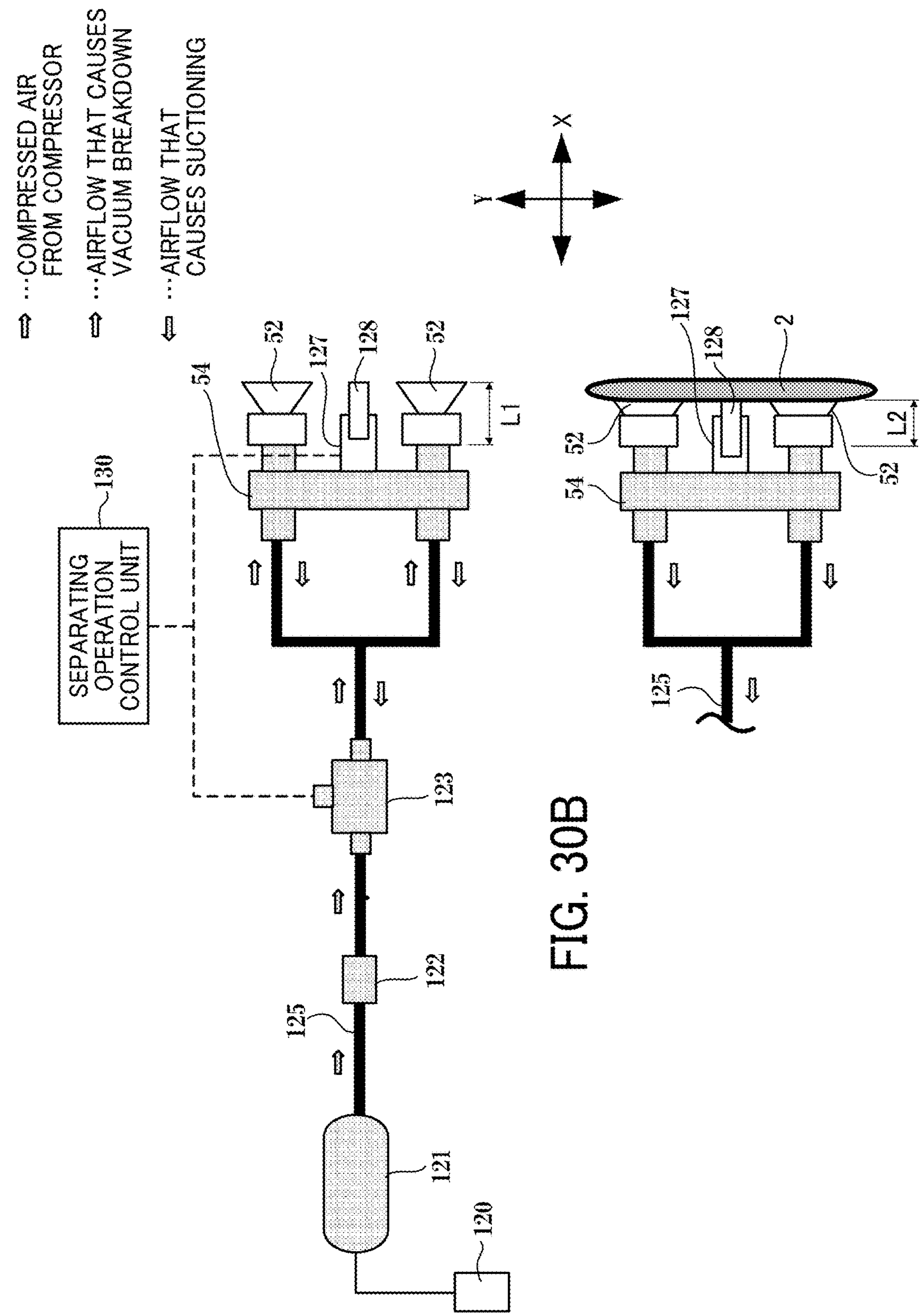
FIG. 30A and FIG. 30B are schematic diagrams each illustrating an air duct that detects a dropped pack and a configuration and operation of a pack sensor.

FIG. 30A and FIG. 30B are schematic diagrams each illustrating an air duct 125 that detects a dropped pack and a configuration and operation of a pack sensor 127.

In FIG. 30A and FIG. 30B, the compressed air accumulated in the compressor 121 is maintained at a level equal to or greater than a certain level by the power that is intermittently given from a compressor controller 120, and air with a desired level of pressure and flow rate is supplied through a regulator 122. The vacuum ejector valve 123 is controlled by the power and signals from the separating operation control unit 130, and causes suctioning or vacuum breakdown using the compressed air from the compressor 121. The airflow that causes suctioning or vacuum breakdown is schematically indicated by arrows in FIG. 30A and FIG. 30B.

The air duct 125 bifurcates into two around the right end in the drawing of the vacuum ejector valve 123, and is connected to the pair of suction pads 52 fixed to the suction-pad supporting member 54. When the medicine package 2 is to be picked up, the pair of suction pads 52 are arranged symmetrically in pairs across a line of symmetry, and the line of symmetry is the center line of the medicine package 2. In a similar manner to the configuration or structure described above with reference to FIG. 7B, in FIG. 30A and FIG. 30B, the pair of suction pads 52 are arranged in a row at a certain distance in the Y-axis direction.

In a similar manner to the above, the pack sensor 127 that is fixed to the suction-pad supporting member 54 is arranged between the pair of suction pads 52. The pack sensor 127 is an example of a sensor that detects a dropped pack using a pushrod. As illustrated in FIG. 30B, the pack sensor 127 is turned on when a rod 128 that is pressed against the medicine package 2 sucked and held by the pair of suction pads 52 is pushed in by a predetermined amount, and the separating operation control unit 130 that has received a signal determines that the medicine package 2 is being held. In FIG. 30A, the medicine package 2 is not held by the pair of suction pads 52. In this case, the size of the pair of suction pads 52 in height is L1, and the front end of the rod 128 and the end faces of the pair of suction pads 52 are on an approximately same imaginary plane.

In FIG. 30B, the operation of the pack sensor 127 when the medicine package 2 is present is indicated. In FIG. 30B, the medicine package 2 is sucked and held by the pair of suction pads 52, and the rod 128 is pushed in. At that moment in time, the pair of suction pads 52 are compressed by negative pressure, and their size in height becomes L2. More specifically, the medicine package 2 are held at a position retracted by L1-L2 from the end faces of the pair of suction pads 52 in FIG. 30A. The rod 128 that contacts the medicine package 2 is also pushed in by L1-L2, and the pack sensor 127 is turned on. As a result, it is detectable that the air inside the air duct 125 is kept under vacuum and the medicine package 2 is held. In other words, the CPU of FIG. 11 determines that the medicine package 2 is not dropped as it is sucked and held by the pair of suction pads 52, based on the ON signal from the pack sensor 127.

As long as it is detectable that the medicine package 2 is being held, detection may be performed at any point of the medicine package 2. The sensor is not limited to a contact sensor such as the pack sensor 127, and a non-contact sensor like an optical sensor 129 as will be described later in detail with reference to FIG. 31 may be adopted. When the optical sensor 129 is adopted, it is not necessary for the sensor to be arranged on the suction-pad supporting member 54.

Cases in which a sensor that detects a dropped pack is used as the optical sensor 129 are described below with reference to FIG. 31. More specifically, how the optical sensor 129 detects the droppage of the medicine package 2 is described below.

In the pickup device 50 that includes the pair of suction pads 52, when the suction holding of one of the multiple medicine packages 2 by the pair of suction pads 52 is to be released, so-called vacuum breakdown in which negative pressure is changed to atmospheric pressure is performed by ejecting a small amount of air using the vacuum ejector valve 123 (see FIG. 9B). If the pressure of vacuum breakdown under such circumstances is strong, one of the multiple medicine packages 2 is unintentionally blown off and cannot be placed in predetermined one of the multiple rooms 33. On the contrary, if the pressure of vacuum breakdown under such circumstances is weak, one of the multiple medicine packages 2, which is light in weight, unintentionally sticks to the pair of suction pads 52 due to static electricity. In either case, each one of the multiple medicine packages 2 does not orderly drop and fall into the predetermined one of the multiple rooms 33 (or the subdivision boxes 34) of one of the multiple medicine dispensing trays 30 with reliability.

Figure 31B:
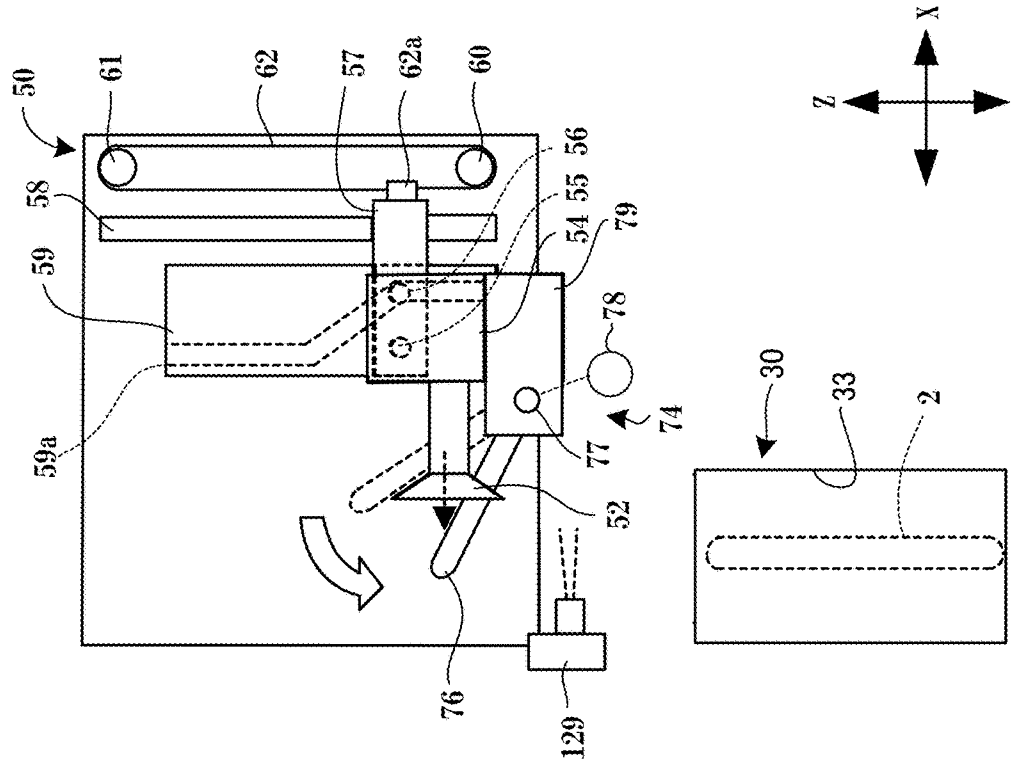
FIG. 31B is a side view of the pickup device of FIG. 31A.
Figure 31A:
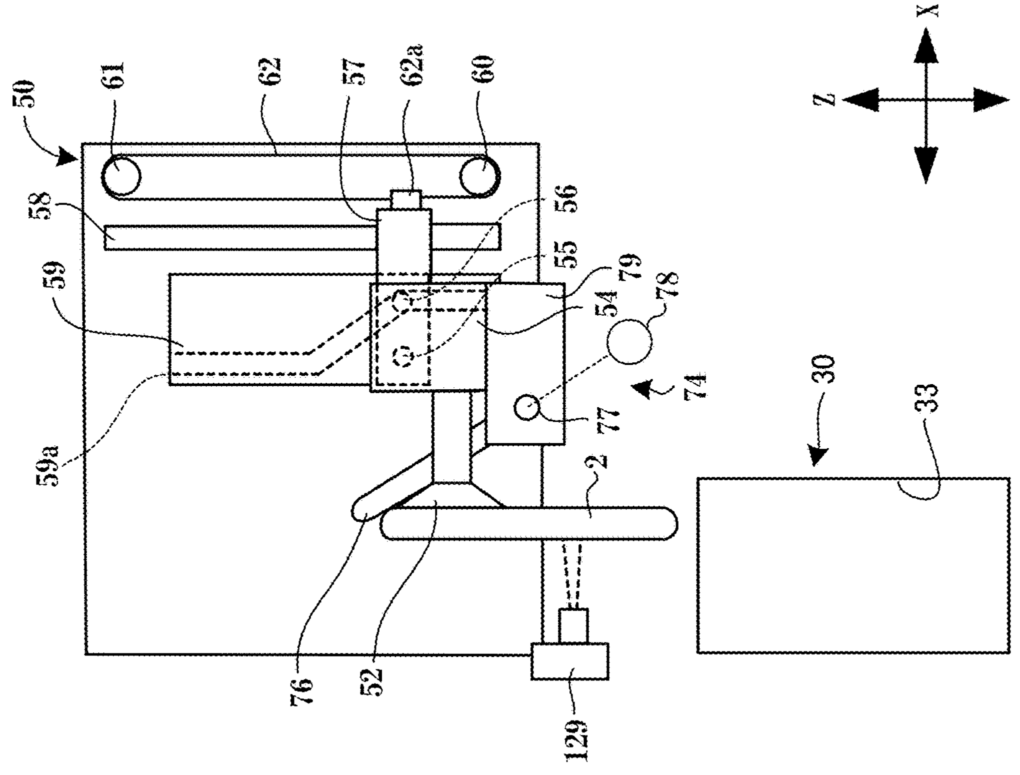
FIG. 31A is a front view of a pickup device, illustrating its configuration or structure and separating operation to force a medicine package to take off from a pair of suction pads.

FIG. 31A is a front view of the pickup device 50, illustrating its configuration or structure and separating operation to force the medicine package 2 to take off from the pair of suction pads 52.

FIG. 31B is a side view of the pickup device 50 illustrated in FIG. 31A.

The pickup device 50 as illustrated in FIG. 31 is different from the pickup device 50 of the medicine dispensing apparatus 200 illustrated in, for example, FIG. 7A and FIG. 7B, in that the separating operation control unit 130 surrounded by a broken line in FIG. 11 is used, and the other configurations or operations of the present embodiment are equivalent to the configuration or structure and operations described above with reference to FIG. 7A and FIG. 7B.

The separating operation control unit 130 of the medicine dispensing apparatus 200 provided with the pickup device 50 performs control based on the signal from the optical sensor 129 in place of the signal from the pack sensor 127. The CPU controls the operation of the vacuum ejector valve 123 through a vacuum ejector driver 124, and controls the operation of a drive motor 78, which drives the separating member 76 that is an example of an actuator for the separator, through the motor drivers each of which is an example of a driver for the separator.

In other words, the CPU determines whether the medicine package 2 is successfully separated at a prescribed timing based on the signal from the optical sensor 129, and controls the vacuum ejector valve 123 and the drive motor 78 in accordance with the result of such determination. By so doing, elements are controlled to operate in cooperation with each other step by step.

The pickup device 50 illustrated in FIG. 31A is provided with a separator 74 that includes a separating member 76 slightly above the pair of suction pads 52. The separating member 76 performs separating operation to force the medicine package 2 to take off from the pair of suction pads 52. The separating member 76 is an example of a biasing member and is shaped like a lever. In the pickup device 50, the separating operation that forces one of the medicine packages 2 to be separate from the pair of suction pads 52 is performed based on the signal from the optical sensor 129, by the separating member 76 that is an example of a biasing member that pushes the medicine package 2.

As a sensor that detects the medicine package that is dropped from the pair of suction pads 52, the optical sensor 129 that adopts a non-contact method and detects the optical reflection is used. The optical sensor 129 is arranged such that its exit light is incident upon a relatively lower portion of the medicine package 2 that is sucked and held by the pair of suction pads 52, and detects whether the medicine package 2 is sucked and held by the pair of suction pads 52. The optical sensor 129 that adopts a non-contact method offers a high degree of flexibility in place of installation. In other words, if a laser sensor or the like that can perform multi-directional detection with relatively long detection distance is used for various parts of the medicine package 2, the sensor may be arranged at various kinds of places such as portions of the medicine dispensing tray 30 or the housing 199 other than portions of the pickup device 50. As described above, the optical sensor 129 is used as a detection method in which unwanted force is not applied to the medicine package 2 and suctioning or separating processes are not interfered with.

In the operation of the pickup device 50, the medicine package 2 is sucked and vertically held by the pair of suction pads 52 as illustrated in FIG. 31A, and then the operation as illustrated in FIG. 31B is performed. More specifically, the operation of the separator 74 is started after the operation of the vacuum ejector valve 123 (see FIG. 30A and FIG. 30B) is terminated. In other words, the operation of the separator 74 is started after the suction holding of one of the multiple medicine packages 2 by the pair of suction pads 52 is released by vacuum breakdown. As illustrated in FIG. 31B, the separating member 76 is driven to rotate by the rotation of the drive motor 78 in a counterclockwise (CCW) direction indicated by a large hollow arrow to hit an upper portion of the pack to drop the medicine package 2 downward. Accordingly, one of the multiple medicine packages 2 sucked and held in the vertical orientation by the pair of suction pads 52 is forced to be taken off, and is orderly stored in predetermined one of the multiple rooms 33 of one of the multiple medicine dispensing trays 30 as indicated by dotted lines. Subsequently, the drive motor 78 is driven in the reverse direction to stop the operation of the separator 74.

A failure of dropping the medicine package 2 is typically caused by an extreme curled portion of the medicine package 2 on the edge. This is because such a curled portion tends to be caught by the pair of suction pads 52 that serve as a suction unit. Alternatively, a failure of dropping the medicine package 2 is typically caused by the static electricity generated between the suction unit and the medicine package 2. This is because such static electricity tends to make the medicine pack stuck to the suction unit. In order to deal with such a situation, in the present embodiment of the pickup device 50 described above with reference to FIG. 31, the separating member 76 acts on a portion close to a problematic site. Accordingly, the separating operation can successfully be done.

Figure 32:
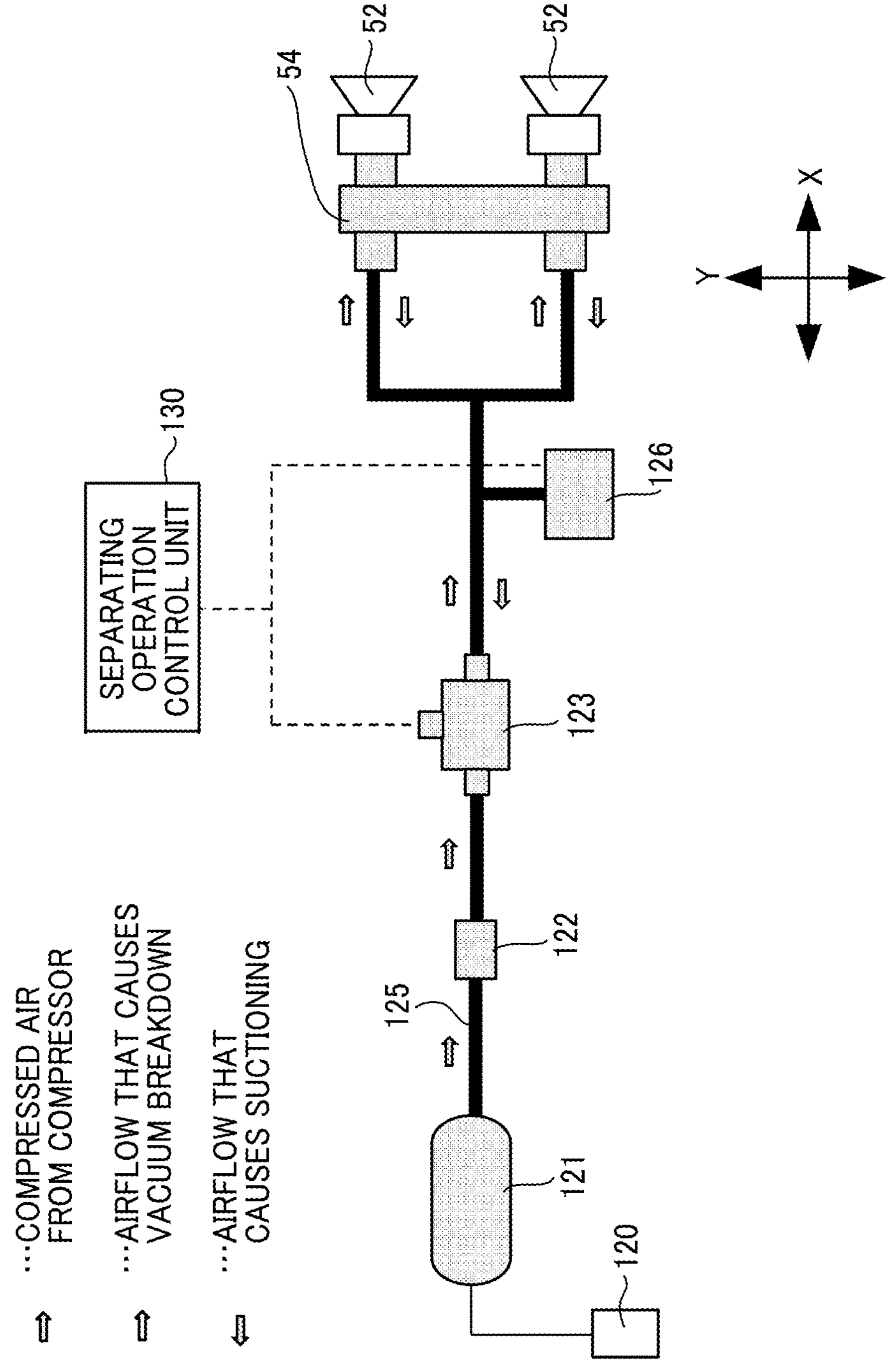
FIG. 32 is another diagram illustrating a sensor that detects a dropped pack.

FIG. 32 is another diagram illustrating a sensor that detects a dropped pack and a method of sensing the suctioning pressure.

In FIG. 32, the compressed air accumulated in the compressor 121 is maintained at a level equal to or greater than a certain level by the power that is intermittently given from the compressor controller 120, and air with a desired level of pressure and flow rate is supplied through the regulator 122. The vacuum ejector valve 123 is controlled by the power and signals from the separating operation control unit 130, and causes suctioning or vacuum breakdown using the compressed air from the compressor 121. The airflow that causes suctioning or vacuum breakdown is schematically indicated by arrows in FIG. 32.

The air duct 125 bifurcates into two around the right end in the drawing of the vacuum ejector valve 123, and is connected to the pair of suction pads 52 fixed to the suction-pad supporting member 54. As a pack sensor, a pressure sensor 126 is arranged between the vacuum ejector valve 123 and the pair of suction pads 52. When the medicine package 2 is sucked by the pair of suction pads 52, negative pressure is generated. When the medicine package 2 is dropped from the pair of suction pads 52 before reaching a prescribed position of the medicine dispensing tray 30, the air is released and the negative pressure gets weakened. By detecting such changes in negative pressure, the droppage of the medicine package 2 can be detected. The installation position of the pressure sensor 126 may be anywhere as long as negative pressure is generated, and may be the determination of bifurcating point around the right end in the drawing of the vacuum ejector valve 123.

A method of giving notification of the droppage location of the medicine package 2 is described below with reference to FIG. 33.

Figure 33B:
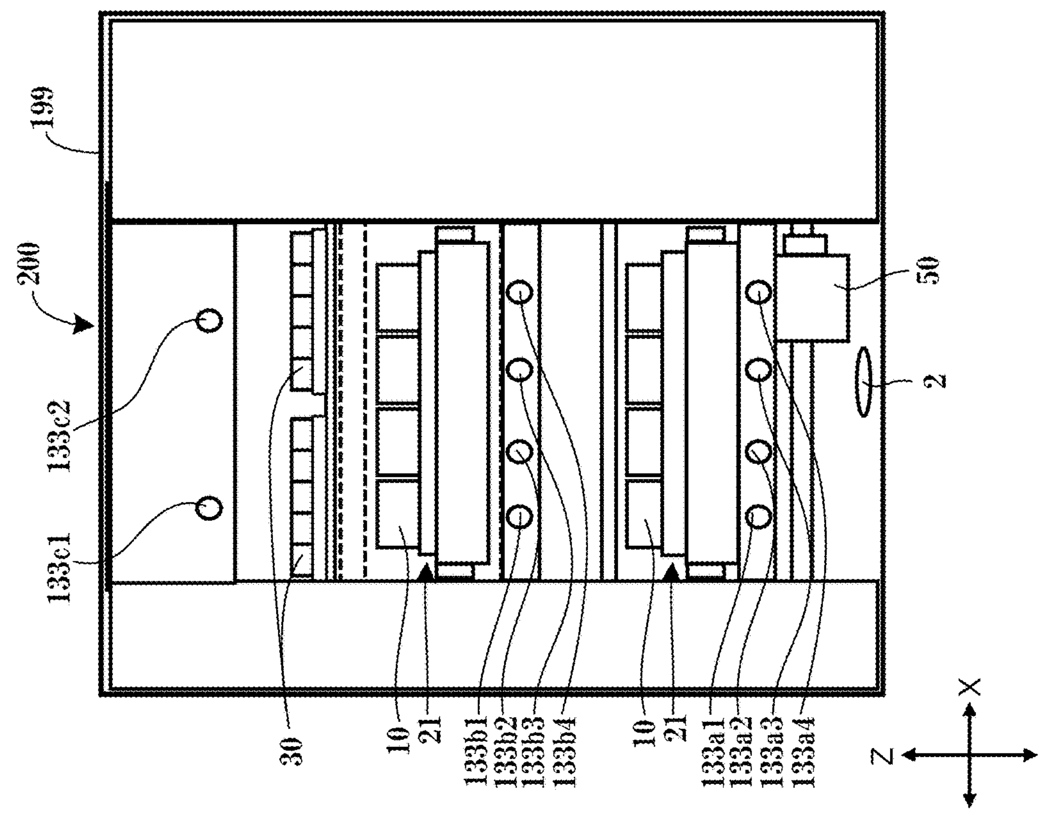
FIG. 33B is a side view of a medicine dispensing apparatus provided with LEDs to give notification of the droppage location of a medicine package.
Figure 33A:
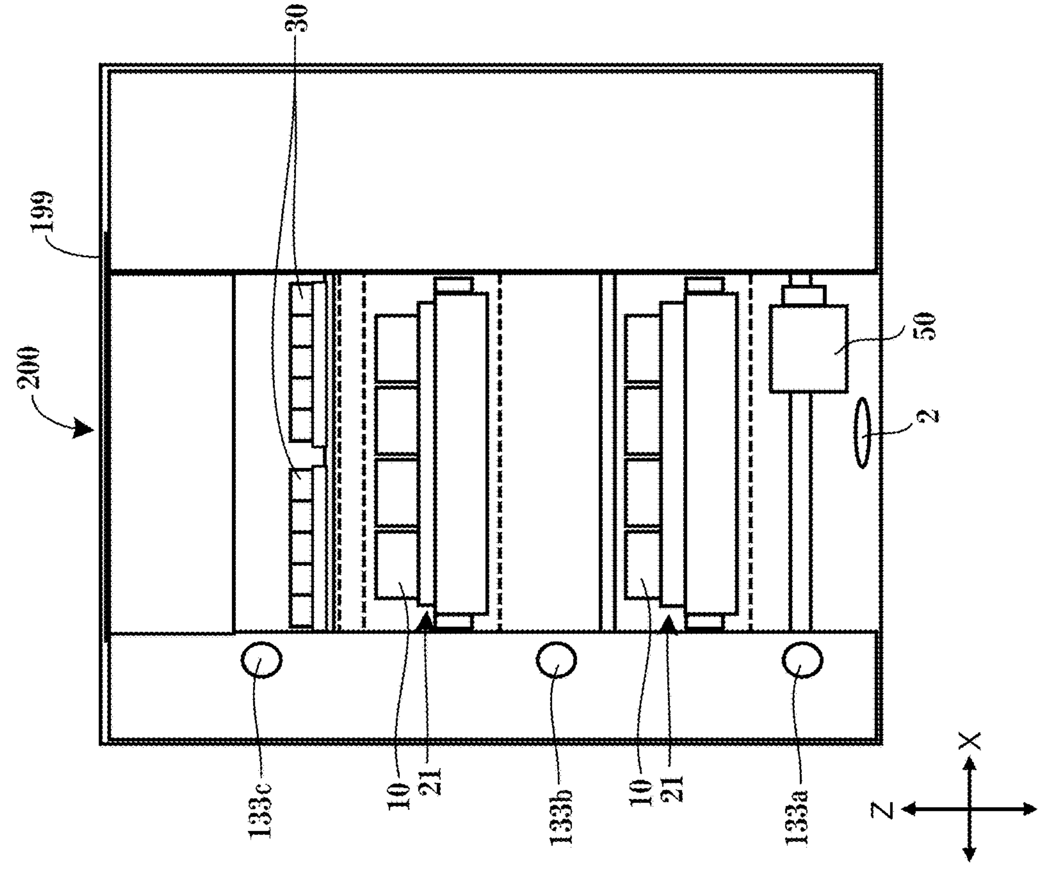
FIG. 33A is a front view of a medicine dispensing apparatus provided with LEDs to give notification of the droppage location of a medicine package.

FIG. 33A is a front view of the medicine dispensing apparatus 200 provided with LEDs 133, each of which is made of a light emitter and serves as a notifier, to give notification of the droppage location of the medicine package 2.

FIG. 33B is a side view of the medicine dispensing apparatus 200 provided with LEDs 133, each of which is made of a light emitter and serves as a notifier, to give notification of the droppage location of the medicine package 2.

The droppage location of the medicine package 2 in the medicine dispensing apparatus 200 can be determined based on the position of the pickup device 50 that performed the picking up operation and the timing at which the pack sensor 127 as illustrated in FIG. 30A and FIG. 30B detected droppage. For example, as illustrated in FIG. 33A, when it is assumed that the medicine package 2 is picked up but dropped at the second position from the right while the pickup device 50 is moving under the cartridges 10 at the lowermost stage of the medicine dispensing apparatus 200 and the droppage of the medicine package 2 is detected by the pack sensor 127 in FIG. 30A and FIG. 30B, it is likely that the medicine package 2 is dropped around a position under that cartridge 10. In that case, an LED 133*a* at the bottom left under the cartridges 10 at the lowermost stage is made to emit light. This allows the user to know where the medicine package 2 is dropped.

As illustrated in FIG. 33A, the LEDs 133 may be distributed to several areas at varying stages. For example, such distributed LEDs include the LED 133*a* arranged near the cartridges 10 at the lowermost stage, an LED 133*b* arranged near the cartridges 10 at an upper stage, and an LED 133*c* arranged near the medicine dispensing tray 30 at the uppermost stage. However, no limitation is intended thereby. As illustrated in FIG. 33B, the LEDs may be distributed to a larger number of areas at varying stages. For example, such distributed LEDs may include LEDs 133*a*1 to 133*a*4 each of which is arranged under one of the cartridges 10 at the lowermost stage, LEDs 133*b*1 to 133*b*4 each of which is arranged under one of the cartridges 10 at an upper stage, and LEDs 133*c*1 and 133*c*2 each of which is arranged above one of the medicine dispensing trays 30 at the uppermost stage.

A method of switching the control mode will be described with reference to FIG. 34 to FIG. 36.

Figure 34:
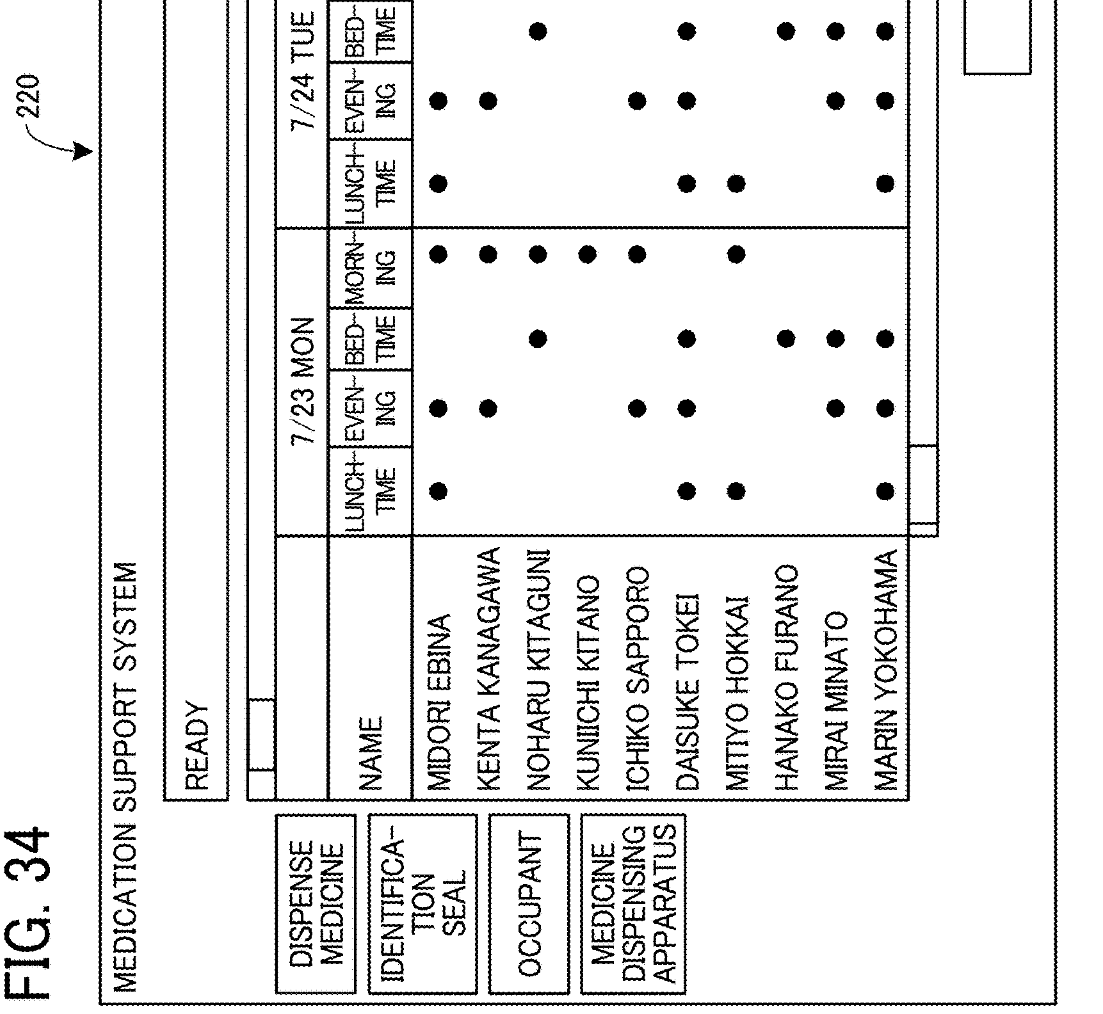
FIG. 34 is a diagram illustrating a display screen provided with two execute keys used to execute a medicine dispensing operation.

FIG. 34 is a diagram illustrating the display screen 220 provided with two execute keys 224 and 225 used to execute a medicine dispensing operation.

Figure 35:
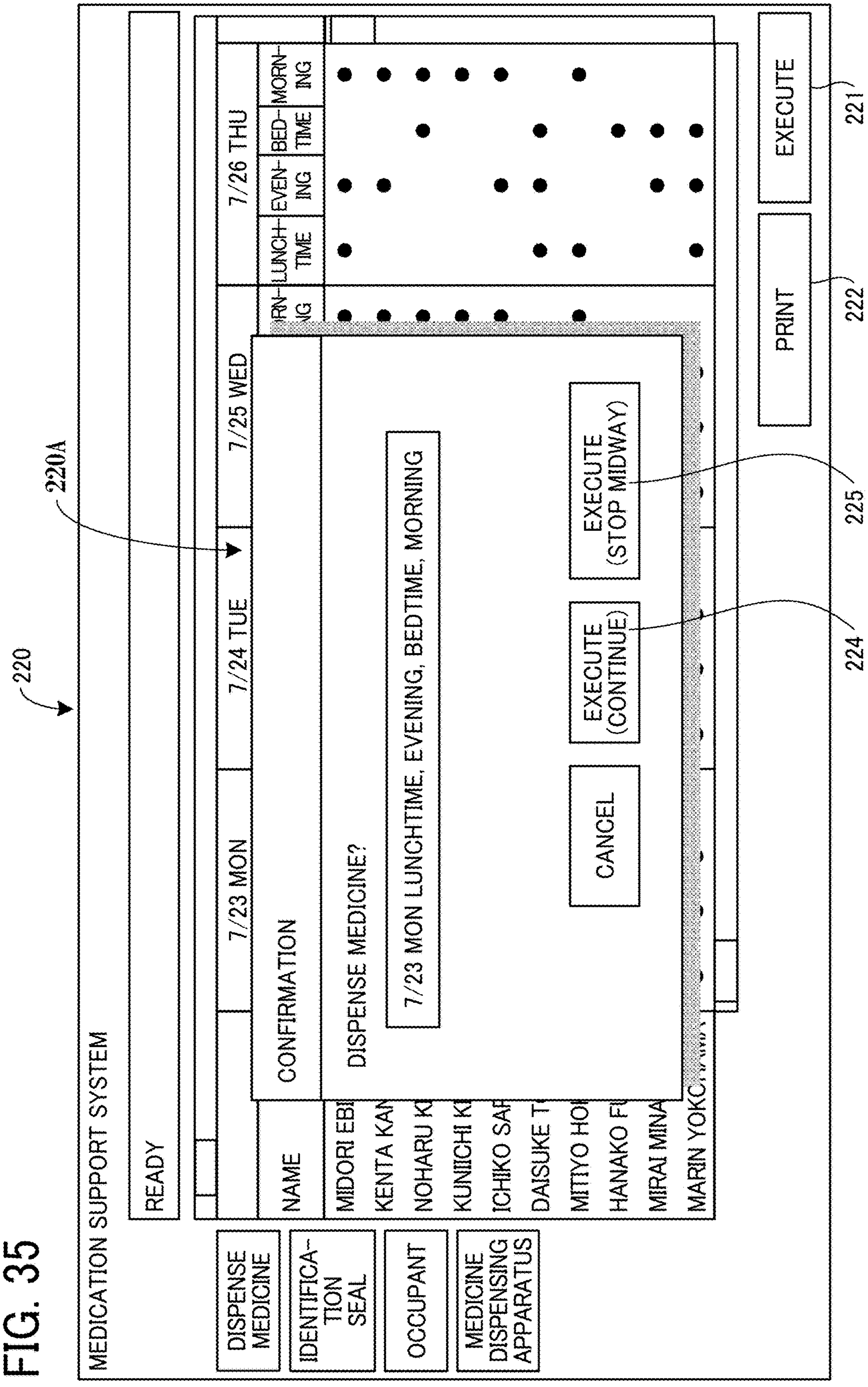
FIG. 35 is a diagram illustrating the display screen 220 on which notification of an error is displayed after a medication support device is paused when the execute (stop midway) key of FIG. 34 is touched or clicked or when an error occurs.

FIG. 35 is a diagram illustrating the display screen 220 on which notification of an error is displayed after a medication support device is paused when the execute (stop midway) key of FIG. 34 is touched or clicked or when an error occurs.

Figure 36:
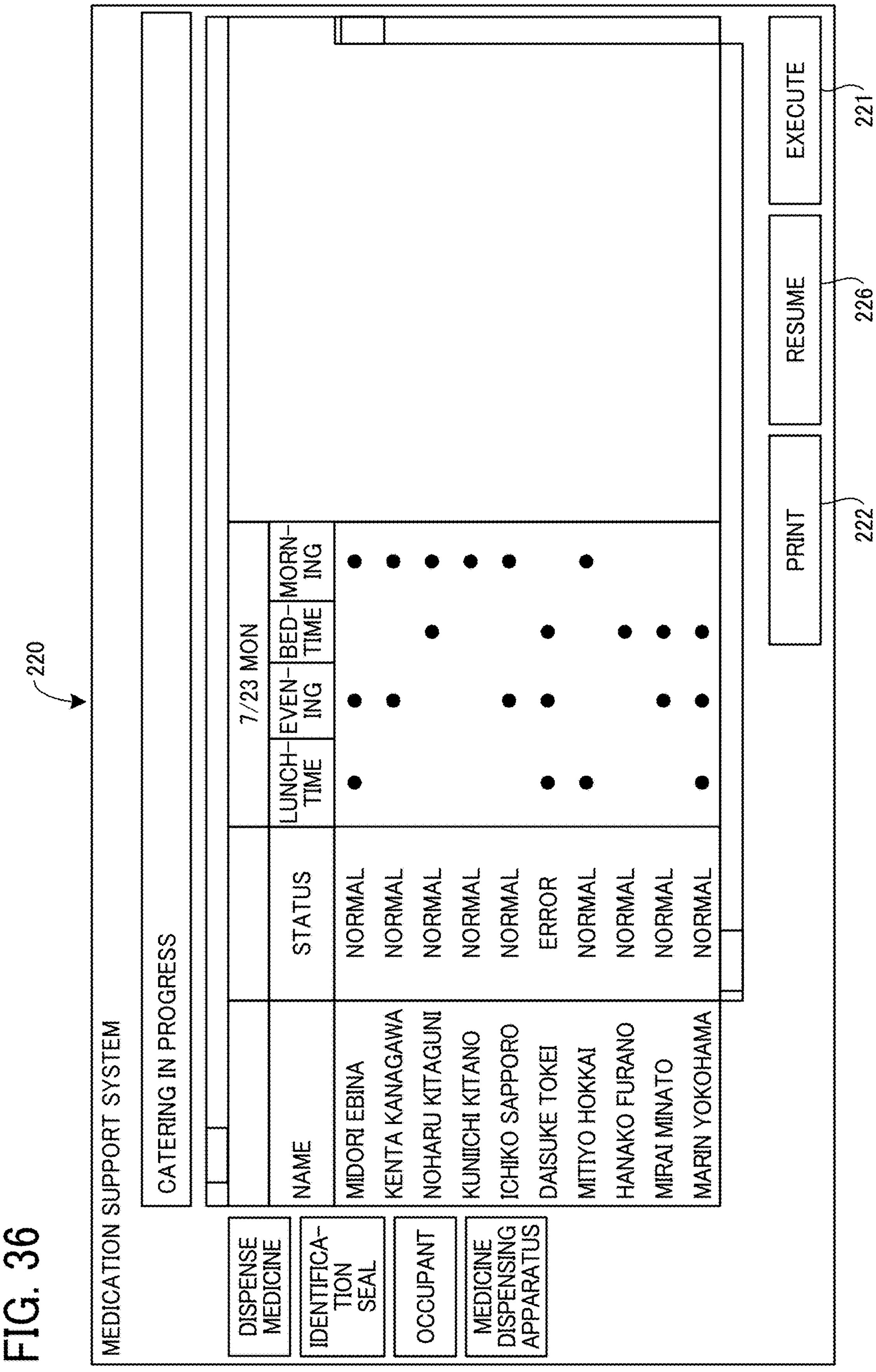

FIG. 36 is a diagram illustrating the display screen 220 provided with a resume key 226 used to execute the next medicine dispensing operation after an error is dealt with.

At the bottom of the display screen of FIG. 34, two execution keys including an execute (continue) key 224 used to execute a medicine dispensing operation and an execute (stop midway) key 225 used to execute a medicine dispensing operation are arranged, and any one of those keys may be chosen and touched or pressed down by a user.

When the user touches or presses down the execute (stop midway) key 225, a medication support device is paused in response to the occurrence of an error, and then the window 220A for the notification of an error is displayed as illustrated in FIG. 35 in a similar manner to the window illustrated in FIG. 26. For example, this enables a user who operates around the medication support device to deal with errors immediately, and the medicine dispensing tray 30 can be taken out immediately after the completion of medicine dispensing operation. For example, the medicine dispensing tray 30 may be passed to a care worker such that he or she can help or assist an occupant to take medication.

After an error is dealt with, the next medicine dispensing operation can be executed by touching or clicking a resume key 226 as illustrated in FIG. 36.

The execute (stop midway) key 225 is displayed on the window 220A as illustrated in FIG. 35, and selectable on the confirmation screen of the window 220A. Due to such a configuration, a similar effect can be achieved.

As described above, the CPU of FIG. 11 uses a pause mode that pauses the medication support device 300 when the medication support device 300 operates abnormally and an operation continue mode that continues the medicine dispensing operation until the medicine dispensing operation for all the persons to which medicine is to be dispensed is completed after the medicine dispensing operation is started. The pause mode is a control mode that is turned on and used when the execute (stop midway) key 225 is touched or pressed down, and the operation continue mode is a control mode that is turned on and used when the execute (continue) key 224 is touched or pressed down. When the medication support device 300 operates abnormally, the CPU may switch the mode between the pause mode and the operation continue mode.

Due to such a configuration, when a user operates around the medication support device, abnormalities in operation are immediately addressed and the time for the operation as a whole can be shortened.

Figure 37:
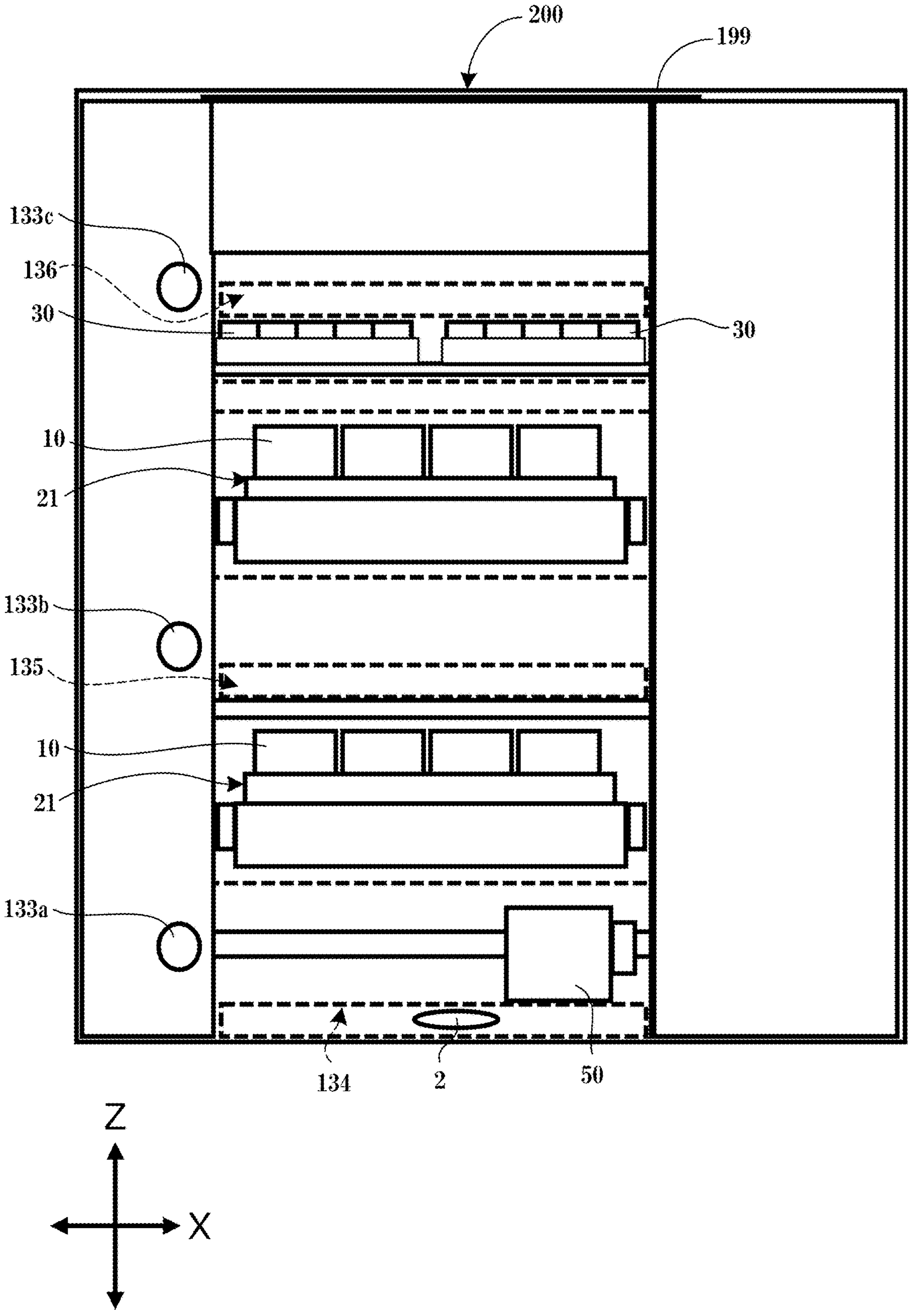
FIG. 37 is a front view of a medication support device in which first spaces for retraction used when a medicine package is dropped are arranged in the conveyance path of a conveyor.

FIG. 37 is a front view of the medicine dispensing apparatus 200 in which first spaces for retraction 134, 135, and 136 used when the medicine package 2 is dropped are arranged in the conveyance path of the conveyor 90.

When the suction device 51 of the pickup device 50 picks up one of the medicine packages 2 from the cartridge 10, there are some cases in which the medicine package 2 is dropped due to lack of suctioning power (see the medicine package 2 dropped to the bottom of the housing 199 of the medicine dispensing apparatus 200 of FIG. 37). If the medicine package 2 is to be picked up under these conditions from the cartridge 10 for the next person to which medicine is to be dispensed, which may be at the same stage but in a different row, the pickup device 50 may contact the dropped medicine package 2 and damage the medicine package 2.

In order to handle such a situation, as illustrated in FIG. 37, the first spaces for retraction 134 and 135 with heights in the vertical direction equal to or greater than the thickness of the medicine package 2 are arranged in the conveyance path of the conveyor 90 to keep and hold the medicine package 2 that is dropped during conveyance by the pickup device 50 and the conveyor 90. Due to such a configuration, the pickup device 50 can travel without contacting the medicine package 2, and damage to the medicine package 2 can be prevented. Each of the first spaces for retraction 134 and 135 is arranged under the cartridges 10. As there are some cases in which the medicine package 2 does not successfully drop into one of the rooms 33 or the subdivision boxes 34, the space for retraction 136 may be arranged above the medicine dispensing tray 30.

Figure 38B:
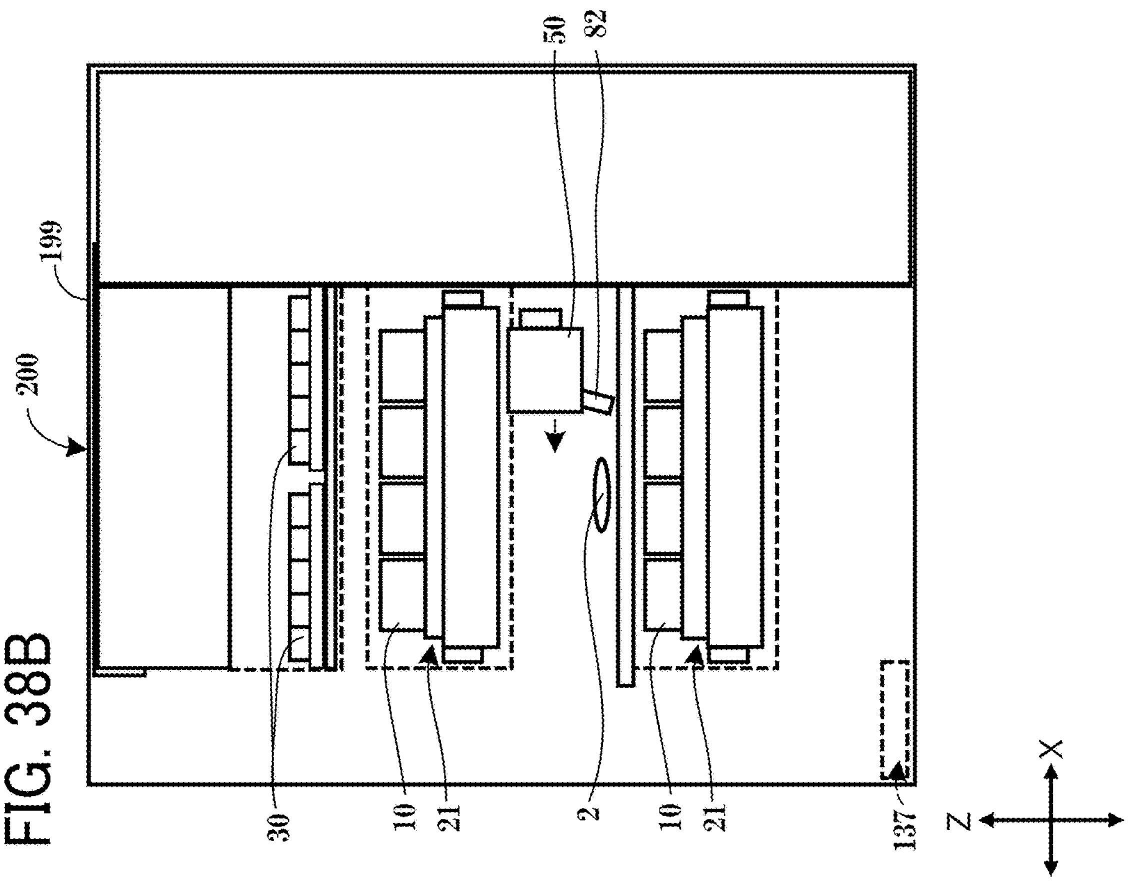
FIG. 38B is another front view of a medicine dispensing apparatus having a guide to guide a medicine package to a second space for retraction.
Figure 38A:
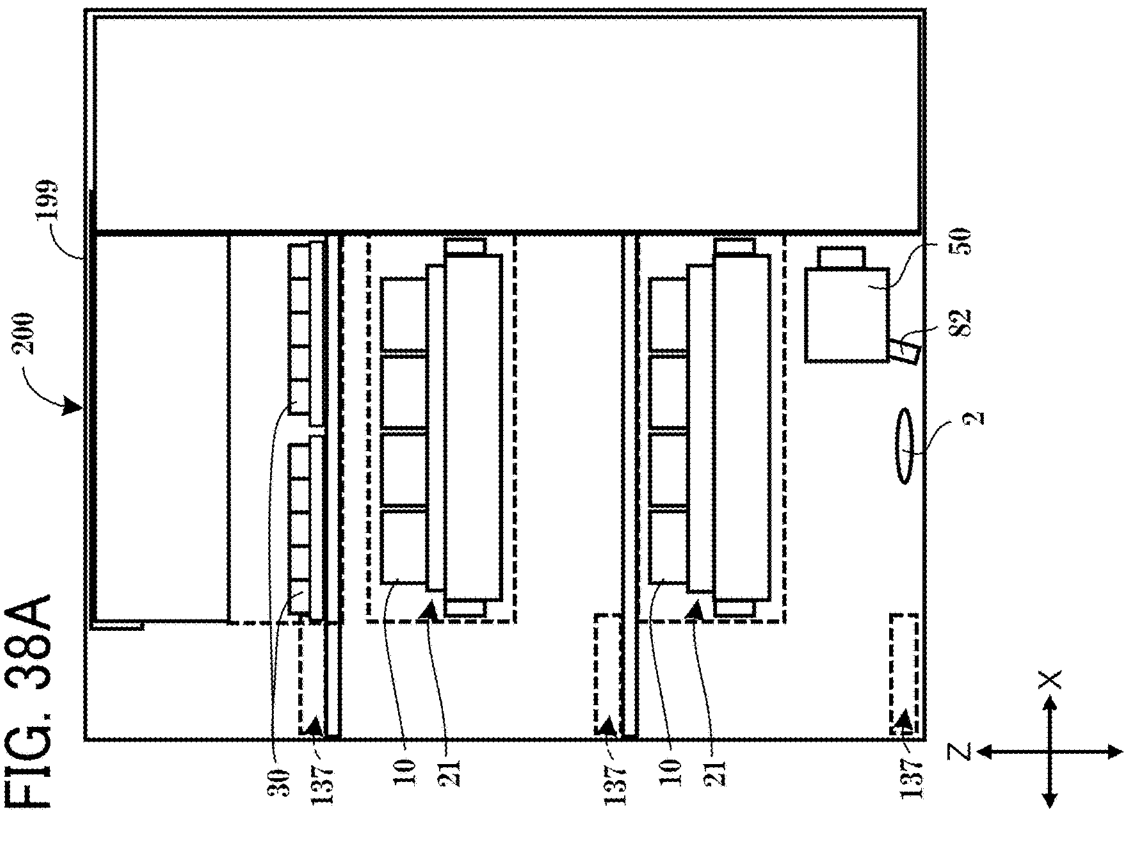
FIG. 38A is a front view of a medicine dispensing apparatus having a guide to guide a medicine package to a second space for retraction.

FIG. 38A is a front view of the medicine dispensing apparatus 200 having the guide 82 to guide the medicine package 2 to a second space for retraction 137.

FIG. 38B is another front view of the medicine dispensing apparatus 200 having the guide 82 to guide the medicine package 2 to the second space for retraction 137.

As illustrated in FIG. 38A, a guide 82 that guides the dropped medicine package 2 is arranged under the pickup device 50. As the pickup device 50 with the guide 82 is moved by the conveyor 90 in the X-axis direction toward the left in FIG. 38A, the dropped medicine package 2 is moved to a second space for retraction 137 for first-order storage. Due to such a configuration, the dropped medicine package 2 can be dealt with just by checking a specific point inside the medicine dispensing apparatus 200.

The guide 82 is attached to a lower portion of the pickup device 50 at an oblique angle, and moves in contact with the medicine package 2. The guide 82 is attached to a lower portion of the pickup device 50 at an obtuse angle so as to move the medicine package 2 with reliability in contact with the medicine package 2 over a wide area. Due to such a configuration, the medicine package 2 as illustrated in FIG. 38A is scooped up and moved. The guide 82 may be made of an elastically-deformable material such as rubber that does not damage the medicine package 2 even if it contacts the medicine package 2, or may be formed of fibrous aggregate such as a broom.

As illustrated in FIG. 38A, the second space for retraction 137 may be arranged to the left of the cartridges 10 at the lowermost stage, the cartridges 10 at a middle stage, and the medicine dispensing tray 30. As illustrated in FIG. 38B, the second space for retraction 137 may be arranged only at the bottom of the housing 199.

For example, when the medicine package 2 is dropped to an area below the cartridges 10 at the upper stage as illustrated in FIG. 38B, the dropped medicine package 2 is moved by the guide 82 such that the dropped medicine package 2 is further dropped and added up in the second space for retraction 137 at the bottom of the housing 199. When multiple second spaces for retraction 137 are extensively arranged at stages as illustrated in FIG. 38A, the medicine packages 2 that are dropped and added up in the second spaces for retraction 137 at varying stages need to be checked.

Figure 39B:
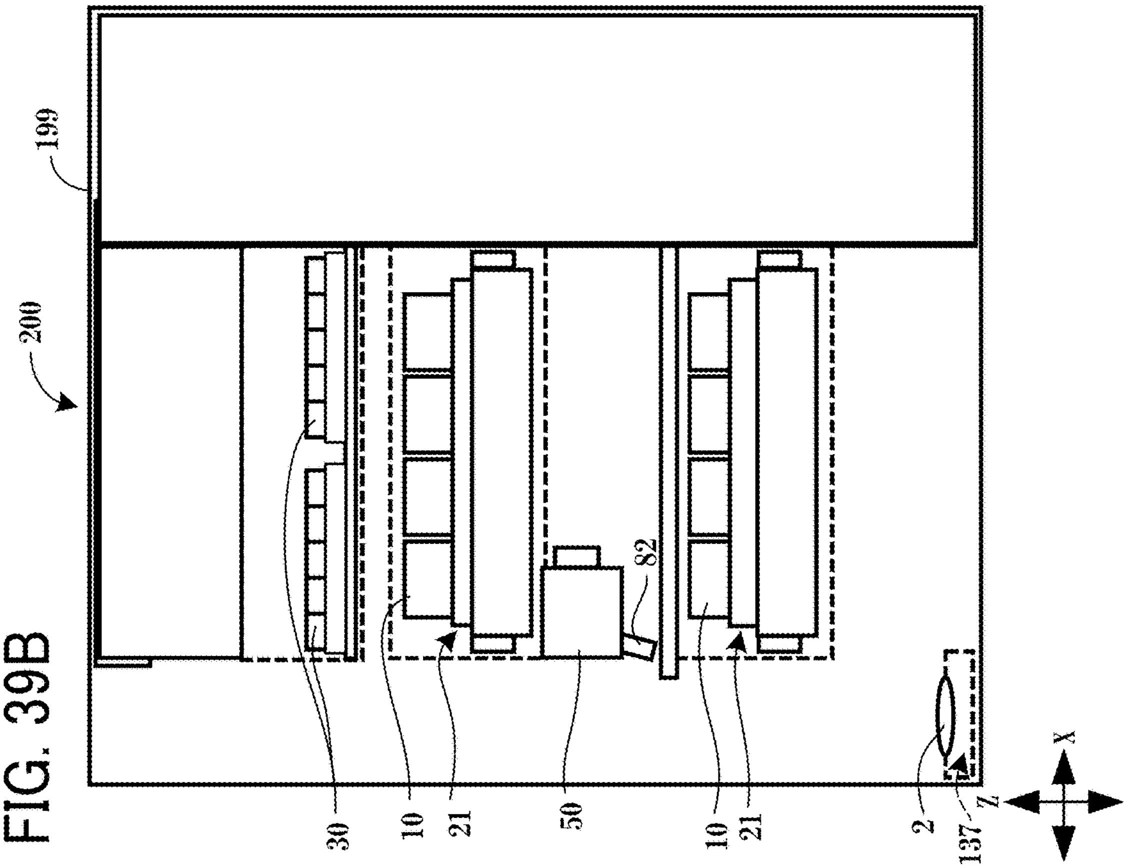
FIG. 39A and FIG. 39B are diagrams each of which illustrates an operation in which a medicine package dropped in an area below a cartridge at an upper stage is moved by a pickup device with a guide to a second space for retraction for first-order storage.
Figure 39A:
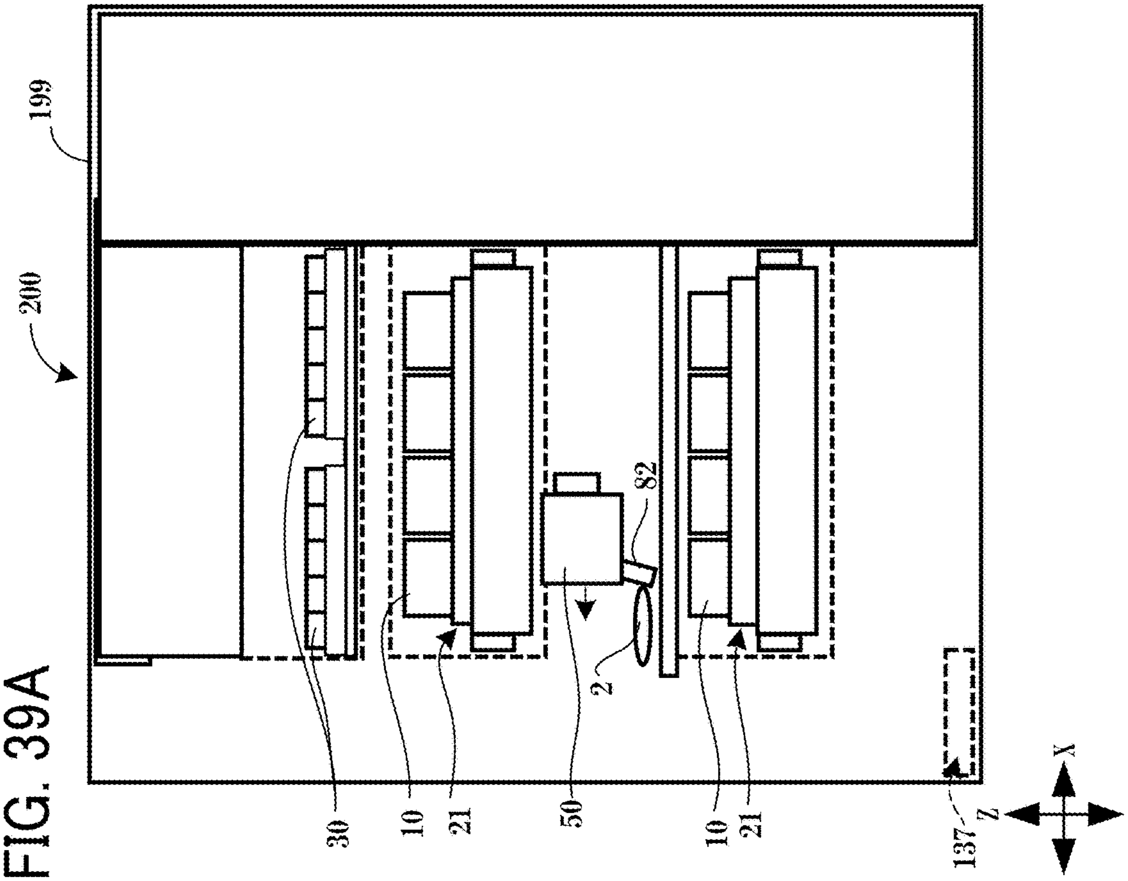

By contrast, when the medicine package 2 is dropped to, for example, an area below the cartridges 10 at the upper stage as illustrated in FIG. 38B, the pickup device 50 with the guide 82 is moved by the conveyor 90 in the X-axis direction toward the left as illustrated in FIG. 39A and FIG. 39B. Due to such a configuration, the dropped medicine package 2 can be moved to the second space for retraction 137 at the bottom of the housing 199 for first-order storage, and the dropped medicine package 2 can be dealt with just by checking a specific point inside the medicine dispensing apparatus 200. Accordingly, the number of places to be checked is reduced to one, and the efficiency increases.

Figure 40B:
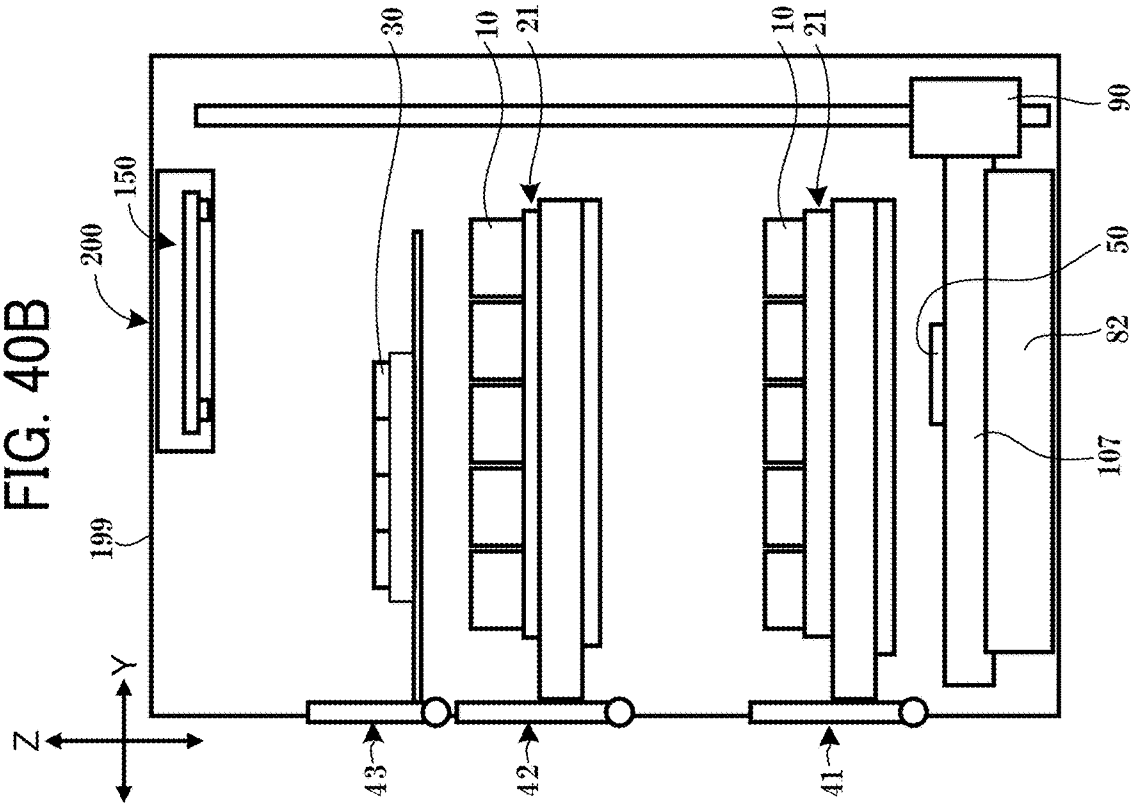
FIG. 40A and FIG. 40B are diagrams each of which illustrates a guide arranged at a different place inside a medicine dispensing apparatus.
Figure 40A:
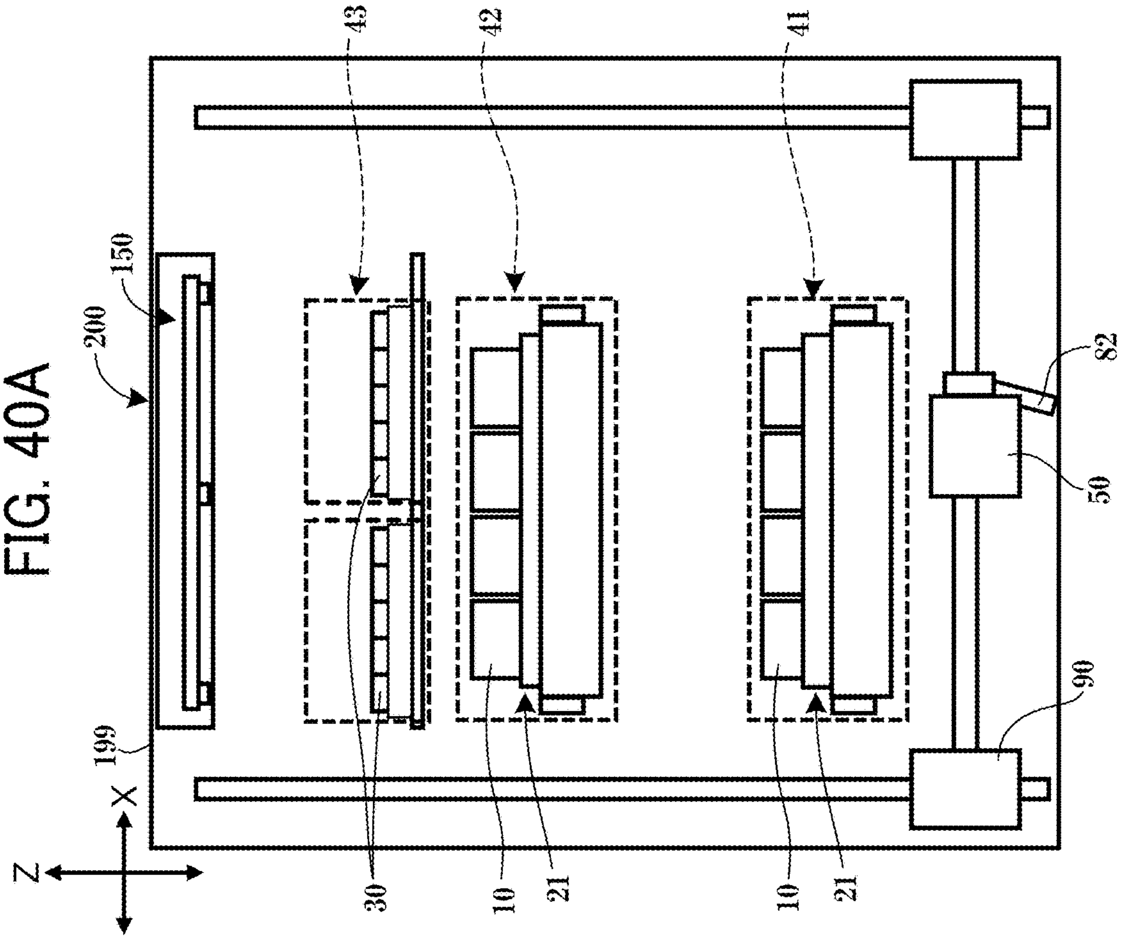

As illustrated in FIG. 40A and FIG. 40B, the guide 82 may be provided for the Y-guide unit 107 support the pickup device 50 in a movable manner in the Y-axis direction. In such a configuration, the dropped medicine package 2 can be moved to a space for retraction only by the movement in the X-axis direction.

Figure 41:
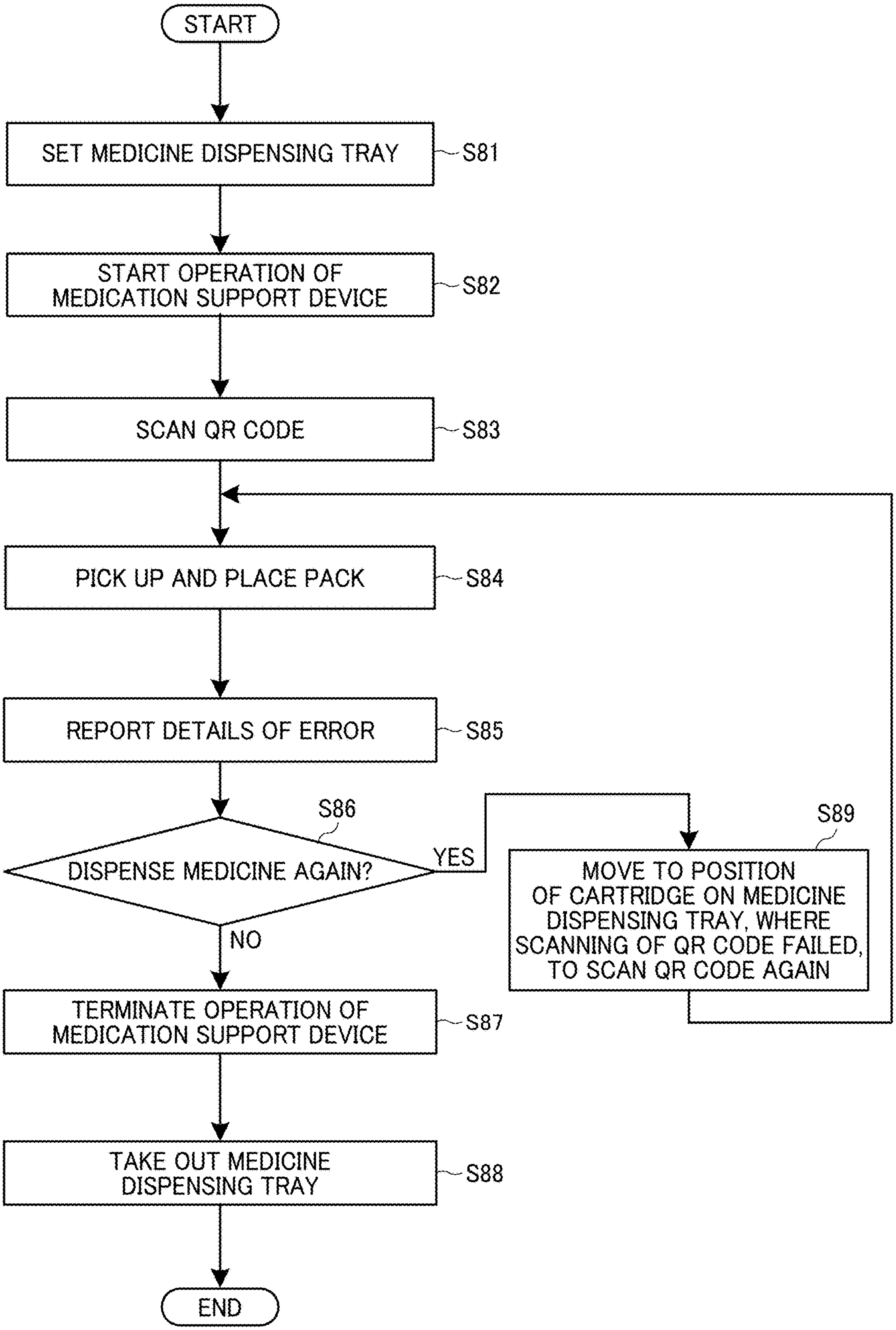
FIG. 41 is a flowchart of an operation in which medicine is dispensed again.

FIG. 41 is a flowchart of an operation in which medicine is dispensed again after an incident where medicine is not dispensed due to an error.

Figure 42:
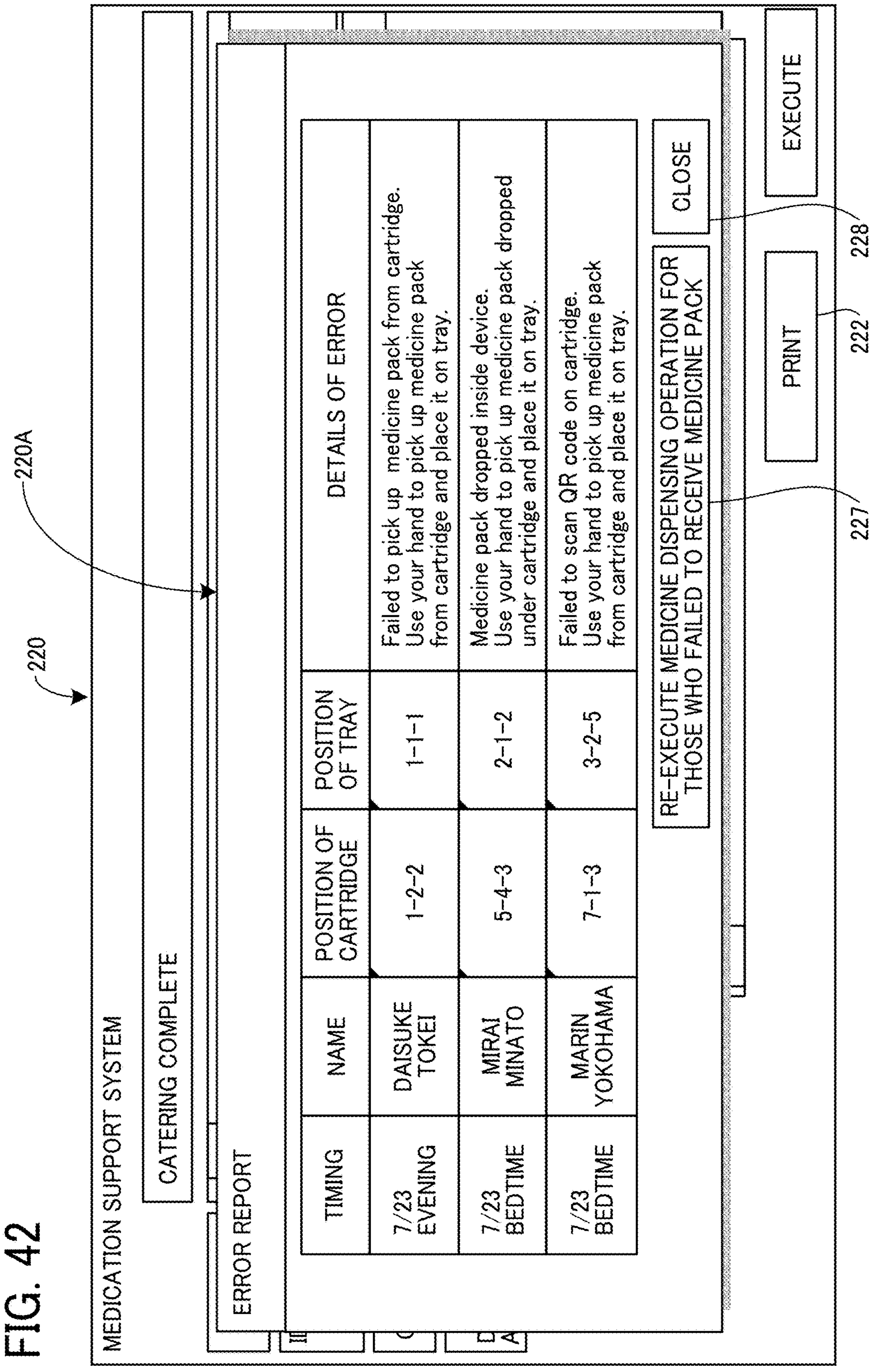
FIG. 42 is a diagram illustrating a window indicating what actually happened in an error.

FIG. 42 is a diagram illustrating the window 220A indicating what actually happened in the error.

The flowchart of the operation in FIG. 41 starts from step S81. The objects of this operation include the position of the cartridge 10 or the subdivision box 34 was unknown due to the failures in reading the QR code at the time of first medicine dispensing operation or persons for which the medicine package 2 could not be picked up from the cartridge 10 at the time of first medicine dispensing operation.

After the operations equivalent to those of FIG. 20, in step S84, a series of picking operation and placing operation is performed. Subsequently, in step S85, the details of the error are reported. By touching or pressing down "re-execute medicine dispensing operation for those who failed to receive medicine pack" key 227 displayed on the window 220A illustrated in FIG. 42, the medicine dispensing operation can be re-executed for those who failed to receive the medicine pack 2. For example, if the number of errors in the details of the error is a few and such errors can manually be dealt with quickly, the process may be ended by touching or pressing down a close key 228. The choice of re-execution is effective when there are a large number of errors.

As illustrated in FIG. 41 and FIG. 42, after the medicine dispensing operation is completed, medicine is dispensed again after an incident where the medicine is not dispensed due to an error. Due to such a configuration of the medication support device, human errors that may occur due to manual operations are reduced.

The above embodiments of the present disclosure described above substantially include, for example, the following aspects.

First Aspect

A medication support device such as the medication support device 300 includes a container such as the cartridge 10 to store a plurality of medicine packages such as the medicine packages 2 stacked on top of each other in layers, a pickup device such as the pickup device 50 to pick up a specific one of the plurality of medicine packages from the container, a conveyor such as the conveyor 90 to convey the specific one of the plurality of medicine packages picked up by the pickup device, a medicine dispenser such as the medicine dispensing tray 30 including a prescribed position to which the medicine package conveyed by the conveyor is dispensed, a medication-related information reader such as the medication-related information reader unit 65 to read medication-related information such as the medication-related information 6*c* including at least a name of a patient who takes medicines and a time of medication, and a controller such as the controller 150 to control a medicine dispensing operation in which the medicine package picked up from the container is dispensed to the medicine dispenser, based on the medication-related information read by the medication-related information reader, the controller skipping a process with an abnormality and making the medicine dispensing operation continue after the medicine dispensing operation starts.

According to the first aspect, when abnormalities are detected, a process with such abnormalities is skipped, and the medicine dispensing operation continues. Due to such a configuration, a user including, for example, a nurse practitioner and care worker does not have to keep manipulations during the medicine dispensing operation, and he or she can work on other tasks during the medicine dispensing operation moving away from the medication support device.

Second Aspect

According to the first aspect, after the medicine dispensing operation is all completed, the controller gives notification of the process with the abnormality having occurred during the medicine dispensing operation.

According to the second aspect, after the medicine dispensing operation is completed, the medicine packages that are not yet dispensed due to abnormalities can be checked all at once. Accordingly, it is not necessary for a user to manipulate the device during the operation, and that user can leave the medication support device.

Third Aspect

According to the first or second aspect, when a picking-up operation of the medicine package from the container is not successful, the medicine dispensing operation for a next person to which the medicine package is to be dispensed is performed.

According to the third aspect, the medication support device does not stop its operation midway, and the time for the medicine dispensing operation as a whole can be shortened.

Fourth Aspect

According to the first or second aspect, when dispensing the medicine package to the specific position of the medicine dispenser is not successful, the medicine dispensing operation for a next person to which the medicine package is to be dispensed is performed.

According to the fourth aspect, the device or apparatus related to the medication support device does not stop its operation midway, and the time for the medicine dispensing operation as a whole can be shortened.

Fifth Aspect

According to one of the first to fourth aspects, when the medication-related information is not read by the medication-related information reader, the controller excludes a related object from an object to which the medicine package is to be dispensed.

According to the fifth aspect, the device or apparatus related to the medication support device does not stop its operation midway, and the time for the medicine dispensing operation as a whole can be shortened.

Sixth Aspect

According to one of the first to fifth aspects, a sensor such as the pack sensor 127 and the optical sensor 129 to detect the medicine package that is dropped, and a notifier such as the LED 133*a* to the LED 133*c* to give notification of a droppage location of the medicine package are further included.

According to the sixth aspect, when an abnormality occurs and the medicine package is dropped, the medicine package that is dropped inside the medication support device can easily be discovered.

Seventh Aspect

According to one of the first to sixth aspects, the controller uses a pause mode that is turned on when the execute key 225 is touched or pressed down to pause the medication support device when the medication support device operates abnormally or an operation continue mode that is turned on when the execute (continue) key 224 is touched or pressed down to continue the medicine dispensing operation until the medicine dispensing operation for all the persons to which the medicine package is to be dispensed is completed after the medicine dispensing operation is started, and when the medication support device operates abnormally, the controller switches a mode between the pause mode and the operation continue mode.

According to the seventh aspect, when a user operates around the medication support device, abnormalities in operation are immediately addressed and the time for the operation as a whole can be shortened.

Eighth Aspect

According to one of the first to seventh aspects, a first space for retraction such as the first spaces for retraction 134 to 136 is further included in a conveyance path of the conveyor, and the first space for retraction keeps the medicine package dropped during conveyance.

According to the eighth aspect, when the medicine package is dropped and the next medicine dispensing operation is to be performed, all the medicine dispensing operations can be completed without damaging the medicine package.

Ninth Aspect

According to one of the first to eighth aspects, a guide such as the guide 82 is further included at one of the pickup device and the conveyor to guide the medicine package dropped inside the medication support device to a second space for retraction such as the second space for retraction 137.

According to the ninth aspect, the medicine package that is dropped can be retracted to a safe place with no damage. Moreover, the medicine package that is dropped inside the medication support device can easily be found.

Tenth Aspect

According to one of the first to ninth aspects, when the medicine dispensing operation is performed again after the medicine dispensing operation is completed, the medicine dispensing operation is performed again for a position to which the medicine package is not successfully dispensed due to an abnormality in the medication support device.

According to the tenth aspect, the medication support device does the job automatically, and human errors that may occur due to manual operations are reduced.

The above-described embodiments are illustrative and do not limit the present disclosure. Thus, numerous additional modifications and variations are possible in light of the above teachings. For example, elements and/or features of different illustrative embodiments may be combined with each other and/or substituted for each other within the scope of the present disclosure.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application-specific integrated circuit (ASIC), digital signal processor (DSP), field-programmable gate array (FPGA), and conventional circuit components arranged to perform the recited functions.

What is claimed is:

1. A medication support device comprising:

a container to store a medicine package in which a plurality of medicines are packed;

a pickup device to pick up the medicine package from the container;

a conveyor to convey the medicine package picked up by the pickup device;

a space for retraction in a conveyance path of the conveyor, wherein the space for retraction keeps the medicine package dropped during conveyance;

a medicine dispenser including a prescribed position to which the medicine package conveyed by the conveyor is dispensed;

a medication-related information reader to read medication-related information including at least a name of a patient who takes medicines and a time of medication; and processing circuitry to control a medicine dispensing operation in which the medicine package picked up from the container is dispensed to the medicine dispenser, based on the medication-related information read by the medication-related information reader, and skip a process with an abnormality and make the medicine dispensing operation continue after the medicine dispensing operation starts.

2. The medication support device according to claim 1, wherein, after the medicine dispensing operation is all completed, the processing circuitry gives notification of the process with the abnormality having occurred during the medicine dispensing operation.

3. The medication support device according to claim 1, wherein, when a picking-up operation of the medicine package from the container is not successful, the medicine dispensing operation for a next person to which the medicine package is to be dispensed is performed.

4. The medication support device according to claim 1, wherein, when dispensing the medicine package to the prescribed position of the medicine dispenser is not successful, the medicine dispensing operation for a next person to which the medicine package is to be dispensed is performed.

5. The medication support device according to claim 1, wherein, when the medication-related information is not read by the medication-related information reader, the processing circuitry excludes a related object from an object to which the medicine package is to be dispensed.

6. The medication support device according to claim 1, further comprising:

a sensor to detect the medicine package that is dropped; and a notifier to give notification of a droppage location of the medicine package.

7. The medication support device according to claim 1, wherein the processing circuitry uses a pause mode to pause the medication support device when the medication support device operates abnormally or an operation continue mode to continue the medicine dispensing operation until the medicine dispensing operation for all persons to which the medicine package is to be dispensed is completed after the medicine dispensing operation is started, and wherein, when the medication support device operates abnormally, the processing circuitry switches a mode between the pause mode and the operation continue mode.

8. The medication support device according to claim 1, wherein the space comprises a plurality of spaces for retraction in the conveyance path of the conveyor, each of the spaces having a height in a vertical direction equal to or greater than a thickness of the medicine package.

9. The medication support device according to claim 1, wherein, when the medicine dispensing operation is performed again after the medicine dispensing operation is completed, the medicine dispensing operation is performed again for a position to which the medicine package is not successfully dispensed due to an abnormality in the medication support device.

10. A medication support device comprising:

a container to store a medicine package in which a plurality of medicines are packed;

a pickup device to pick up the medicine package from the container;

a conveyor to convey the medicine package picked up by the pickup device;

a guide disposed at one of the pickup device and the conveyor to guide the medicine package dropped inside the medication support device to a space for retraction;

a medicine dispenser including a prescribed position to which the medicine package conveyed by the conveyor is dispensed;

a medication-related information reader to read medication-related information including at least a name of a patient who takes medicines and a time of medication; and processing circuitry to control a medicine dispensing operation in which the medicine package picked up from the container is dispensed to the medicine dispenser, based on the medication-related information read by the medication-related information reader, and skip a process with an abnormality and make the medicine dispensing operation continue after the medicine dispensing operation starts.

11. The medication support device according to claim 10, wherein, after the medicine dispensing operation is all completed, the processing circuitry gives notification of the process with the abnormality having occurred during the medicine dispensing operation.

12. The medication support device according to claim 10, wherein, when a picking-up operation of the medicine package from the container is not successful, the medicine dispensing operation for a next person to which the medicine package is to be dispensed is performed.

13. The medication support device according to claim 10, wherein, when dispensing the medicine package to the prescribed position of the medicine dispenser is not successful, the medicine dispensing operation for a next person to which the medicine package is to be dispensed is performed.

14. The medication support device according to claim 10, wherein, when the medication-related information is not read by the medication-related information reader, the processing circuitry excludes a related object from an object to which the medicine package is to be dispensed.

15. The medication support device according to claim 10, further comprising:

a sensor to detect the medicine package that is dropped; and a notifier to give notification of a droppage location of the medicine package.

16. The medication support device according to claim 10, wherein the processing circuitry uses a pause mode to pause the medication support device when the medication support device operates abnormally or an operation continue mode to continue the medicine dispensing operation until the medicine dispensing operation for all persons to which the medicine package is to be dispensed is completed after the medicine dispensing operation is started, and wherein, when the medication support device operates abnormally, the processing circuitry switches a mode between the pause mode and the operation continue mode.

17. The medication support device according to claim 10, wherein, when the medicine dispensing operation is performed again after the medicine dispensing operation is completed, the medicine dispensing operation is performed again for a position to which the medicine package is not successfully dispensed due to an abnormality in the medication support device.

18. The medication support device according to claim 10, wherein the guide is arranged under the pickup device.

19. The medication support device according to claim 10, wherein the guide is disposed at a lower portion of the pickup device at an oblique angle.

20. The medication support device according to claim 10, wherein the guide is made of an elastically-deformable material.

* * * * *